US008828433B2

(12) United States Patent
Claude et al.

(10) Patent No.: US 8,828,433 B2
(45) Date of Patent: Sep. 9, 2014

(54) HYDROGEL BIOSCAFFOLDINGS AND BIOMEDICAL DEVICE COATINGS

(75) Inventors: Charles Claude, Flagstaff, AZ (US);
Connie Kwok, Shoreline, WA (US);
Gene Michal, San Francisco, CA (US);
Jihong Qu, Maple Grove, MN (US);
Sophia Liao, Irvine, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 778 days.

(21) Appl. No.: 11/110,223

(22) Filed: Apr. 19, 2005

(65) Prior Publication Data

US 2009/0226519 A1   Sep. 10, 2009

(51) Int. Cl.
*A61K 9/14* (2006.01)

(52) U.S. Cl.
USPC .......... 424/484; 424/93.7; 514/9.4; 514/13.3; 514/16.4

(58) Field of Classification Search
USPC ........................................................ 424/423
See application file for complete search history.

(56) References Cited

U.S. PATENT DOCUMENTS

| | | |
|---|---|---|
| 2,512,569 A | 6/1950 | Saffir |
| 3,144,868 A | 8/1964 | Jascalevich |
| 3,584,624 A | 6/1971 | de Ciutiis |
| 3,780,733 A | 12/1973 | Martinez-Mangor |
| 3,804,097 A | 4/1974 | Rudie |
| 3,890,976 A | 6/1975 | Bazell et al. |
| 4,141,973 A | 2/1979 | Balazs |
| 4,617,186 A | 10/1986 | Schafer |
| 4,794,931 A | 1/1989 | Yock |
| 4,818,291 A | 4/1989 | Iwatsuki et al. |
| 4,842,590 A | 6/1989 | Tanabe et al. |
| 5,000,185 A | 3/1991 | Yock |
| 5,024,234 A | 6/1991 | Leary et al. |
| 5,026,350 A | 6/1991 | Tanaka et al. |
| 5,049,130 A | 9/1991 | Powell |
| 5,092,848 A | 3/1992 | DeCiutiis |
| 5,100,185 A | 3/1992 | Menke et al. |
| 5,109,859 A | 5/1992 | Jenkins |
| 5,116,317 A | 5/1992 | Carson et al. |
| 5,128,326 A | 7/1992 | Balazs et al. |
| 5,171,217 A | 12/1992 | March et al. |
| 5,202,745 A | 4/1993 | Sorin et al. |
| 5,203,338 A | 4/1993 | Jang |
| 5,242,427 A | 9/1993 | Bilweis |
| 5,270,300 A | 12/1993 | Hunziker |
| 5,291,267 A | 3/1994 | Sorin et al. |
| 5,306,250 A | 4/1994 | March et al. |
| 5,321,501 A | 6/1994 | Swanson et al. |
| 5,328,955 A | 7/1994 | Rhee et al. |
| 5,336,252 A | 8/1994 | Cohen |
| 5,354,279 A | 10/1994 | Hofling |
| 5,365,325 A | 11/1994 | Kumasaka et al. |
| 5,372,138 A | 12/1994 | Crowley et al. |
| 5,380,292 A | 1/1995 | Wilson |
| 5,419,777 A | 5/1995 | Hofling et al. |
| 5,437,632 A | 8/1995 | Engelson |
| 5,455,039 A | 10/1995 | Edelman et al. |
| 5,459,570 A | 10/1995 | Swanson et al. |
| 5,464,395 A | 11/1995 | Faxon et al. |
| 5,465,147 A | 11/1995 | Swanson |
| 5,485,486 A | 1/1996 | Gilhousen et al. |
| 5,499,630 A | 3/1996 | Hiki et al. |
| 5,516,532 A | 5/1996 | Atala et al. |
| 5,540,912 A | 7/1996 | Roorda et al. |
| 5,546,948 A | 8/1996 | Hamm et al. |
| 5,554,389 A | 9/1996 | Badylak et al. |
| 5,575,815 A | 11/1996 | Siepian et al. |
| 5,580,714 A | 12/1996 | Polovina |
| 5,580,856 A | 12/1996 | Prestrelski et al. |

(Continued)

FOREIGN PATENT DOCUMENTS

| | | |
|---|---|---|
| EP | 0331584 | 9/1989 |
| EP | 0835667 | 4/1998 |

(Continued)

OTHER PUBLICATIONS

Agocha A. et al. "Hypoxia regulates basal and induced DNA synthesis and collagen type I production in human cardiac fibroblasts: effects of transforming growth factor-beta 1, thyroid hormone, angiotensin II and basic fibroblast growth factor," *J. Mol. Cell. Cardiol.* 29(8): 2233-2244. (Apr. 1997).

(Continued)

*Primary Examiner* — Jon P Weber
*Assistant Examiner* — Teresa E Knight
(74) *Attorney, Agent, or Firm* — Randy Shen; Blakely Sokoloff Taylor & Zafman LLP

(57) ABSTRACT

Bioscaffoldings formed of hydrogels that are crosslinked in situ in an infarcted region of the heart (myocardium) by a Michael's addition reaction or by a disulfide bond formed by an oxidative process are described. Each of the bioscaffoldings described includes hyaluronan as one of the hydrogel components and the other component is selected from collagen, collagen-laminin, poly-1-lysine, and fibrin. The bioscaffolding may further include an alginate component. The bioscaffoldings may have biofunctional groups such as angiogenic factors and stem cell homing factors bound to the collagen, collagen-laminin, poly-1-lysine, or fibrinogen hydrogel component. In particular, the biofunctional groups may be PR11, PR39, VEGF, bFGF, a polyarginine/DNA plasmid complex, or a DNA/polyethyleneimine (PEI) complex. Additionally, the hydrogel components may be injected into the infarct region along with stem cells and microspheres containing stem cell homing factors. The bioscaffolding may be formed on a stent or a cardiac medical device.

6 Claims, 31 Drawing Sheets

(56) References Cited

U.S. PATENT DOCUMENTS

| | | |
|---|---|---|
| 5,588,432 A | 12/1996 | Crowley |
| 5,621,610 A | 4/1997 | Moore et al. |
| 5,631,011 A | 5/1997 | Wadstrom |
| 5,642,234 A | 6/1997 | Altman et al. |
| 5,655,548 A | 8/1997 | Nelson et al. |
| 5,667,778 A | 9/1997 | Atala |
| 5,669,883 A | 9/1997 | Scarfone et al. |
| 5,672,153 A | 9/1997 | Lax et al. |
| 5,676,151 A | 10/1997 | Yock |
| 5,693,029 A | 12/1997 | Leonhardt |
| 5,722,403 A | 3/1998 | McGee et al. |
| 5,725,551 A | 3/1998 | Myers et al. |
| 5,730,732 A | 3/1998 | Sardelis et al. |
| 5,740,808 A | 4/1998 | Panescu et al. |
| 5,749,915 A | 5/1998 | Slepian |
| 5,772,665 A | 6/1998 | Glad et al. |
| 5,785,689 A | 7/1998 | De Toledo et al. |
| 5,795,331 A | 8/1998 | Cragg et al. |
| 5,810,885 A | 9/1998 | Zinger |
| 5,811,533 A | 9/1998 | Gold et al. |
| 5,827,313 A | 10/1998 | Ream |
| 5,843,156 A | 12/1998 | Slepian et al. |
| 5,874,500 A | 2/1999 | Rhee et al. |
| 5,879,713 A | 3/1999 | Roth et al. |
| 5,900,433 A | 5/1999 | Igo et al. |
| 5,906,934 A | 5/1999 | Grande et al. |
| 5,919,449 A | 7/1999 | Dinsmore |
| 5,935,160 A | 8/1999 | Auricchio et al. |
| 5,939,323 A | 8/1999 | Valentini et al. |
| 5,941,868 A | 8/1999 | Kaplan et al. |
| 5,957,941 A | 9/1999 | Ream |
| 5,968,064 A | 10/1999 | Selmon et al. |
| 5,979,449 A | 11/1999 | Steer |
| 5,980,887 A | 11/1999 | Isner et al. |
| 5,981,568 A | 11/1999 | Kunz et al. |
| 5,984,908 A | 11/1999 | Davis et al. |
| 5,997,536 A | 12/1999 | Osswald et al. |
| 6,022,540 A | 2/2000 | Bruder et al. |
| 6,045,565 A | 4/2000 | Ellis et al. |
| 6,050,949 A | 4/2000 | White et al. |
| 6,051,071 A | 4/2000 | Charvet et al. |
| 6,051,648 A | 4/2000 | Rhee et al. |
| 6,056,744 A | 5/2000 | Edwards |
| 6,058,329 A | 5/2000 | Salo et al. |
| 6,060,053 A | 5/2000 | Atala |
| 6,068,599 A | 5/2000 | Saito et al. |
| 6,071,305 A | 6/2000 | Brown et al. |
| 6,086,582 A | 7/2000 | Altman et al. |
| 6,093,177 A | 7/2000 | Javier, Jr. et al. |
| 6,099,563 A | 8/2000 | Zhong |
| 6,099,864 A | 8/2000 | Morrison et al. |
| 6,102,887 A | 8/2000 | Altman |
| 6,102,904 A | 8/2000 | Vigil et al. |
| 6,102,926 A | 8/2000 | Tartaglia et al. |
| 6,120,520 A | 9/2000 | Saadat et al. |
| 6,120,904 A | 9/2000 | Hostettler et al. |
| 6,127,448 A | 10/2000 | Domb |
| 6,133,231 A | 10/2000 | Ferrara et al. |
| 6,134,003 A | 10/2000 | Tearney et al. |
| 6,146,373 A | 11/2000 | Cragg et al. |
| 6,151,525 A | 11/2000 | Soykan et al. |
| 6,152,141 A | 11/2000 | Stevens et al. |
| 6,153,428 A | 11/2000 | Gustafsson et al. |
| 6,159,443 A | 12/2000 | Hallahan |
| 6,162,202 A | 12/2000 | Sicurelli et al. |
| 6,175,669 B1 | 1/2001 | Colston et al. |
| 6,177,407 B1 | 1/2001 | Rodgers et al. |
| 6,179,809 B1 | 1/2001 | Khairkhahan et al. |
| 6,183,432 B1 | 2/2001 | Milo |
| 6,183,444 B1 | 2/2001 | Glines et al. |
| 6,187,330 B1 | 2/2001 | Wang et al. |
| 6,190,353 B1 | 2/2001 | Makower et al. |
| 6,191,144 B1 | 2/2001 | Isner |
| 6,192,271 B1 | 2/2001 | Hayman |
| 6,193,763 B1 | 2/2001 | Mackin |
| 6,197,324 B1 | 3/2001 | Crittenden |
| 6,201,608 B1 | 3/2001 | Mandella et al. |
| 6,206,893 B1 | 3/2001 | Klein et al. |
| 6,206,914 B1 | 3/2001 | Soykan et al. |
| 6,207,180 B1 | 3/2001 | Ottoboni et al. |
| 6,210,392 B1 | 4/2001 | Vigil et al. |
| 6,217,527 B1 | 4/2001 | Selmon et al. |
| 6,217,554 B1 | 4/2001 | Green |
| 6,221,049 B1 | 4/2001 | Selmon et al. |
| 6,231,546 B1 | 5/2001 | Milo et al. |
| 6,235,000 B1 | 5/2001 | Milo et al. |
| 6,241,710 B1 | 6/2001 | VanTassel et al. |
| 6,251,104 B1 | 6/2001 | Kesten et al. |
| 6,283,947 B1 | 9/2001 | Mirzaee |
| 6,287,285 B1 | 9/2001 | Michal et al. |
| 6,290,729 B1 | 9/2001 | Slepian et al. |
| 6,296,602 B1 | 10/2001 | Headley |
| 6,299,604 B1 | 10/2001 | Ragheb et al. |
| 6,309,370 B1 | 10/2001 | Haim et al. |
| 6,312,725 B1 | 11/2001 | Wallace et al. |
| 6,315,994 B2 | 11/2001 | Usala et al. |
| 6,323,278 B2 | 11/2001 | Rhee et al. |
| RE37,463 E | 12/2001 | Altman |
| 6,328,229 B1 | 12/2001 | Duronio et al. |
| 6,331,309 B1 | 12/2001 | Jennings, Jr. et al. |
| 6,333,194 B1 | 12/2001 | Levy et al. |
| 6,334,872 B1 | 1/2002 | Termin et al. |
| 6,338,717 B1 | 1/2002 | Ouchi |
| 6,346,098 B1 | 2/2002 | Yock et al. |
| 6,346,099 B1 | 2/2002 | Altman |
| 6,346,515 B1 | 2/2002 | Pitaru et al. |
| 6,358,247 B1 | 3/2002 | Altman et al. |
| 6,358,258 B1 | 3/2002 | Arcia et al. |
| 6,360,129 B1 | 3/2002 | Ley et al. |
| 6,368,285 B1 | 4/2002 | Osadchy et al. |
| 6,371,935 B1 | 4/2002 | Macoviak et al. |
| 6,371,992 B1 | 4/2002 | Tanagho et al. |
| 6,379,379 B1 | 4/2002 | Wang |
| 6,385,476 B1 | 5/2002 | Osadchy et al. |
| 6,391,052 B2 | 5/2002 | Buirge et al. |
| 6,395,023 B1 | 5/2002 | Summers |
| 6,409,716 B1 | 6/2002 | Sahatjian et al. |
| 6,416,510 B1 | 7/2002 | Altman et al. |
| 6,425,887 B1 | 7/2002 | McGuckin et al. |
| 6,432,119 B1 | 8/2002 | Saadat |
| 6,436,135 B1 | 8/2002 | Goldfarb |
| 6,440,947 B1 | 8/2002 | Barron et al. |
| 6,443,941 B1 | 9/2002 | Slepian et al. |
| 6,443,949 B2 | 9/2002 | Altman |
| 6,447,504 B1 | 9/2002 | Ben-Haim et al. |
| 6,458,095 B1 | 10/2002 | Wirt et al. |
| 6,458,098 B1 | 10/2002 | Kanesaka |
| 6,464,862 B2 | 10/2002 | Bennett |
| 6,465,001 B1 | 10/2002 | Hubbell et al. |
| 6,478,775 B1 | 11/2002 | Galt et al. |
| 6,478,776 B1 | 11/2002 | Rosenman et al. |
| 6,482,231 B1 | 11/2002 | Abatangelo et al. |
| 6,485,481 B1 | 11/2002 | Pfeiffer |
| 6,494,862 B1 | 12/2002 | Ray et al. |
| 6,514,217 B1 | 2/2003 | Selmon et al. |
| 6,544,227 B2 | 4/2003 | Sahatjian et al. |
| 6,544,230 B1 | 4/2003 | Flaherty et al. |
| 6,548,081 B2 | 4/2003 | Sadozai et al. |
| 6,554,801 B1 | 4/2003 | Steward et al. |
| 6,569,441 B2 | 5/2003 | Kunz et al. |
| 6,599,267 B1 | 7/2003 | Ray et al. |
| 6,602,241 B2 | 8/2003 | Makower et al. |
| 6,616,869 B2 | 9/2003 | Mathiowitz et al. |
| 6,620,927 B2 * | 9/2003 | Bulpitt et al. .............. 536/123.1 |
| 6,624,245 B2 | 9/2003 | Wallace et al. |
| 6,628,988 B2 | 9/2003 | Kramer et al. |
| 6,629,947 B1 | 10/2003 | Sahatjian et al. |
| 6,632,457 B1 | 10/2003 | Sawhney |
| 6,635,267 B1 | 10/2003 | Miyoshi et al. |
| 6,660,034 B1 | 12/2003 | Mandrusov et al. |
| 6,663,881 B2 | 12/2003 | Kunz et al. |
| 6,682,730 B2 | 1/2004 | Mickle et al. |
| 6,689,608 B1 | 2/2004 | Mikos et al. |
| 6,692,466 B1 | 2/2004 | Chow et al. |

(56) References Cited

U.S. PATENT DOCUMENTS

| | | |
|---|---|---|
| 6,702,744 B2 | 3/2004 | Mandrusov et al. |
| 6,706,034 B1 | 3/2004 | Bhat |
| 6,726,677 B1 | 4/2004 | Flaherty et al. |
| 6,726,923 B2 | 4/2004 | Iyer et al. |
| 6,737,072 B1 | 5/2004 | Angele et al. |
| 6,748,258 B1 | 6/2004 | Mueller et al. |
| 6,749,617 B1 | 6/2004 | Palasis et al. |
| 6,759,431 B2 | 7/2004 | Hunter et al. |
| 6,761,887 B1 | 7/2004 | Kavalkovich et al. |
| 6,777,000 B2 | 8/2004 | Ni et al. |
| 6,777,231 B1 | 8/2004 | Katz et al. |
| 6,790,455 B2 | 9/2004 | Chu et al. |
| 6,824,791 B2 | 11/2004 | Mathiowitz et al. |
| 6,858,229 B1 | 2/2005 | Hubbell et al. |
| 6,893,431 B2 | 5/2005 | Naimark et al. |
| 6,916,488 B1 | 7/2005 | Meier et al. |
| 6,916,648 B2 | 7/2005 | Goddard et al. |
| 6,926,692 B2 | 8/2005 | Katoh et al. |
| 6,992,172 B1 | 1/2006 | Chang et al. |
| 7,008,411 B1 | 3/2006 | Mandrusov et al. |
| 7,035,092 B2 | 4/2006 | Hillman et al. |
| 7,112,587 B2 | 9/2006 | Trimmer et al. |
| 7,129,210 B2 | 10/2006 | Lowinger et al. |
| 7,169,127 B2 | 1/2007 | Epstein et al. |
| 7,270,654 B2 | 9/2007 | Griego et al. |
| 7,273,469 B1 | 9/2007 | Chan et al. |
| 7,294,334 B1 | 11/2007 | Michal et al. |
| 7,361,360 B2 | 4/2008 | Kitabwalla et al. |
| 7,361,368 B2 | 4/2008 | Claude et al. |
| 7,374,774 B2 | 5/2008 | Bowlin et al. |
| 7,393,339 B2 | 7/2008 | Zawacki et al. |
| 7,438,692 B2 | 10/2008 | Tsonton et al. |
| 7,615,373 B2 | 11/2009 | Simpson et al. |
| 7,641,643 B2 | 1/2010 | Michal et al. |
| 7,732,190 B2 | 6/2010 | Michal et al. |
| 7,815,590 B2 | 10/2010 | Cooper |
| 7,854,944 B2 | 12/2010 | Mandrusov et al. |
| 8,038,991 B1 | 10/2011 | Stankus et al. |
| 8,187,621 B2 | 5/2012 | Michal |
| 8,192,760 B2 | 6/2012 | Hossainy et al. |
| 8,221,744 B2 | 7/2012 | Basu et al. |
| 8,293,226 B1 | 10/2012 | Basu et al. |
| 8,303,972 B2 | 11/2012 | Michal |
| 8,383,158 B2 | 2/2013 | Michal et al. |
| 8,388,948 B2 | 3/2013 | Basu et al. |
| 8,486,386 B2 | 7/2013 | Michal et al. |
| 8,486,387 B2 | 7/2013 | Michal et al. |
| 8,500,680 B2 | 8/2013 | Claude et al. |
| 8,521,259 B2 | 8/2013 | Mandrusov et al. |
| 8,608,661 B1 | 12/2013 | Mandrusov et al. |
| 8,609,126 B2 | 12/2013 | Michal et al. |
| 2001/0023349 A1 | 9/2001 | VanTassel et al. |
| 2001/0055615 A1 | 12/2001 | Wallace et al. |
| 2002/0006429 A1 | 1/2002 | Redmond et al. |
| 2002/0013408 A1 | 1/2002 | Rhee et al. |
| 2002/0042473 A1 | 4/2002 | Trollsas et al. |
| 2002/0072706 A1 | 6/2002 | Hiblar et al. |
| 2002/0076441 A1 | 6/2002 | Shih et al. |
| 2002/0077657 A1 | 6/2002 | Ginn et al. |
| 2002/0090725 A1 | 7/2002 | Simpson et al. |
| 2002/0102272 A1 | 8/2002 | Rosenthal et al. |
| 2002/0124855 A1 | 9/2002 | Chachques |
| 2002/0131974 A1 | 9/2002 | Segal |
| 2002/0142458 A1 | 10/2002 | Williams et al. |
| 2002/0146557 A1 | 10/2002 | Claude et al. |
| 2002/0151867 A1 | 10/2002 | McGuckin et al. |
| 2002/0169420 A1 | 11/2002 | Galt et al. |
| 2002/0188170 A1 | 12/2002 | Santamore et al. |
| 2003/0023202 A1 | 1/2003 | Nielson |
| 2003/0040712 A1 | 2/2003 | Ray et al. |
| 2003/0050597 A1 | 3/2003 | Dodge et al. |
| 2003/0078671 A1 | 4/2003 | Lesniak et al. |
| 2003/0105493 A1 | 6/2003 | Salo |
| 2003/0114505 A1 | 6/2003 | Nagao et al. |
| 2003/0125766 A1 | 7/2003 | Ding |
| 2003/0175410 A1 | 9/2003 | Campbell et al. |
| 2003/0233150 A1 | 12/2003 | Bourne et al. |
| 2004/0002650 A1 | 1/2004 | Mandrusov et al. |
| 2004/0181206 A1 | 9/2004 | Chiu |
| 2004/0185084 A1 | 9/2004 | Rhee et al. |
| 2004/0208845 A1 | 10/2004 | Michal et al. |
| 2004/0213756 A1 | 10/2004 | Michal et al. |
| 2004/0229856 A1 | 11/2004 | Chandrasekar et al. |
| 2005/0015048 A1 | 1/2005 | Chiu et al. |
| 2005/0031874 A1 | 2/2005 | Michal et al. |
| 2005/0042254 A1 | 2/2005 | Freyman et al. |
| 2005/0064038 A1 | 3/2005 | Dinh et al. |
| 2005/0065281 A1* | 3/2005 | Lutolf et al. ................. 525/54.1 |
| 2005/0070844 A1 | 3/2005 | Chow |
| 2005/0186240 A1 | 8/2005 | Ringeisen et al. |
| 2005/0281883 A1 | 12/2005 | Daniloff et al. |
| 2006/0149392 A1 | 7/2006 | Hsieh et al. |
| 2006/0233850 A1 | 10/2006 | Michal |
| 2007/0270948 A1 | 11/2007 | Wuh |
| 2008/0025943 A1 | 1/2008 | Michal et al. |
| 2009/0022817 A1 | 1/2009 | Michal et al. |
| 2012/0225040 A1 | 9/2012 | Hossainy et al. |
| 2012/0225041 A1 | 9/2012 | Hossainy et al. |

FOREIGN PATENT DOCUMENTS

| | | |
|---|---|---|
| EP | 0861632 A1 | 9/1998 |
| EP | 0938871 A2 | 9/1999 |
| EP | 1214077 | 1/2004 |
| FR | 2715855 | 8/1995 |
| GB | 2194144 A1 | 3/1988 |
| JP | 61205446 | 9/1986 |
| JP | H02145600 | 6/1990 |
| JP | 06507106 | 8/1994 |
| JP | 10236984 | 9/1998 |
| JP | 3063935 | 12/1999 |
| JP | 2000502380 | 2/2000 |
| JP | 2000262525 | 9/2000 |
| JP | 2001508666 | 7/2001 |
| JP | 2003062089 | 3/2003 |
| JP | 2007009185 | 1/2007 |
| JP | 2006523507 | 10/2009 |
| WO | WO 92/10142 A1 | 6/1992 |
| WO | WO-9315781 | 8/1993 |
| WO | WO-9522316 | 8/1995 |
| WO | WO-9733633 | 9/1997 |
| WO | WO 98/30207 | 7/1998 |
| WO | WO 98/54301 A2 | 12/1998 |
| WO | WO-9953943 | 10/1999 |
| WO | WO 00/16818 | 3/2000 |
| WO | WO-0054661 | 9/2000 |
| WO | WO 00/71196 A1 | 11/2000 |
| WO | WO 01/24775 A1 | 4/2001 |
| WO | WO-0124842 | 4/2001 |
| WO | WO 01/45548 A1 | 6/2001 |
| WO | WO 01/49357 A2 | 7/2001 |
| WO | WO-0200173 | 1/2002 |
| WO | WO-0204008 | 1/2002 |
| WO | WO 02/28450 A2 | 4/2002 |
| WO | WO 02/40070 A2 | 5/2002 |
| WO | WO-02/072166 | 9/2002 |
| WO | WO 02/087623 A1 | 11/2002 |
| WO | WO-03005961 | 1/2003 |
| WO | WO-03/022909 | 3/2003 |
| WO | WO-03022324 | 3/2003 |
| WO | WO 03/027234 A2 | 4/2003 |
| WO | WO-03026492 | 4/2003 |
| WO | WO 03/064637 A1 | 8/2003 |
| WO | WO-04/000915 | 12/2003 |
| WO | WO 2004/050013 A2 | 6/2004 |
| WO | WO-2004058305 | 7/2004 |
| WO | WO-2004060346 | 7/2004 |
| WO | WO 2004/066829 A2 | 8/2004 |
| WO | WO 2004/091592 | 10/2004 |
| WO | WO 2004/091592 A2 | 10/2004 |
| WO | WO-2004098669 | 11/2004 |
| WO | WO 2005/061019 | 7/2005 |
| WO | WO 2005/067890 | 7/2005 |
| WO | WO-2006027549 | 3/2006 |

(56) References Cited

FOREIGN PATENT DOCUMENTS

| WO | WO 2006/039704 | 4/2006 |
|---|---|---|
| WO | WO-2006014570 | 9/2006 |
| WO | WO 2006/113407 | 10/2006 |
| WO | WO-2006113407 | 10/2006 |
| WO | WO 2007/048831 | 3/2007 |
| WO | WO-2007145909 | 12/2007 |

OTHER PUBLICATIONS

Allemann, E. et al. "Kinetics of Blood Component Adsorption on poly(D,L-lactic acid) Nanoparticles: Evidence of Complement C3 Component Involvement," *J. Biomed. Mater. Res.* 37(2):229-234 (Nov. 1997), Abstract downloaded from the Internet at: http://www.ncbi.nlm.nih.gov/entrez/query.fcgi?cmd=Retrieve&db=PubMed, 1 page.

Anderson, J. et al. "Biodegradation and Biocompatibility of PLA and PLGA Microspheres," *Advanced Drug Delivery Reviews* 28 (1997), pp. 5-24.

Assmus, B. et al. "Transplantation of Progenitor Cells and Regeneration Enhancement in Acute Myocardial Infarction (TOPCARE-AMI)," *Circulation* (2002), 106:3009-3017, first page only (1 page).

Baxter, "FloSeal Matrix Hemostatic Sealant," downloaded from the Internet on Nov. 14, 2002, from: http://www.fusionmed.com/docs/surgeon/default.asp, 2 pages.

Berger et al. "Poly-L-cysteine," *J. Am. Chem. Soc.* 78(17):4483-4488 (Sep. 5, 1956).

Bernatowicz, M. et al. "Preparation of Boc-[S-(3-nitro-2-pyridinesulfenyl)]-cysteine and its use for Unsymmetrical Disulfide Bond Formation," *Int. J. Peptide Protein Res.* 28(2):107-112 (Aug. 1996).

Boland, E.D. "Electrospinning Collagen and Elastin: Preliminary Vascular Tissue Engineering," *Frontiers in Bioscience* vol. 9, pp. 1422-1432 (May 1, 2004).

Brust, G. "Polyimides," downloaded from the Internet at: http://www.pslc.ws/macrog/imide.htm, 4 pages (© 2005).

Buschmann, I. et al. "Arteriogenesis Versus Angiogenesis: Two Mechanisms of Vessel Growth," *News Physiol. Sci.* vol. 14 (Jun. 1999), pp. 121-125.

Canderm Pharma, "Technical Dossier: Artecoll," downloaded from the Internet on Oct. 22, 2002 from: http://www.canderm.com/artecoll/tech.html, 3 pages.

Capan, Y. et al. "Preparation and Characterization of Poly(D,L-lactide-co-glycolide) Microspheres for Controlled Release of Human Growth Hormone," *AAPS PharmSciTech*. 2003; 4(2): article 28. Downloaded from the Internet at: http://www.aapspharmscitech.org/view.asp?art=pt040228&pdf=yes (12 pages).

Caplan, M.J. et al. "Dependence on pH of Polarized Sorting of Secreted Proteins," *Nature* 329 (Oct. 15, 1987), p. 630.

Carpino, L. et al. "Tris(2-aminoethyl)amine as a Substitute for 4-(Aminomethyl)piperidine in the FMOC/Polyamine Approach to Rapid Peptide Synthesis," *J. Org. Chem.* 55(5):1673-1675 (Mar. 1990).

Chandy et al. "The Development of Porous Alginate/Elastin/PEG Composite Matrix for Cardiovascular Engineering," *Journal of Biomaterials Applications*, vol. 17 (Apr. 2003), pp. 287-301.

Corbett, S. et al. "Covalent Cross-linking of Fibronectin to Fibrin is Required for Maximal Cell Adhesion to a Fibronectin-Fibrin Matrix," *The Journal of Biological Chemistry*, 272(40):24999-25005 (Oct. 3, 1997).

Creemers, E. et al. "Matrix Metalloproteinase Inhibition After Myocardial Infarction: A New Approach to Prevent Heart Failure?" *Circ. Res.* vol. 89:201-210 (2001).

Crivello, et al. "Synthesis and Photoinitiated Cationic Polymerization of Monomers with the Silsesquioxane Core," *J Polym Science: Part A: Polymer Chemistry* 35:407-425 (1997).

Davis, M.E. et al., "Injectable Self-Assembling Peptide Nanofibers Create Intramyocardial Microenvironments for Endothelial Cells" *Circulation* 111:442-450 (Feb. 2005).

Desai, M. et al. "Polymer bound EDC (P-EDC): A convenient reagent for formation of an amide bond," *Tetrahedron Letters* 34(48):7685-7688 (Nov. 1993), Abstract downloaded from the Internet at: http://www.sciencedirect.com, 1 page.

Dinbergs et al. "Cellular Response to Transforming Growth Factor-β1 and Basic Fibroblast Growth Factor Depends on Release Kinetics & Extracellular Matrix Interactions," *J. Bio Chem* 271(47):29822-29829 (Nov. 22, 1996).

Edelman, E.R. et al. "Controlled & Modulated Release of Basic Fibroblast Growth Factor," *Biomaterials* vol. 12 (Sep. 1991), pp. 619-626.

Etzion, Sharon et al. "Influence of Embryonic Cardiomyocyte Transplantation on the Progression of Heart Failure in a Rat Model of Extensive Myocardial Infarction," *J. Mol. Cell Cardiol.* 33:1321-1330 (May 2001).

Ferrara, N. "Role of Vascular Endothelial Growth Factor in the Regulation of Angiogenesis," *Kidney International* 56(3):794-814 (1999), Abstract downloaded from the Internet at: http://www.nature.com/ki/journal/v56/n3/abs/4490967a.html, 1 page.

Fuchs, S. et al. "Catheter-Based Autologous Bone Marrow Myocardial Injection in No-Option Patients with Advanced Coronary Artery Disease," *J. Am. Coll. Cardiol.* 41(10):1721-1724 (2003).

Fukumoto, S. et al. "Protein Kinase C δ Inhibits the Proliferation of Vascular Smooth Muscle Cells by Suppressing $G_1$ Cyclin Expression," The Journal of Biological Chemistry 272(21):13816-13822 (May 1997).

Giordano, F. et al. "Angiogenesis: The Role of the Microenvironment in Flipping the Switch," *Current Opinion in Genetics and Development* (2001), 11:35-40.

Gossler, et al. "Transgenesis by means of blastocyst-derived embryonic stem cell lines," *Proc. Natl. Acad. Sci. USA*, 83:9065-9069 (Dec. 1986).

Grafe, T.H., "Nanofiber Webs from Electrospinning" Presented at the *Nonwovens in Filtration—Fifth International Conference*, Stuttgart, Germany, Mar. 2003, pp. 1-5.

Gref, R. et al. "Biodegradable Long-Circulating Polymeric Nanospheres," *Science* 263(5153):1600-1603 (Mar. 1994), Abstract downloaded from the Internet at: http://www.sciencemag.org/cgi/content/abstract/263/5153/1600, 1 page.

Grund, F. et al. "Microembolization in Pigs: Effects on Coronary Blood Flow and Myocardial Ischemic Tolerance," *Am J. Physiol.* 277 (*Heart Circ. Physiol. 46*):H533-H542 (1999).

Gupta et al: "Changes in Passive Mechanical Stiffness of Myocardial Tissue with Aneurysm Formation," *Circulation*, 89(5):2315-2326 (May 1994).

Hashimoto, T. et al. "Development of Alginate Wound Dressings Linked with Hybrid Peptides Derived from Laminin and Elastin," *Biomaterials* 25 (2004), pp. 1407-1414.

Heeschen, C. et al. "Nicotine Stimulates Tumor Angiogenesis," *American College of Cardiology* 37(2) Supplement A, pp. 1A-648A (Feb. 2001), Abstract downloaded from the Internet at: http://24.132.160.238/ciw-01acc/abstract_search_author.cfm?SearchName=Heeschen, 1 page.

Helisch, A. et al. "Angiogenesis and Arteriogenesis—Not yet for prescription," Neue Diagnostische Und Therap. Verfahren, *Z. Kardiol.* 89:239-244 Steinkopff Verlag (2000).

Hendel, R.C. et al. "Effect of Intracoronary Recombinant Human Vascular Endothelial Growth Factor on Myocardial Perfusion: Evidence for a Dose-Dependent Effect," *Circulation* 101:118-121 (2000).

Henry, R.R. et al. "Insulin Action and Glucose Metabolism in Nondiabetic Control and NIDDM Subjects. Comparison Using Human Skeletal Muscle Cell Cultures" Diabetes, 44(8):936-946 (1995), Abstract downloaded from the Internet at: http://diabetes.diabetesjournals.org/cgi/content/abstract/44/8/936, 1 page.

Holland, N.B. et al. "Biomimetic Engineering of Non-Adhesive glycocalyx-like Surfaces Using Oligosaccharide Surfactant Polymers," *Nature* 392:799-801 (Apr. 1998), Abstract downloaded from the Internet at: http://www.nature.com, 1 page.

Hovinen, J. et al. "Synthesis of 3'-functionalized oligonucleotides on a single solid support," *Tetrahedron Letters* 34(50):8169-8172 (Dec. 1993), Abstract downloaded from the Internet at: http://www.sciencedirect.com, 1 page.

(56) References Cited

OTHER PUBLICATIONS

Huang, K. et al. "Synthesis and Characterization of Self-Assembling Block Copolymers Containing Bioadhesive End Groups," *Biomacromolecules* (2002), 3(2):397-406.

Hutcheson, K. et al. "Comparison of Benefits on Myocardial Performance of Cellular Cardiomyoplasty with Skeletal Myoblasts and Fibroblasts," *Cell Transplantation* (2000), 9(3):359-368.

Indik, Z.. et al. "Production of Recombinant Human Tropoelastin: Characterization and Demonstration of Immunologic and Chemotactic Activity," *Arch. Biochem. Biophys.* 280(1):80-86 (Jul. 1990), Abstract downloaded from the Internet at: http://www.ncbi.nlm.nih.gov/entrez/query.fcgi?cmd=Retrieve&db=PubMed, 1 page.

Iskandrian, A.S. et al. "Nuclear Cardiac Imaging: Principles and Applications," second edition, F.A. Davis Co., Philadelphia (1996), cover page, title page and TOC (5 pages total).

Isner, J.M. "Vascular Endothelial Growth Factor: Gene Therapy and Therapeutic Angiogenesis" *Am. J. Cardiol.* Nov. 19, 1998; 82(10A): 63S-64S.

Ito, W. D. et al. "Monocyte Chemotactic Protein-1 Increases Collateral and Peripheral Conductance After Femoral Artery Occlusion," *Circulation Research*, 80(6):829-837, (Jun. 1997).

Johnson, O.L. et al. "The Stabilization & Encapsulation of Human Growth Hormone into Biodegradable Microspheres," *Pharmaceutical Research*, 14(6):730-735 (1997).

Jonasson, P. et al. "Denatured states of human carbonic anhydrase II: an NMR study of hydrogen/deuterium exchange at tryptophan-indole-$H_n$ sites," *FEBS Letters* 445 (1999), pp. 361-365.

Källtorp, M. et al. "Inflammatory Cell Recruitment, Distribution, and Chemiluminescence Response at IgG Precoated- and Thiol Functionalized Gold Surfaces," *J. Biomed. Mater. Res.*, 47:251-259 (1999).

Kawai, K. et al. "Accelerated Tissue Regeneration Through Incorporation of Basic Fibroblast Growth Factor-Impregnated Gelatin Microspheres into Artificial Dermis," *Biomaterials* 21 (2000), pp. 489-499.

Kawasuji, M. et al. "Therapeutic Angiogenesis with Intramyocardial Administration of Basic Fibroblast Growth Factor," *Ann Thorac Surg* 69:1155-1161 (2000), Abstract downloaded from the Internet at: http://ats.ctsnetjournals.org/cgi/content/abstract/69/4/1155, 2 pages.

Kelley et al. "Restraining Infarct Expansion Preserves Left Ventricular Geometry and Function After Acute Anteroapical Infarction," Circulation (1999), 99:135-142.

Kim, D. et al. "Glow Discharge Plasma Deposition (GDPD) Technique for the Local Controlled Delivery of Hirudin from Biomaterials," *Pharmaceutical Research* (1998), 15( 5):783-786.

Kinart et al. "Electrochemical Studies of 2-hydroxy-3-(3,4-dimethyl-9-oxo-9H-thioxanthen-2-yloxy)N,N,N-trimethyl-1-propanium chloride," *J. Electroanal. Chem* 294 (1990), pp. 293-297.

Kipshidze, N. et al. "Therapeutic Angiogenesis for Critical Limb Ischemia to Limit or Avoid Amputation," *The Journal of Invasive Cardiology* 11(1):25-28, (Jan. 1999).

Klein, S. et al. "Fibroblast Growth Factors as Angiogenesis Factors: New Insights Into Their Mechanism of Action," in *Regulation of Angiogenesis*, I.D. Goldberg and E.M. Rosen (eds.), 1997; 79:159-192.

Klugherz, B. et al. "Gene Delivery From a DNA Controlled-Release Stent in Porcine Coronary Arteries," *Nature Biotechnology* 18:1181-1184, (Nov. 2000).

Kohilas, K. et al. "Effect of Prosthetic Titanium Wear Debris on Mitogen-Induced Monocyte and Lymphoid Activation," *J. Biomed Mater Res.* 47:95-103, (Apr. 1999).

Kwok, Connie et al. "Design of Infection-Resistant Antibiotic-Releasing Polymers: I. Fabrication and Formulation," *Journal of Controlled Release* 62 (1999), pp. 289-299.

Laboratory of Liposome Research. "Liposomes: General Properties," downloaded from the Internet on Feb. 9, 2006 at: http://www.unizh.ch/onkwww/lipos.htm, 5 pages.

Laham, R.J., "Intrapericardial Delivery of Fibroblast Growth Factor-2 Induces Neovascularization in a Porcine Model of Chronic Myocardial Ischemia," *J. Pharmacol Exper Therap* 292(2):795-802, (2000).

Leor, J. et al. "Bioengineered Cardiac Grafts—A New Approach to Repair the Infarcted Myocardium?" *Circulation* (2000); 102[suppl III] III-56-III-61.

Leor, J. et al. Gene Transfer and Cell Transplant: An Experimental Approach to Repair a 'Broken Heart', *Cardiovascular Research* 35 (1997), pp. 431-441.

Leroux, J.C. et al. "An Investigation on the Role of Plasma and Serum Opsonins on the Internalization of Biodegradable poly(D,L-lactic acid) Nanoparticles by Human Monocytes," *Life Sci.* 57(7):695-703 (1995), Abstract downloaded from the Internet at: http://www.ncbi.nlm.nih.gov/entrez/query.fcgi?cmd=Retrieve&db=pubmed, 1 page.

Lewin, Benjamin. "Repressor is Controlled by a Small Molecule Induce", *Genes VII*, Oxford University Press, 7th ed., pp. 277-280, (2000).

Li, J. et al. "PR39, A Peptide Regulator of Angiogenesis," *Nature Medicine* 6(1):49-55, (Jan. 2000).

Li, W.W. et al. "Lessons to be Learned from Clinical Trials of Angiogenesis Modulators in Ischemic Diseases," Chapter 33, in Rubanyi, G. (ed). *Angiogenesis in Health & Disease: Basic Mechanisms and Clinical Applications*, Marcel Dekker, Inc. New York (2000).

Li, Y.Y. et al. "Differential Expression of Tissue Inhibitors of Metalloproteinases in the Failing Human Heart," *Circulation* 98(17):1728-1734, (1998).

Lindsey, M. et al. "Selective Matrix Metalloproteinase Inhibition Reduces Left Ventricular Remodeling but does not Inhibit Angiogenesis after Myocardial Infarction," *Circulation* 105(6):753-758, (2002).

Long, D.M. et al. "Self-Cleaving Catalytic RNA," *FASEB Journal*, 7:25-30, (1993).

Lopez, J. J. et al. "Angiogenic Potential of Perivascularly Delivered aFGF in a Porcine Model of Chronic Myocardial Ischemia," *Am. J. Physiol.* 274 (*Heart Circ. Physiol.* 43):H930-H936, (1998).

Lopez, J. J. et al. "VEGF Administration in Chronic Myocardial Ischemia in Pigs," *Cardiovasc Res.* 40(2):272-281 (1998), Abstract downloaded from the Internet at: http://www.ncbi.nlm.nih.gov/entrez/query.fcgi?cmd=Retrieve&db=pubmed, 1 page.

Lu, L. et al. "Biodegradable Polymer Scaffolds for Cartilage Tissue Engineering," in *Clinical Orthopaedics and Related Research*, Carl T. Brighton (ed.). No. 391S, pp. S251-S270, (2001).

Luo, Y. et al. "Cross-linked Hyaluronic Acid Hydrogel Films: New Biomaterials for Drug Delivery," *Journal of Controlled Release*, 69:169-184, (2000).

Lyman, M.D. et al. "Characterization of the Formation of Interfacially Photopolymerized Thin Hydrogels in Contact with Arterial Tissue," *Biomaterials*, 17(3):359-64, (1996).

Mansour, S. et al. "Disruption of the proto-oncogene *int-2* in mouse embryo-derived stem cells: a general strategy for targeting mutations to non-selectable genes," *Nature*, 336:348-352, (1988).

Martin, S.L. et al. "Total Synthesis and Expression in *Escherichia coli* of a Gene Encoding Human Tropoelastin," *Gene* (1995), Abstract, 1 page.

McDevitt, T. et al. "In vitro Generation of Differentiated Cardiac Myofibers on Micropatterned Laminin Surfaces," *J. Biomed Mater Res.* 60:472-479, (2002).

Narmoneva, D.A. et al. "Self-assembling short oligopeptides and the promotion of angiogenesis," *Biomaterials* 26 (2005) 4837-4846.

Nguyen, Kytai T. et al. "Photopolymerizable Hydrogels for Tissue Engineering Applications," *Biomaterials* 23:4307-4314, (2002).

Nikolic, S.D. et al. "New Angiogenic Implant Therapy Improves Function of the Ischemic Left Venticle," supplement to *Circulation. Abstracts From Scientific Sessions 2000*, 102(18)II-689, Abstract 3331 (Oct. 2000).

Nitinol Technical Information, "NiTi Smart Sheets," downloaded from the Internet on Dec. 10, 2002 at: http://www.sma-inc.com/information.html, 1 page.

Ohyanagi, H. et al. "Kinetic Studies of Oxygen and Carbon Dioxide Transport into or from Perfluorochemical Particles," *Proc. ISAO* vol. 1 (*Artificial Organs* vol. 2 (Suppl.)), pp. 90-92 (1977).

(56) References Cited

OTHER PUBLICATIONS

Ozbas, B. et al. "Salt-Triggered Peptide Folding and Consequent Self-Assembly into Hydrogels with Tunable Modulus," *Macromolecules* 37(19):7331-7337, (2004).

Ozbas-Turan, Suna. "Controlled Release of Interleukin-2 from Chitosan Microspheres," *Journal of Pharmaceutical Sciences* 91(5):1245-1251, (May 2002).

Palmiter R. et al. "Germ-Line Transformation of Mice," *Ann. Rev. Genet.* 20:465-499, (1986).

Patrick, C.R. "Mixing and Solution Properties of Organofluorine Compounds," Chapter 10, in Preparation, Properties and Industrial Applications of Organofluorine Compounds, R.E. Banks (ed.), 1st edition, pp. 323-342, Ellis-Horwood Ltd., Chichester:England (1982).

PCT Invitation to Pay Additional Fees for International Appln No. PCT/US03/18360, mailed Nov. 4, 2003 (3 pgs).

PCT International Search Report for International Appln No. PCT/US03/18360, mailed Jan. 28, 2004 (7 pgs).

PCT International Search Report for International Appln. No. PCT/US03/30464, mailed Feb. 9, 2004 (5 pages).

PCT International Preliminary Report on Patentability for International Appln. No. PCT/US2004/011356, mailed Nov. 3, 2005 (6 pgs).

PCT International Search Report and Written Opinion for International Appln No. PCT/US2005/045627, mailed Oct. 13, 2006 (15 pgs).

Peattie, R.A. et al. "Stimulation of In Vivo Angiogenesis by Cytokine-Loaded Hyaluronic Acid Hydrogel Implants," *Biomaterials* (Jun. 2004) 25(14), Abstract downloaded from: www.sciencedirect.com, 2 pages.

Penta, K. et al. "Dell Induces Integrin Signaling and Angiogenesis by Ligation of $\alpha V\beta 3$," *J. Biolog. Chem.* 274(16):11101-11109, (Apr. 1999).

Perin, E.C. et al. "Transendocardial, Autologous Bone Marrow Cell Transplantation for Severe, Chronic, Ischemic Heart Failure," *Circulation* (2003), 1 page.

Pouzet, B. et al. "Is Skeletal Myoblast Transplantation Clinically Relevant in the Era of Angiotensin-Converting Enzyme Inhibitors?" *Circulation* 104[suppl I]:I-223-I-228, (Sep. 2001).

Prather et al. "Nuclear Transplantation in Early Pig Embryos," *Biol. Reprod.* 41:414-418, (1989).

Quellec, P. et al. "Protein Encapsulation Within Polyethylene Glycol-coated Nanospheres. I. Physicochemical Characterization," *J. Biomed. Mater. Res.* 42(1), (1998) Abstract, 1 page.

Ramirez-Solis, R. et al. "Gene Targeting in Embryonic Stem Cells," *Methods in Enzymology*, 225:855-878, (1993).

Rowley, J. et al. "Alginate Hydrogels as Synthetic Extracellular Matrix Materials," *Biomaterials* 20:45-53, (1999).

Sawhney, A.S. et al. "Bioerodible Hydrogels Based on Photopolymerized Poly(ethylene glycol)-co-poly(a-hydroxy acid) Diacrylate Macromers," *Macromolecules* 26(4):581-587, (1993).

Sbaa-Ketata, E. et al. "Hyaluronan-Derived Oligosaccharides Enhance SDF-1-Dependent Chemotactic Effect on Peripheral Blood Hematopoietic CD34$^+$ Cells," *Stem Cells* (2002), 20(6):585-587, "Letter to the Editor" downloaded from the Internet at: http://stemcells.alphamedpress.org/cgi/content/full/20/6/585, 5 pages.

Segura, T. et al. "[216c]-DNA Delivery From Hyaluronic Acid/Collagen Hydrogels," AIchE Technical Program Paper Detail, *American Institute of Chemical Engineers* (ALCHE Annual Meeting 2003), Abstract downloaded from the Internet at: http://www.aiche.org/cofnerences/techprogram/paperdetail.asp?PaperID=1465 &DSN=annual, 2 pages.

Segura, T. et al. "Crosslinked Hyaluronic Acid Hydrogels: A Strategy to Functionalize and Pattern," *Biomaterials* 26:359-371, (2005).

Segura, T. et al. "Substrate-Mediated DNA Delivery: Role of the Cationic Polymer Structure and Extent of Modification," *Journal of Controlled Release* 93:69-84, (2003).

Segura, T. et al. "Surface-Tethered DNA Complexes for Enhanced Gene Delivery," *Bioconjugate Chem* 13(3):621-629, (2002).

Shibasaki, F. et al. "Suppression of Signalling Through Transcription Factor NF-AT by Interactions Between Calcineurin and Bcl-2," *Nature* (1997) 386(6626), Abstract downloaded from the Internet at: http://www.ncbi.nlm.nih.gov/entrez/query.fcgi?CMD=Text &DB=pubmed, 1 page.

Shin, H. et al. "Attachment, Proliferation, and Migration of Marrow Stromal Osteoblasts Cultured on Biomimetic Hydrogels Modified with an Osteopontin-Derived Peptide," *Biomaterials* 25:895-906, (2004).

Shin, H. et al. "In Vivo Bone & Soft Tissue Response to Injectable, Biodegradable oligo(poly(ethylene glycol) fumerate) Hydrogels," *Biomaterials* 24:3201-3211, (Mar. 2003).

Shu, et al. "Disulfide-crosslinked hyaluronan-gelatin hydrogel films: a covalent mimic of the extracellular matrix for in vitro cell growth," *Biomaterials* (Sep. 2003) 24(21)3825-3834, Abstract downloaded from the Internet at: http://www.sciencedirect.com, 1 page.

Simons, M. et al. "Clinical Trials in Coronary Angiogenesis: Issues, Problems, Consensus—An Expert Panel Summary," *Circulation* 102:e73-e86, (Sep. 2000), pp. 1-14.

Spenlehauer, G. et al. "In vitro and in vivo Degradation of poly (D,L lactide/glycolide) Type Microspheres Made by Solvent Evaporation Method," *Biomaterials* 10:557-563, (Oct. 1989).

Spinale, Francis G. "Matrix Metalloproteinases—Regulation and Dysregulation in the Failing Heart," *Circ. Res.* 90:520-530, (2002).

Springer, M. et al. "Angiogenesis Monitored by Perfusion with a Space-Filling Microbead Suspension," *Mol. Ther.* (2000) 1(1):82-87, Abstract downloaded from the Internet at: http://www.ncbi.nlm.nih.gov/entrez/query.fcgi?cmd=Retrieve&db=PubMed, 1 page.

Storm, G. et al. "Surface Modification of Nanoparticles to Oppose Uptake by the Mononuclear Phagocyte System," *Advanced Drug Delivery Reviews* (Oct. 1995), 17(1):31-48, Abstract downloaded from the Internet at: http://www.sciencedirect.com, 1 page.

Strauer, B. et al. "Repair of Infarcted Myocardium by Autologous Intracoronary Mononuclear Bone Marrow Cell Transplantation in Humans," *Circulation* 106:1913-1918, (2002).

Tybulewicz, V. et al. "Neonatal lethality and lymphopenia in mice with a homozygous disruption of the c-*abl* proto-oncogene," *Cell* (Jun. 1991), 65(7):1153-1163, Abstract downloaded from the Internet at: http://www.sciencedirect.com, 2 pages.

Unger, E.F. et al. "Effects of a Single Intracoronary Injection of Basic Fibroblast Growth Factor in Stable angina Pectoris" *Am. J. Cardiol* 85(12):1414-1419 (Jun. 2000), Abstract downloaded from the Internet at: http://www.sciencedirect.com, 2 pages.

van der Giessen, W.J. et al. "Marked Inflammatory Sequelae to Implantation of Biodegradable and Nonbiodegradable Polymers in Porcine Coronary Arteries," *Circulation* 94(7):1690-1697 (Oct. 1996).

van Luyn, M.J.A. et al. "Cardiac Tissue Engineering: Characteristics of In Unison Contracting Two- and Three-Dimensional Neonatal Rat Ventricle Cell (Co)-Cultures," *Biomaterials* 23:4793-4801, (2002).

Vercruysse, K.P. et al. "Synthesis and in Vitro Degradation of New Polyvalent Hydrazide Cross-Linked Hydrogels of Hyaluronic Acid," *Bioconjugate Chem* 8(5):686-694 (1997), Abstract downloaded from the Internet at: http://pubs.acs.org/cgi-bin/abstract.cgi/bcches/1997/8/i05/abs/bc9701095.html, 1 page.

Visscher, G.E. et al. "Tissue Response to Biodegradable Injectable Microcapsules," *Journal of Biomaterials Applications* 2 (Jul. 1987), pp. 118-119.

Vlodaysky, I. et al. "Extracellular Matrix-resident Basic Fibroblast Growth Factor: Implication for the Control of Angiogenesis," *J. Cell Biochem*, 45(2):167-176 (Feb. 1991), Abstract downloaded from the Internet at: http://www.ncbi.nlm.nih.gov/entrez/query.fcgi?cmd=Retrieve&db=PubMed, 1 page.

Wasielewski, S. "Ischämische Erkrankungen, Gefäßneubildung anregen" *Deutsche Apotheker Zeitung* (Jan. 2000), 140(3):232-233, Stuttgart (DE).

Witzenbichler, B., et al. "Vascular Endothelial Growth Factor-C (VEGF-C/VEGF-2) Promotes Angiogenesis in the Setting of Tissue Ischemia" *Am Pathol.* 153(2):381-394, (Aug. 1998).

Yamamoto, N. et al. "Histologic Evidence that Basic Fibroblast Growth Factor Enhances the Angiogenic Effects of Transmyocardial Laser Revascularization," *Basic Res. Cardiol.* 95(1):55-63, (Feb. 2000).

(56) References Cited

OTHER PUBLICATIONS

Zervas, L. et al. "On Cysteine and Cystine Peptides. II. S-Acylcysteines in Peptide Synthesis," *J. Am. Chem. Soc.* 85(9):1337-1341, (May 1963).
Zheng, W. et al. "Mechanisms of coronary angiogenesis in response to stretch: role of VEGF and TGF-beta," *Am J Physiol Heart Circ Physiol.* 280(2):H909-H917, (Feb. 2001).
Zimmermann, W. et al. "Engineered Heart Tissue for Regeneration of Diseased Hearts," Biomaterials 25:1639-1647, (2004).
Abbott Cardiovascular Systems, Non final office action dated Aug. 13, 2010 for U.S. Appl. No. 11/447,340.
Abbott Cardiovascular Systems, Final office action mailed Sep. 27, 2010 for U.S. Appl. No. 10/792,960.
Abbott Cardiovascular Systems, Final Office Action mailed Sep. 27, 2010 for U.S. Appl. No. 12/016,180.
Abbott Cardiovascular Systems, Final Office Action mailed Nov. 22, 2010 for U.S. Appl. No. 10/781,984, 13 pages.
Abbott Cardiovascular Systems, Non-final Office Action mailed Nov. 24, 2010, for U.S. Appl. No. 12/013,286, 11 pages.
Abbott Cardiovascular Systems, Non final Office Action mailed Dec. 8, 2010 for U.S. Appl. No. 11/566,643, 17 pages.
Abbott Cardiovascular Systems, Non final Office Action mailed Dec. 10, 2010 for U.S. Appl. No. 11/938,752, 32 pages.
Abbott Cardiovascular Systems, Non final Office Action mailed Dec. 17, 2010 for U.S. Appl. No. 11/933,922, 23 pages.
Abbott Cardiovascular Systems, website For HEALON (R) OVD, copyright (2010), accessed Dec. 15, 2010, URL: <http://abbottmedicaloptics.com/products/cataract/ovds/healon-viscoelastic>, (2010), 2 pages.
Abbott Cardiovascular Systems, *Product Information Sheet for HEALON (R), from Abbott Medical Optics*, (2005), 1 page.
Abbott Cardiovascular Systems, Japanese Office Action dated Dec. 8, 2010 for Japanese Patent App No. 2006-509975., 6 pages.
Abbott Cardiovascular Systems, Non final office action mailed Feb. 8, 2011 for U.S. Appl. No. 10/792,960.
Haynesworth, Stephen E., et al., "Platelet Effects on Human Mesenchymal Stem Cells", Abstract, presented at Orthopaedic Research Society 48th Annual Meeting, Dallas, TX, (Feb. 10-13, 2010), 2 pages.
Abbott Cardiovascular Systems Inc, PCT Search Report and Written Opinion dated Aug. 26, 2008 for PCT/US2007/016433.
Abbott Cardiovascular Systems Inc, PCT Search Report and Written Opinion dated Jul. 31, 2008 for PCT/US2007/024158.
Abbott Cardiovascular Systems Inc, PCT International Preliminary Report on Patentability and Written Opinion dated Dec. 24, 2008 for PCT/US2007/013181, 11 pages.
Abbott Cardiovascular Systems Inc, PCT International Search Report and Written Opinion mailed Feb. 10, 2009 for PCT/US2007/023419, 17 pages.
Advanced Cardiovascular Systems, Inc. et al., PCT International Preliminary Report on Patentability dated Jun. 19, 2007 for PCT Appln. No. PCT/US2005/045627.
Advanced Cardiovascular Systems, Inc., PCT Search Report and Written Opinion dated Nov. 24, 2004 for PCT Appln. No. PCT/US2004/011356, 12 pages.
De Rosa, et al., "Biodegradable Microparticles for the Controlled Delivery of Oligonucleotides", International Journal of Pharmaceutics, 242, Aug. 21, 2002, pp. 225-228.
Friedman, Paul M., et al., "Safety Data of Injectable Nonanimal Stabilized Hyaluronic Acid Gel for Soft Tissue Augmentation," Dermatologic Surgery, 2002, vol. 28, pp. 491-494.
Hanawa, T., et al., "New oral dosage form for elderly patients: preparation and characterization of silk fibroin gel", Chemical and Pharmaceutical Bulletin, Pharmaceutical Society of Japan, Tokyo, vol. 43, No. 2, Jan. 1995, pp. 284-288.
Haugland, et al., "Dialkylcarbocyanine and Dialkylaminostryryl Probes", Handbook of Fluorescent Probes and Research Products, Molecular Probes, Inc., 2002, pp. 530-534.
Haugland, et al., "Membrane-permeant reactive tracers", Handbook of Fluorescent Probes and Research Products, Molecular Probes, Inc., 2002, pp. 458-553.
Hoffman, "Hydrogels for Biomedical Applications", Advanced Drug Delivery Reviews, vol. 43, 2002, pp. 3-12.
Horan, R.L., et al., "In Vitro Degradation of Silk Fibroin", Biomaterials, vol. 26, 2004, pp. 3385-3393.
Kaplan, D.L., et al., "Spiderless Spider Webs", Nature Biotechnology, vol. 20, 2002, pp. 239-240.
Kelly, E. B., "Advances in Mammalian and Stem Cell Cloning", Genetic Engineering News, vol. 23, No. 7, Apr. 1, 2003, pp. 17-18 & 68.
Khademhosseini, et al., "Microscale Technologies for Tissue Engineering and Biology", PNAS, vol. 103, No. 8, Feb. 21, 2006, pp. 2480-2487.
Kim, Ung-Jin, et al., "Structure and Properties of Silk Hydrogels", Biomacromolecules, vol. 5(3), 2004, pp. 786-792.
Kweon, H. Y., et al., "Preparation of semi-interpenetrating polymer networks composed of silk fibroin and poly(ethyleneglycol) macromer", Journal of Applied Polymer Science, John Wiley and Sons Inc., New York, NY, vol. 80, Jan. 2001, pp. 1848-1853.
Leibovich, S. J., et al., "Macrophage-Induced Angiogenesis is Mediated by Tumour Necrosis Factor-α", Nature, vol. 329, Oct. 15, 1987, pp. 630-632.
Li, et al., "Cell Therapy to Repair Broken Hearts", Can. J. Cardiol., vol. 14, No. 5, (May 1998), pp. 735-744.
Meinel, L., et al., "The Inflammatory Responses to Silk Films In Vitro and In Vivo", Biomaterials, vol. 26, 2005, pp. 147-155.
Nazarov, R., et al., "Porous 3-D Scaffolds from Regenerated Silk Fibroin", Biomacromolecules, vol. 5(3), 2004, pp. 718-726.
Nikolic, Serjan D., et al., "Novel means to improve coronary blood flow", Clinical Science, Abstracts from Scientific Sessions, 2000, pp. II-689.
Nose, et al., "A novel cadherin cell adhesion molecule: its expression patterns associated with implantation and organogenesis of mouse embryos", Journal of Cell Biology, vol. 103 (No. 6, Pt. 2), The Rockefeller University Press, Dec. 1986, pp. 2649-2658.
Wang, M., et al., "Mechanical Properties of Electrospun Silk Fibers", Macromolecules, vol. 37(18), 2004, pp. 6856-6864.
Wilensky, R., et al., "Direct intraarterial wall injection of microparticles via a catheter: a potential durg delivery strategy following angioplasty", American Heart Journal, 122, 1991, pp. 1136.
Abbott Cardiovascular Systems, Office Action mailed Apr. 6, 2009 for U.S. Appl. No. 11/447,340.
Abbott Cardiovascular Systems, Office Action mailed Mar. 30, 2009 for U.S. Appl. No. 10/792,960.
Abbott Cardiovascular Systems, Office Action mailed Apr. 13, 2009 for U.S. Appl. No. 11/566,643.
Abbott Cardiovascular Systems, Office Action mailed Apr. 29, 2009 for U.S. Appl. No. 12/013,286.
Elbert, D. L., et al., "Protein delivery from materials formed by self-selective conjugate addition reactions", Journal of Controlled Release, 76, (2001), 11-25.
Abbott Cardiovascular Systems, Final Office Action mailed Apr. 15, 2011 for U.S. Appl. No. 10/414,602.
Advanced Cardiovascular Systems, Extended European search report dated Apr. 21, 2011 for EP Application No. 10186186.2.
Advanced Cardiovascular Systems, Extended EP Search Report dated May 20, 2011 for EP Application No. 10186197.9.
Chung, Y. , et al., "Sol-gel transition temperature of PLGA-g-PEG aqueous solutions", Biomacromolecules, vol. 3, No. 3, (May 2002), 511-516.
Abbott Cardiovascular Systems Inc., Non-Final Office Action dated May 12, 2009 for U.S. Appl. No. 11/496,824.
Abbott Cardiovascular Systems Inc., Non-Final Office Action dated Mar. 13, 2009 for U.S. Appl. No. 10/414,602.
Staatz, WD , et al., "Identification of a tetrapeptide recognition sequence for the alpha 2 beta 1 integrin in collagen", Journal of Biological Chemistry, 1991, 266(12), pp. 7363-7367.
Abbott Cardiovascular Systems, International Preliminary Report on Patentability dated Jul. 30, 2009 for PCT/US2008/051505.
Abbott Cardiovascular Systems, Final office action dated Nov. 12, 2009 for U.S. Appl. No. 12/013,286.

(56) References Cited

OTHER PUBLICATIONS

Abbott Cardiovascular Systems, Final office action dated Nov. 25, 2009 for U.S. Appl. No. 11/566,643.
Abbott Cardiovascular Systems, Non final office action dated Dec. 9, 2009 for U.S. Appl. No. 10/781,984.
Abbott Cardiovascular Systems, Examination Report dated Jan. 13, 2010 for EP Application No. 07795729.8.
Abbott Cardiovascular Systems, Non final office action dated Feb. 5, 2010 for U.S. Appl. No. 11/447,340.
Abbott Cardiovascular Systems, Final Office Action dated Jan. 29, 2010 for U.S. Appl. No. 10/792,960.
Abbott Cardiovascular Systems, Examination Report dated Jan. 15, 2010 for EP 08727952.7.
Abbott Cardiovascular Systems, Examination Report dated Feb. 5, 2010 for EP 07810637.4.
Abbott Cardiovascular Systems, International search report and written opinion dated Jun. 18, 2009 for PCT/US2008/051505.
Abbott Cardiovascular Systems, Non final office action dated Jul. 9, 2009 for U.S. Appl. No. 11/561,328.
Abbott Cardiovascular Systems, Non final office action dated Apr. 14, 2010 for U.S. Appl. No. 12/016,180.
Abbott Cardiovascular Systems, Final office action dated Apr. 22, 2010 for U.S. Appl. No. 10/414,602.
Abbott Cardiovascular Systems, Non final office action dated Apr. 29, 2010 for U.S. Appl. No. 10/792,960.
Abbott Cardiovascular Systems, Non-Final Office Action dated Jun. 4, 2010 for U.S. Appl. No. 10/781,984.
Abbott Cardiovascular Systems, Final Office Action Mailed Jun. 11, 2010 for U.S. Appl. No. 11/561,328.
Hao, X , et al., "Angiogenic effects of sequential release of VEGF-A165 and PDGF-BB with alginate hydrogels after myocardial infarction", Cardiovascular Research, 75, (2007), 178-185.
Ritter, A. B., et al., "Elastic modulus, distensibility, and compliance (capacitance)", Biomedical Engineering Principles, Chapter 4, (2005), 187-191.
Zheng, Shu , et al., "In situ crosslinkable hyaluronan hydrogels for tissue engineering", Biomaterials, Elsevier Science Publishers, vol. 25, No. 7-8, (2004), 1339-1348.
Choi, et al., "Study on gelatin-containing artificial skin: I. Preparation and characteristics of novel gelatin-alginate sponge," Biomaterials, 1999, vol. 20, pp. 409-417.
Dong, et al., "Alginate/gelatin blend films and their properties for drug controlled release," Journal of Membrane Science, 2006, vol. 280, pp. 37-44.
Lutolf, et al., "Synthesis and Physicochemical Characterization of End-Linked Poly(ethylene glycol)-co-peptide Hydrogels Formed by Michael-Type Addition," Biomacromolecules, 2003, vol. 4, pp. 713-722.
Segura, et al., "DNA delivery from hyaluronic acid-collagen hydrogels via a substrate-mediated approach," Biomaterials, 2005, vol. 26, pp. 1575-1584.
Shu, et al., "In situ crosslinkable hyaluronan hydrogels for tissue engineering," Biomaterials, 2004, vol. 25, pp. 1339-1348.
PCT Search Report for PCT Appln No. PCT/US2006/014021, mailed Jan. 31, 2007 (11 pages).
PCT Search Report for PCT Appln No. PCT/US2007/013181, mailed Feb. 12, 2008 (17 pages).
PCT Search Report for PCT Appln No. PCT/US2007/003614, mailed Mar. 27, 2008 (18 pages).
Khademhosseini, et al., "Microscale Technologies for Tissue Engineering and Biology", PNAS, Feb. 21, 2006, vol. 103, No. 8, pp. 2480-2487.
Kelly, E.B., "Advances in Mammalian and Stem Cell Cloning", *Genetic Engineering News*, vol. 23, No. 7, Apr. 1, 2003, pp. 17-18 & 68.
Li, et al., "Cell Therapy to Repair Broken Hearts", *Can. J. Cardiol*, vol. 14, No. 5, May 1998, pp. 735-744.
Leibovich, S.J., et al., "Macrophage-Induced Angiogenesis is Mediated by Tumour Necrosis Factor-α.", *Nature*, vol. 329, Oct. 15, 1987, pp. 630-632.
De Rosa, et al., "Biodegradable Microparticles for the Controlled Delivery of Oligonucleotides", *International Journal of Pharmaceutics*, Aug. 21, 2002, 242: pp. 225-228.
Abbott Cardiovascular Systems, Non final office action mailed Nov. 8, 2011 for U.S. Appl. No. 10/792,960.
Abbott Cardiovascular Systems, Final Office Action mailed Jan. 5, 2012 for U.S. Appl. No. 11/361,920, 13 pages.
Abbott Cardiovascular Systems, Office Action mailed Jan. 17, 2012 for European Patent Application 08727952.7, 6 pages.
Abbott Cardiovascular Systems, Non-Final Office Action mailed Jan. 30, 2012 for U.S. Appl. No. 10/781,984, 10 pages.
Abbott Cardiovascular Systems, Final Office Action mailed Feb. 8, 2012 for Japanese application No. 2006-509975, 6 pages.
Abbott Cardiovascular Systems, Non-Final Office Action mailed Feb. 15, 2012 for U.S. Appl. No. 12/114,717, 16 pages.
Abbott Cardiovascular Systems, Final Office Action mailed Apr. 4, 2012 for U.S. Appl. No. 10/792,960, 13 pages.
Abbott Cardiovascular Systems, European Office Action mailed Apr. 11, 2012 for App No. 12155231.9, 9 pages.
Abbott Cardiovascular Systems, European Office Action mailed Apr. 10, 2012 for App No. 07810637.4, 6 pages.
Abbott Cardiovascular Systems, Non final office action mailed Jun. 7, 2011 for U.S. Appl. No. 11/447,340.
Abbott Cardiovascular Systems, Non final office action mailed Jul. 6, 2011 for U.S. Appl. No. 10/781,984.
Abbott Cardiovascular Systems, Final office action mailed Jun. 28, 2011 for U.S. Appl. No. 10/792,960.
Abbott Cardiovascular Systems, Final office action mailed Jul. 18, 2011 for U.S. Appl. No. 11/566,643.
Abbott Cardiovascular Systems, Final office action mailed Sep. 20, 2011 for U.S. Appl. No. 11/938,752.
Abbott Cardiovascular Systems, Final Office Action mailed Oct. 21, 2011 for U.S. Appl. No. 10/781,984, 10 pages.
Zheng, W., "Mechanisms of coronary angiogenesis in response to stretch; role of VEGF and TGF-Beta", AM J Physiol Heart Circ Physiol 280(2), (Feb. 2001), H909-H917.
Abbott Cardiovascular Systems, Non-Final Office Action dated Mar. 5, 2009 for U.S. Appl. No. 11/507,860.
Abbott Cardiovascular Systems, Non final office action dated Aug. 5, 2009 for U.S. Appl. No. 11/031,608.
Abbott Cardiovascular Systems, Final office action dated Mar. 29, 2010 for U.S. Appl. No. 11/031,608.
Abbott Cardiovascular Systems, Final Office Action Mailed Jul. 15, 2010, U.S. Appl. No. 11/507,860, 10 pages.
Abbott Cardiovascular Systems, European Search report for Application No. 12151788.2 mailed Apr. 18, 2012, 6 pages.
Abbott Cardiovascular Systems, Non-final Office Action mailed Jun. 26, 2012 for U.S. Appl. No. 12/632,612, 8 pages.
Abbott Cardiovascular Systems, Japanese Office Action dated Jun. 11, 2012 for Application No. 2010-162711.
Bull, S. , et al., "Self-Assembled Peptide Amphiphile Nanofibers Conjugated to MRI Contrast Agents", Nano Letters, vol. 5, No. 1, (Jan. 2005), 4 pages.
Csonka, E. , et al., "Interspecific Interaction of Aortic Endothelial and Smooth Muscle Cells", Acta Morphologica Hungarcia, vol. 35, No. 1-2, (1987), 31-35.
Griese, D. P., et al,, "Vascular gene delivery of anticoagulants by transplantation of retrovirally-transduced endothelial progenitor cells", Cardiovascular Research, vol. 58, (2003), 469-477.
Hartgerink, J. D., et al., "Peptide-amphiphile nanofibers: A versatile scaffold for the preparation of self-assembling materials", PNAS, vol. 99, No, 8, (Apr. 16, 2002), 5133-5138.
Hartgerink, J. D., et al., "Self-Assembly and Mineralization of Peptide-Amphiphile Nanofibers", Science, vol. 294, (Nov. 23, 2001), 1684-1688.
Li, B. , et al., "VEGF and PlGF promote adult vasculogenesis by enhancing EPC recruitment and vessel formation at the site of tumor neovascularization", The FASEB Journal, vol. 20, (2006), 1495-1497.
Seeger, J. M., et al., "Improved in vivo endothelialization of prosthetic grafts by surface modification with fibronectin", J Vasc Surg, vol. 8, No. 4, (Oct. 1988), 476-82 (Abstract only).

(56) References Cited

OTHER PUBLICATIONS

Urbich, C., et al., "Endothelial Progenitor Cells: Characterization and Role in Vascular Biology", Circulation Research, vol. 95, (2004), 343-353.
Abbott Cardiovascular Systems, Non-Final Office Action Sep. 11, 2012 for U.S. Appl. No. 10/792,960.
Abbott Cardiovascular Systems, Japanese office action dated Aug. 20, 2012 for JP 2009-537153.
Abbott Cardiovascular Systems, Non-Final Office Action dated Oct. 3, 2012 for U.S. Appl. No. 12/756,119.
Abbott Cardiovascular Systems, et al., Japanese Office Action dated Aug. 27, 2012 for JP 2009-522776.
Abbott Cardiovascular Systems, Final Office Action dated Nov. 8, 2012 for U.S. Appl. No. 12/114,717.
Abbott Cardiovascular Systems, Final Office Action mailed Nov. 7, 2012 for U.S. Appl. No. 10/781,984.
Davis, M E., et al., "Injectable Self-Assembling Peptide Nanofibers Create Intramyocardial Microenvironments for Endothelial Cells", Circulation, 111, (2005), 442-450.
Hao, X, et al., "Angiogenic Effects of Sequential release of VEGF-A 165 and PDGF-BB with Alginate Hydrogels After Myocardial Infarction", Cardiovascular Research, 75(1), (Apr. 6, 2007), 178-185.
Mogan, L., "Rationale of platelet gel to augment adaptive remodeling of the injured heart", J Extra Corpor Technol, 36(2), (Jun. 2004), 191-196.
Abbott Cardiovascular Systems, Final Office Action mailed Dec. 13, 2011 for U.S. Appl. No. 12/963,397.
Abbott Cardiovascular Systems, Non-final Office Action mailed Jun. 22, 2012 for U.S. Appl. No. 12/963,397.
Abbott Cardiovascular Systems, Restriction requirement mailed Jul. 3, 2012 for U.S. Appl. No. 13/472,324.
Abbott Cardiovascular Systems, Non-final Office Action mailed Aug. 28, 2012 for U.S. Appl. No. 13/472,324.
Abbott Cardiovascular Systems, Non-final Office Action mailed Aug. 30, 2012 for U.S. Appl. No. 13/472,328.
Abbott Cardiovascular Systems, Japanese Office Action dated Nov. 19, 2012 for Appln. No. 2009-539265.
Abbott Cardiovascular Systems, Japanese office action dated Oct. 9, 2012 for JP Appln. No. 2009-514330.
Abbott Cardiovascular Systems, Japanese Office Action mailed Dec. 17, 2012 for JP Appln. No. 2009-546553.
Abbott Cardiovascular Systems, Examination Report dated Feb. 20, 2013 for European Appln. No. 12151788.2, 4 pages.
Abbott Cardiovascular Systems, Non final office action dated Apr. 1, 2013 for U.S. Appl. No. 13/559,423.
Abbott Cardiovascular Systems, Non-Final Office Action dated Oct. 3, 2012 for U.S. Appl. No. 12/756,092.
Abbott Cardiovascular Systems, Final office action mailed Apr. 22, 2013 for U.S. Appl. No. 10/792,960.
Abbott Cardiovascular Systems, Japanese office action mailed Mar. 25, 2013 for JP 2009-539265.
Abbot Cardiovascular Systems, Non-final Office Action mailed Dec. 4, 2013 for U.S. Appl. No. 11/561,328.
Abbot Cardiovascular Systems, Non-final Office Action mailed Dec. 4, 2013 for U.S. Appl. No. 11/507,860.
Abbott Cardiovascular Systems, Notice of Allowance mailed Sep. 30, 2013 for U.S. Appl. No. 13/559,423.
Abbott Cardiovascular Systems, Notice of Allowance mailed Dec. 23, 2013 for U.S. Appl. No. 13/559,438.
Abbott Cardiovascular Systems, Japanese office action mailed Nov. 22, 2013 for JP 2009-539265, (10 pages).
Abbott Cardiovascular Systems, Final Office Action mailed Feb. 4, 2014 for U.S. Appl. No. 13/888,143.
Abbott Cardiovascular Systems, Final office action dated Jan. 18, 2013 for U.S. Appl. No. 12/963,397.
Abbott Cardiovascular Systems, Non final office action mailed May 31, 2013 for U.S. Appl. No. 13/559,438.
Abbott Cardiovascular Systems, Non final office action mailed Jul. 2, 2013 for U.S. Appl. No. 11/938,752.
Abbott Cardiovascular Systems, Non final office action dated Aug. 20, 2013 for U.S. Appl. No. 12/114,717.
Abbott Cardiovascular Systems, Non-Final Office Action mailed Oct. 16, 2013 for U.S. Appl. No. 13/468,956.
chemcas.org, MSDS 4-amino-2,2,6,6-tetramethlypiperidine-1-oxyl (4-amino-TEMPO) CAS No. 14691-88-4 at www.chemcas.org/drug/analytical/cas/14691-88-4-asp, (Sep. 2, 1997), 5 pages.

* cited by examiner

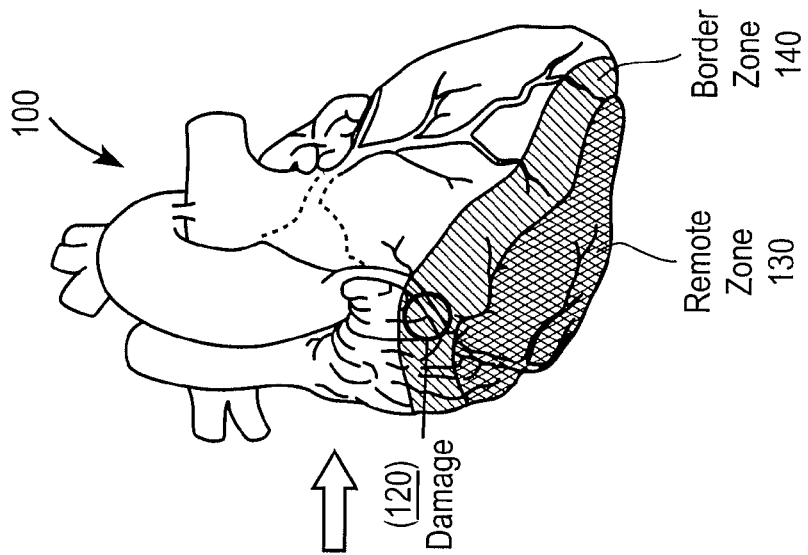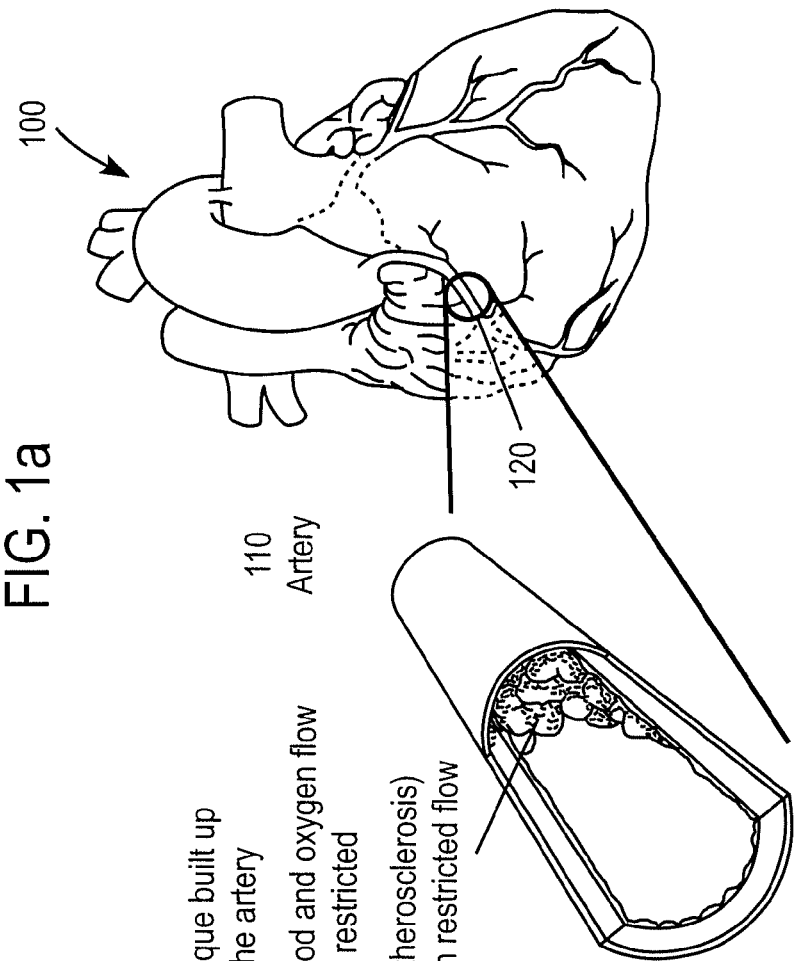

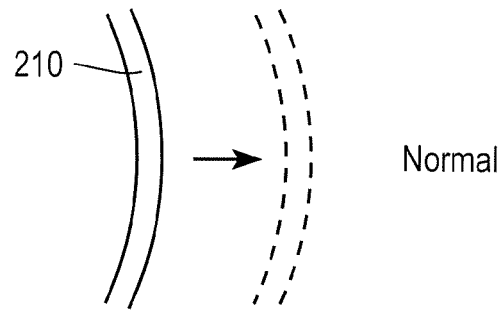
FIG. 2a  Normal
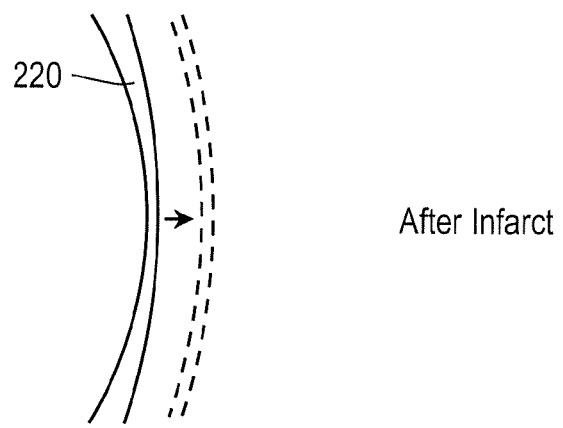
FIG. 2b  After Infarct
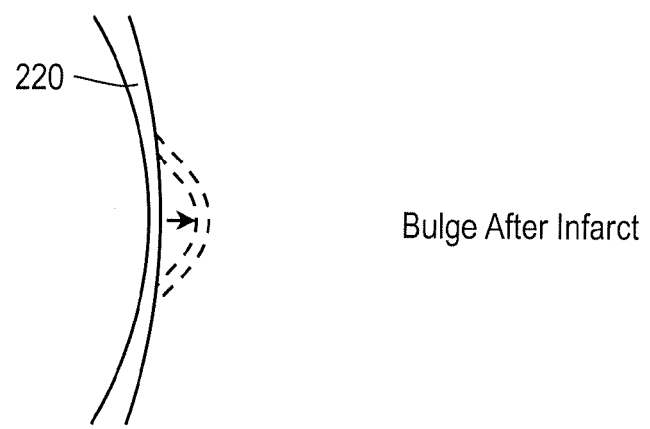
FIG. 2c  Bulge After Infarct Crosslinking Functionalities:
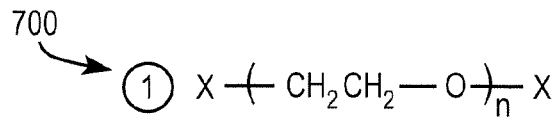
OR
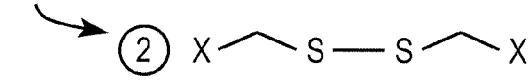
Where X =  ← 730
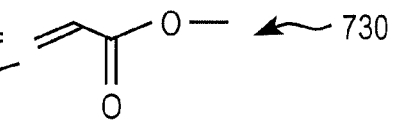 ← 740
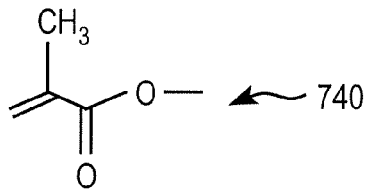 ← 750
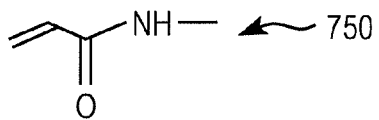 ← 760
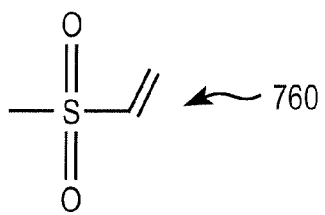 ← 770
FIG. 7b Reduced Thiolated Hyaluronan
I: DTP, EDC pH 4.7  II: NH₃, EDC, pH: 4.7  III: DTT, pH 8.0

HYDROGEL BIOSCAFFOLDINGS AND BIOMEDICAL DEVICE COATINGS

BACKGROUND OF THE INVENTION

1. Field of the Invention

Sequence Listing

This application contains a sequence listing submitted on one compact disc (in duplicate) which comprises the following file:

05618P4437_sequence_listing 1 file(s)

Size: 533 bytes

Size on disk: 2.00 KB (2,048 bytes)

Created: Jun. 12, 2007

The material on the compact disc, which comprises the sequence listing, is hereby incorporated herein by reference.

The present invention relates to the field of bioscaffoldings formed in an infarct region of the heart or bioscaffoldings used as a coating on biomedical device such as a stent or a pacemaker lead. In particular, the invention relates to biofunctionalized bioscaffoldings formed of hyaluronan crosslinked with another type of hydrogel that is naturally found in the extra-cellular matrix (ECM), such as collagen, collagen-laminin, and poly-1-lysine. Fibrinogen or alginate hydrogels may also be used in combination with hyaluronan.

2. Discussion of Related Art

Myocardial infarction (MI) is one form of heart disease that often results from the sudden lack of the supply of oxygen and other nutrients due to the lack of blood supply to a portion of the heart. The lack of blood supply is a result of the closure of the coronary artery that nourishes a part of the heart muscle in the left ventricle. The coronary artery 110 containing a blockage 120 is illustrated in FIG. 1a. The cause of this event in coronary vessels is generally caused by arteriosclerosis, the "hardening of the arteries." MI may also be the result of minor blockages where, for example, there is a rupture of cholesterol plaque resulting in blood clotting within the artery. Thus, the flow of blood is blocked and downstream cellular damage occurs. As a result of this insult to the heart tissue, scar tissue tends to naturally form. FIGS. 1a and 1b illustrate the progression of heart damage once the build-up of plaque induces a blockage 120 to occur. FIG. 1a illustrates a site of a blockage 120 and the resulting restricted blood flow can occur from any of the indicated causes. FIG. 1b illustrates the extensive damage to the left ventricle that can be a result of the lack of oxygen and nutrient flow to the left ventricle of the heart 100. FIG. 1b illustrates the two regions of an infarct region. The infarct region has (1) the "necrotic zone" 130 which is a region of significant necrosis/apoptosis tissue and (2) the "border zone" 140 that consists of a large concentration of apoptotic and necrotic tissue as well as viable tissue. In the border zone the cells exist in an oxygen-deprived state due to the blockage 120 of the coronary artery 110. The region of the heart beyond the border zone 140 is the "remote zone" which is remote of the infarct region and of the damage.

The infarct area will likely undergo remodeling and will eventually form a scar, leading to an area of the heart that does not contract. The remodeling of the heart is due to mechanical forces resulting in uneven stress and strain distribution in the left ventricle. MI damage can cause irregular rhythms of the heart that can be fatal, even though the remaining muscle is strong enough to pump a sufficient amount of blood. Remodeling of the heart begins immediately after an MI. The principle components of the remodeling event include myocyte death, edema and inflammation, followed by fibroblast infiltration, collagen deposition, and finally scar formation. The principle component of the scar is collagen. Because mature myocytes of an adult are not regenerated, the infarct region experiences significant thinning, as illustrated in FIG. 2b. FIG. 2a illustrates a normal cross-section of a wall of the left ventricle 210. FIG. 2b illustrates the thinning of the wall 220 after an MI. During systole (contraction of the left ventricle), due to the remodeling of the region, the infarct region may not move very much at all as illustrated in FIG. 2b. The remodeling of the region may also cause the wall 220 to bulge out as illustrated in FIG. 2c, and in an extreme case, rupture.

Over time, post-MI morphological changes occur. The gross morphological changes that occur over approximately a 7-week period are pallor of the myocardium that leads to some hyperemia, and then a yellowing starts to occur central to the damaged region. At approximately 15 days, the area is mostly yellow with soft vascular margins. This area eventually turns white from fibrosis. On a microscopic level, the initial examination reveals wavy myocardial fibers. Coagulation and necrosis with loss of cross striations occur followed by contraction bands, edema, hemorrhage, and neutrophilic infiltrate. Within 24-72 days there is total loss of nuclei and striations and heavy neutrophilic infiltrate. Then macrophage and mononuclear infiltration begin resulting in a fibrovascular response. Once this fibrovascular response occurs, prominent granulation of the tissue follows. This ultimately leads to fibrosis and a scar is formed by about 7 weeks post MI. This timeline illustrates the importance of regenerating the infarct region within a time before extensive scarring and damage occurs.

Despite recent advances in the treatment of acute myocardial infarction (MI), the ability to repair extensive myocardial damage and to treat heart failure is limited. The myocardium is unable to regenerate because there are insufficient numbers of cardiomyocytes or because the cardiomyocytes cannot replicate after injury and because there apparently are no muscle stem cells in the myocardium. The damage of MI is often progressive. Patients who survive MI are prone to scar tissue formation and aneurismal thinning of the damaged region. Even in the absence of cardiac aneurysm, the loss of viable myocardium can result in increased wall stress in the remaining myocardium, eventually triggering a sequence of molecular, cellular, and physiological responses that lead to left ventricular (LV) dilatation and heart failure.

In most cases, cardiac transplantation is the only available treatment that significantly lengthens and improves quality of life. It is limited, however, due to a chronic shortage of donor hearts. A possible strategy to restore heart function after myocardial injury is to induce angiogenesis through the use of a scaffolding. The scaffold temporarily provides the biomechanical support for the cells until they produce their own extracellular matrix and the scaffold may also lower stress in the infarct region by bulking up the region. Because the scaffolding may contain or attract living cells, they may have the potential to induce angiogenesis. Angiogenesis is the growth of new capillaries in the region. After an MI, the infarct tissue as well as the border zone and the remote zone begin to remodel. The scar tissue forms in the infarct region as the granulation is replaced with collagen, causing the scar to thin out and stretch. The perfusion (oxygen flow) in this region is typically 10% of the healthy zone, decreasing the number of active capillaries and therefore limiting the amount of angiogenesis that may occur. Increasing the number of capillaries may lead to an increase in angiogenesis. Other benefits of increasing blood flow to the infarcted region is to provide a route for circulating stem cells to seed and proliferate in the infarct region. Angiogenesis may lead to increased oxygenation for the surviving cellular islets within the infarct region, or to prime the infarct region for subsequent cell transplantation of myocardial regeneration. In the border zone, surviving cells would also benefit from an increase in blood supply through an angiogenesis process. In the remote zone, where cardiac cells tend to hypertrophy and become surrounded with some interstitial fibrosis, the ability of cells to receive oxygen an therefore function to full capacity are also compromised; thus, angiogenesis would be beneficial in these regions as well.

Bioscaffoldings have been formed from a number of different materials. One type of material is a pure alginate scaffolding. Alginate scaffoldings have been implanted as grafts containing fetal cardiac cells into rats and were shown to stimulate neovascularization and attenuated left ventricle dilation and failure. Alginate scaffolds are formed of algae, and are thus not a material that is found naturally in the body. Materials naturally found in the body, and in particular materials that are naturally found in the extracellular matrix (ECM) have also been used to form bioscaffoldings. The ECM is a complex network of fibrillar proteins and glycosaminoglycans, and serves to provide cells with information on their environment. Materials found in the ECM include collagen, hyaluronan, and laminin. The advantage of using these materials to form bioscaffoldings is that they are naturally occurring in the body and may therefore be degraded by enzymes naturally found in the body, such as hyluronidase and colleganase, and then absorbed. Non-functionalized bioscaffoldings formed of these materials include collagen/matrigel-based cardiac muscle constructs, alginate elastin, alginate laminin, hyaluronan, collagen, and collagen hyaluronan hydrogels. Hyaluronic acid hydrogel implants have been loaded with one of two cytokines, vascular endothelial growth factor (VEGF) or basic fibroblast growth factor (bFGF), to elicit new microvessel growth in vivo. Some of these bioscaffoldings have been seeded with stem cells or other types of cells to generate new heart tissue and capillary growth into the scaffolding region. Providing non-functionalized scaffoldings alone to an infarct region of the heart can cause angiogenesis because it is a foreign body. But, non-functionalized scaffoldings or scaffoldings seeded with stem cells provide angiogenesis at a fairly slow rate. It would be valuable to provide a high rate of angiogenesis in as short a time as possible.

SUMMARY OF THE INVENTION

Bioscaffoldings formed of hydrogels that are crosslinked in situ in an infarcted region of the heart (myocardium) by a Michael's addition reaction or by disulfide bonds formed by an oxidative process are described. The bioscaffoldings may be formed of hydrogel components that are found naturally in the body. The hydrogel components may be compounds found naturally in the extracellular matrix (ECM). The hydrogel components may be hyaluronan, collagen, collagen-laminin, poly-1-lysine, or fibrin. The bioscaffolding may include hyaluronan as one of the hydrogel components and the other component may be selected from collagen, collagen-laminin, poly-1-lysine, and fibrin. In one embodiment the bioscaffolding may further include an alginate component. The bioscaffolding may have biofunctional groups such as angiogenic factors and stem cell homing factors bound to the collagen, collagen-laminin, or poly-1-lysine hydrogel component. In particular, the bioscaffoldings may have PR11, PR39, VEGF, bFGF, SDF-1, a polyarginine and DNA plasmid complex, or a DNA/polyethyleneimine (PEI) complex.

Methods of delivering the hydrogel components and crosslinking the hydrogel components in situ in an infarcted region of the heart (myocardium) by Michael's additions or by disulfide bonds formed by an oxidative process are also described. In one embodiment, the hydrogel components may be crosslinked by a Michael's reaction where one of the hydrogel components is functionalized with a nucleophile (Michael donor) and the other hydrogel component is functionalized with an electrophile (Michael acceptor) such that when the two hydrogel components come into contact with one another a Michael's addition reaction will occur to form the crosslinked bioscaffolding in situ. In another embodiment, the hydrogel components may be crosslinked by a Michael's reaction where each of the hydrogel components is functionalized with nucleophiles and a third component is added to the two hydrogel components to crosslink the hydrogel components. This third component is a crosslinking functionality that is functionalized on both ends with electrophiles that will react with the nucleophiles on the hydrogel components through Michael's reactions to crosslink the hydrogel components in situ.

In another embodiment, disulfide bonds formed by an oxidative process may crosslink the hydrogel components in situ. In this embodiment the hydrogel components are functionalized with thiol groups and are placed in the presence of oxygen or oxidative compounds.

In another embodiment the hydrogel components of the bioscaffolding may be delivered to an infarcted region of the heart (myocardium) in combination with microspheres containing a growth factor such as IGF or a stem cell homing factor such as GCSF to increase the release of stem cells throughout the body from the bone marrow.

In yet another embodiment, the hydrogel components of the bioscaffolding may be delivered to an infarcted region of the heart (myocardium) in combination with stem cells. The stem cells may be mesenchymal stem cells or allogenic stem cells. The hydrogel components delivered in combination with mesenchymal stem cells may be hyaluronan and collagen or hyaluronan and fibrinogen. In an embodiment, a pore forming agent may be delivered along with the hydrogel components and the stem cells. In one particular embodiment, the pore forming agent may be delivered in combination with fibrin hydrogel components and the stem cells.

The bioscaffoldings may also be used to coat stents or cardiac medical devices such as pace-maker leads. In these embodiments the bioscaffoldings would be functionalized with DNA plasmids complexed to polyarginine, poly-1-lysine, or with DNA/PEI complexes. The DNA functionalized on the bioscaffoldings encodes proteins that would be valuable for expression by the cells in the positions in the body where either a stent or a pace-maker lead would be placed.

BRIEF DESCRIPTION OF THE DRAWINGS

FIGS. 1a and 1b illustrate a heart before and after a myocardial infarction as well as cross-sectional view of a clogged artery.

FIGS. 2a-2c illustrate the position of a wall of the heart during systole and diastole (contraction) where the wall of the heart is normal and where the wall of the heart has thinned after a myocardial infarct.

FIGS. 5h-5l illustrate an exemplary embodiment of the method of forming a bioscaffolding by crosslinking a first hydrogel component and a second hydrogel component by a Michael's addition reaction.

FIG. 7b is an illustration of several variations of crosslinking functionalities.

DETAILED DESCRIPTION OF THE PRESENT INVENTION

Figure 3A:
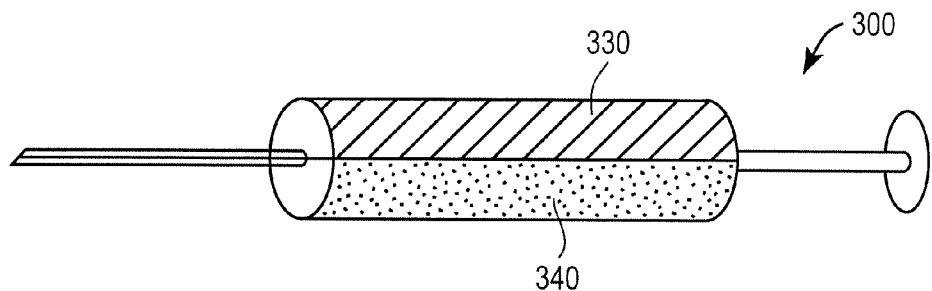
FIGS. 3a-3b illustrate a two-bored needle and the position of injection of the two-bored needle into an infarcted region of the heart.

In the following section, several embodiments of, for example, processes, compositions, devices and methods are described in order to thoroughly detail various embodiments. It will be obvious though, to one skilled in the art that practicing the various embodiments does not require the employment of all or even some of the specific details outlined herein. In some cases, well known methods or components have not been included in the description in order to prevent unnecessarily masking various embodiments.

Bioscaffoldings formed of hydrogels that are crosslinked in situ in an infarcted region of the heart (myocardium) are described. The hydrogels may be crosslinked to form a bioscaffolding by a Michael's addition reaction or by disulfide bonds formed by an oxidative process. Angiogenesis in an infarcted region of a heart (myocardium) may be induced by forming a bioscaffolding in the infarct region to provide mechanical support and to accelerate angiogenesis. Angiogenesis is the growth of capillaries into the infarcted region and the regeneration of myocytes. The bioscaffolding may be formed of hydrogel components that are found naturally in the body. Many of the hydrogel components may be found naturally in the extracellular matrix (ECM). These hydrogel components are hyaluronan in combination with collagen, collagen-laminin, poly-1-lysine, or fibrinogen. The collagen, collagen-laminin, poly-1-lysine, or fibrin include cellular binding cites. The hydrogel components may further include alginate components. The bioscaffoldings may have biofunctional groups such as angiogenic factors and/or anti-apoptotic factors bound to a collagen, a collagen-laminin, or a poly-1-lysine hydrogel component. In particular, the biofunctional groups may be PR11, PR39, VEGF, bFGF, a polyarginine and DNA plasmid complex, or a DNA/polyethyleneimine (PEI) complex. The hydrogel components may be injected into the infarct region along with microspheres containing stem cell homing factors, growth factors such as IGF (insulin-like growth factor), and stem cell release factors such as GCSF (granulocyte colony stimulating factor). Additionally, the hydrogel components may be injected into the infarct region along with stem cells, such as mesenchymal stem cells. Pore forming agents may also be co-injected with any of the hydrogel components.

In one embodiment, the hydrogel components may be crosslinked by a Michael's reaction where one of the hydrogel components is functionalized with a nucleophile (Michael donor) and the other hydrogel component is functionalized with an electrophile (Michael acceptor) such that when the two hydrogel components come into contact with one another a Michael's addition reaction will occur between the nucleophile and the electrophile to form the crosslinked bioscaffolding in situ. In an alternate embodiment the hydrogel components may be crosslinked by disulfide bonds formed by an oxidative process. These types of reactions are valuable for crosslinking hydrogel components in situ because they are reactions that occur under physiological conditions, and in particular may occur under the conditions found in a myocardial infarct region of a heart. The hydrogel components that are functionalized with a nucleophile or an electrophile for a Michael's reaction also allow for the reaction of particular components with one another. Additionally, the Michael's reaction occurs relatively quickly, on the order of seconds to hours. Crosslinking the hydrogel components by disulfide bonds formed by an oxidative process also occurs under the physiological conditions found in the myocardial infarct region of a heart. The infarct region has a lot of oxygen and oxidative stress that cause very fast disulfide bond formation. Oxidative stress is created by secretion of superoxide radical anions and peroxides by macrophages that migrate into the infarct region due to cell death. The superoxide radical anions and peroxides provide for the fast crosslinking of the hydrogel components through disulfide bonds formed by an oxidative process.

Hyaluronan is used as one of the hydrogel components because it provides mechanical support and because it is a component of the extra-cellular matrix material found naturally in the body and thus may be degraded naturally over time by the body by the enzyme hyaluronase as cells move into the bioscaffolding and angiogenesis of the myocardial infarct region occurs. Additionally, hyaluronan includes hydrophilic portions (hyaluronic acid) that promote perfusion of body fluid into the bioscaffolding to allow for the passive transport of oxygen and nutrients into the myocardial infarct region and for the removal of waste products. But, it would also be valuable to form a bioscaffolding that includes cellular binding sites and includes angiogenic factors and/or anti-apoptotic factors bound to the bioscaffolding. For these properties, hyaluronan is crosslinked to a second hydrogel that may also be found in the extracellular matrix and which also allows for cellular adhesion, such as collagen, collagen-laminin, poly-1-lysine, or fibrinogen. Collagen, collagen-laminin, poly-1-lysine, and fibrinogen include cellular binding cites. Furthermore, angiogenic factors and/or anti-apoptotic factors may be bound to the second hydrogel component collagen, collagen-laminin, or poly-1-lysine to further induce angiogenesis. Therefore, hyaluronan in combination with a second hydrogel such as those just described provides a bioscaffolding with superior properties for angiogenesis of a myocardial infarct region of the heart.

In these embodiments, the bioscaffolding is formed in the infarct region by injecting a two-bored delivery lumen, such as the two-bored needle 300 illustrated in FIG. 3a, into an infarcted region of the myocardium. In an alternate embodiment, the two-bored delivery lumen may be a two-bored catheter. The two-bored needle 300 has a first portion containing a first hydrogel component 330 provided at block 410 of FIG. 4 and a second portion containing a second hydrogel component 340 provided at block 420 of FIG. 4a. The first hydrogel component 330 may be hyaluronan. In the embodiment where a Michael's reaction is used to cross-link the hydrogel components, hyaluronan may be functionalized with a nucleophile (Michael donor.) In the embodiment where disulfide bonds formed by an oxidative process is used to cross-link the hydrogel components, hyaluronan may be functionalized with a thiol. FIG. 5a illustrates hyaluronan 500 functionalized with the electrophiles such as a pegylated acrylate 510, a pegylated methacrylate 520, a pegylated vinyl sulfone 530, or a pegylated malemide 540. FIG. 5b illustrates hyaluronan 500 functionalized with a thiol 521. Hyaluronan is a material that is found naturally in the extra-cellular matrix (ECM). Hyaluronan therefore has a good chance of acceptance by the body as part of a bioscaffolding and it may also be degraded within the body by hyaluronidase, an enzyme found naturally in the body. Hyaluronan serves as a hydrophilic portion of the bioscaffolding that promotes the perfusion of body fluid into the bioscaffolding, and thus the infarct region. The hydrophilic properties of hyaluronan also allows for the passive transport of oxygen into the region and nutrients into the region, as well as the transport of waste products out of the region. These are all important functions in supporting angiogenesis in an infarct region. Hyaluronan is also a valuable hydrogel component in the bioscaffolding due to its thromboresistance (will not cause the clotting of platelets), hemocompatibility, and non-fouling (prevents proteins from adhering to surface of bioscaffolding) properties. But, hyaluronan alone is not enough to support the viability of myocyte regeneration in the infarct region. A second hydrogel component is needed to provide for cellular adhesion, additional mechanical support, and binding and release cites for biofunctionalities such as angiogenic factors or DNA sequences that may produce angiogenic factors.

The second hydrogel component 340 within a portion of the two-bored needle 300 may be collagen, collagen-laminin, poly-1-lysine, or fibrinogen. In one embodiment, these components may be functionalized with a nucleophile (Michael donor) that can react with the electrophile (Michael acceptor) on hyaluronan when combined in situ. In another embodiment, the second hydrogel component may be functionalized with a thiol to crosslink the bioscaffolding by disulfide bond formation by an oxidative process. Collagen and collagen-laminin are components of the ECM and may be found naturally in the body and may be degraded over time by enzymes that are naturally occurring in the human body such as collegenase.

Poly-1-lysine is an amino acid chain that can form long chain polymers and is a component to which cells may adhere. Additionally, each amine of the amino acids on the backbone of poly-1-lysine is capable of undergoing a Michael's addition reaction because they are nucleophiles (Michael donors.) This is valuable because poly-1-lysine may be crosslinked with hyaluronan through a Michael's addition to the electrophile groups such as acrylate, methacrylate, vinyl sulfone or a malaimide that may be bound to the hyaluronan hydrogel component. Also, the terminal amines or side-chain amines of the amino acids of poly-1-lysine can bind to biofunctionalities such as angiogenic factors through an amide bond.

A collagen modified with a thiol functionality and cysteine terminal laminin fragments ("collagen-laminin") may also be used. The collagen of the collagen-laminin also binds to those cells expressing alpha-2-beta-1 integrin, such as endothelial cells. The laminin fragment of the collagen-laminin binds to cardiomyocytes. The binding of cardiomyocytes to laminin is described in (*In vitro generation of differentiated cardiac myofibers on micropatterned laminin surfaces* by Devitt, et. al., 2002 Wiley Periodicals, Inc. J Biomed Mater Res 60: 472-479).

Figure 6A:
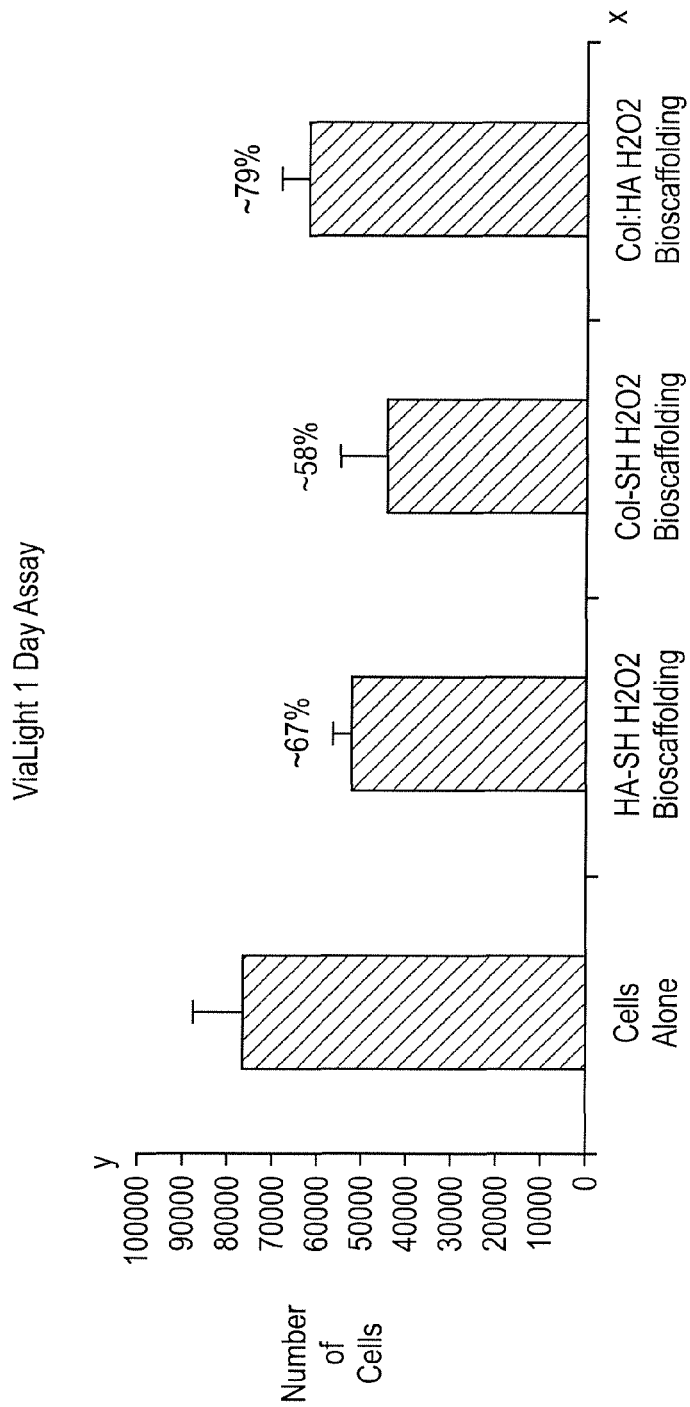
FIG. 6a illustrates a bar graph of the mesenchymal stem cell viability one day after coinjection with the different bioscaffoldings.
Figure 6B:
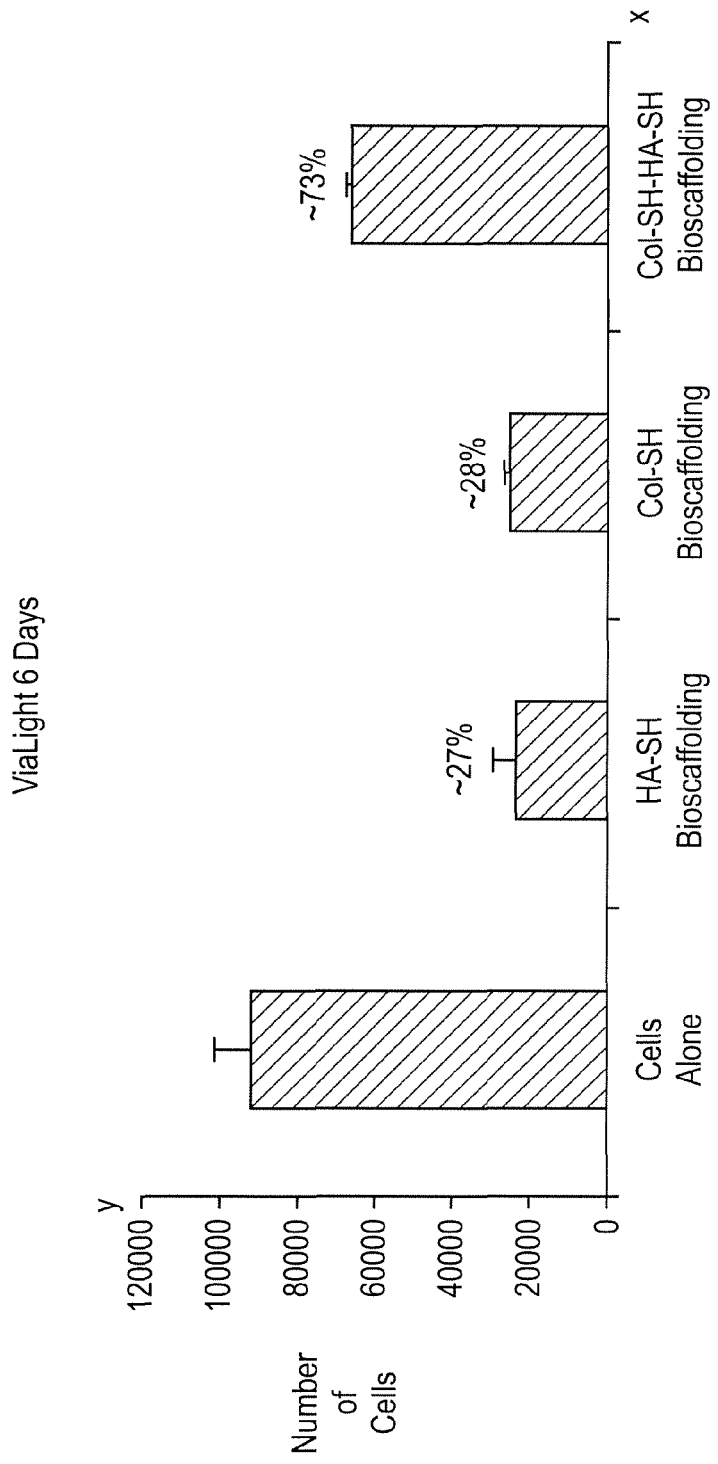
FIG. 6b illustrates a bar graph of the mesenchymal stem cell viability and proliferation 6 days after coinjection with the different bioscaffoldings.

The backbone of collagen has a non-specific cell binding sequence based on the arginine-glycine-aspartic acid peptide sequence (RGDx). The RGDx sequence of collagen can bind to both the cells in the infarcted region to hold the scaffolding in place and to the stems cells that enter the scaffolding. For example, the collagen may bind to cells expressing alpha-2-beta-1 integrin, such as endothelial cells. Additionally, bioscaffoldings formed of both hyaluronan and collagen have been shown to increase the viability and proliferation of mesenchymal stem cells that are coinjected into the infarct region with the bioscaffolding components. FIG. 6a illustrates a bar graph of the mesenchymal stem cell viability one day after coinjection with hyaluronan and collagen. The x-axis shows the different experiments conducted, including the cells alone, a pure thiolated hyaluronan bioscaffolding (HA-SH $H_2O_2$) in combination with mesenchymal cells, a pure thiolated collagen bioscaffolding (Col-SH $H_2O_2$), and a bioscaffolding formed of hyaluronan and collagen (Col:HA $H_2O_2$) in combination with mesenchymal cells (Col:HA $H_2O_2$). The number of cells is on the Y-axis. The viability of the mesenchymal stem cells in the presence of both collagen and hyaluronan (Col:HA $H_2O_2$) is approximately 79% of the viability of cells alone, whereas the viability of the mesenchymal stem cells in the presence of a hyaluronan only bioscaffold (HA-SH $H_2O_2$) is approximately 67% of the viability of cells alone and the viability of mesenchymal stem cells in the presence of a collagen only bioscaffold (Col-SH $H_2O_2$) is approximately 58%. FIG. 6b illustrates a bar graph of the mesenchymal stem cell viability and proliferation six days after coinjection with the different bioscaffoldings. Similar to the graph in FIG. 6a, the x-axis shows the different experiments conducted, including the cells alone, a pure thiolated hyaluronan bioscaffolding (HA-SH $H_2O_2$) in combination with mesenchymal cells, a pure thiolated collagen bioscaffolding (Col-SH $H_2O_2$), and a bioscaffolding formed of hyaluronan and collagen (Col:HA $H_2O_2$) in combination with mesenchymal cells (Col:HA $H_2O_2$) and the number of cells is on the Y-axis. The viability of the mesenchymal stem cells with cell proliferation in the presence of both collagen and hyaluronan (Col:HA $H_2O_2$) is approximately 73% of the viability of cells alone, whereas the viability of the mesenchymal stem cells in the presence of a hyaluronan only bioscaffold (HA-SH $H_2O_2$) is approximately 27% of the viability of cells alone and the viability of mesenchymal stem cells in the presence of a collagen only bioscaffold (Col-SH $H_2O_2$) is approximately 28%. The selective binding of the mesenchymal stem cells to hyaluronan may attract a larger proportion of mesenchymal stem cells into the region of the bioscaffolding that may in turn cause greater numbers of mesenchymal stem cells to bind to the non-specific RGDx binding cites of collagen. Hyaluronan selectively attracts mesenchymal stem cells. This is because hyaluronan has CD44+ binding cites that bind to the CD44− binding cites of mesenchymal stem cells. Furthermore, hyaluronan is hydrophilic which prevents the adhesion of other proteins to hyaluronan to bind other types of cells. Fibrinogen, like collagen, also has nonspecific RGDx binding cites and may therefore be substituted in place of collagen. Fibrinogen is a biopolymer that is found naturally in the body to form blood clots. A hyaluronan and fibrinogen bioscaffolding may also increase the viability and proliferation of mesenchymal stem cells similar to the increase of viability and proliferation of mesenchymal stem cells that was found by the combination of hyaluronan and collagen.

In another embodiment, the first hydrogel component and the second hydrogel component may be cross-linked to one another through an alginate gel to promote the direct crosslinking of the first and second hydrogel components to form a bioscaffolding. This embodiment is of particular use when the first hydrogel component and the second hydrogel component are thiolated and are crosslinked in situ in the infarct region of the heart by an oxidative disulfide bond formation. Crosslinking by disulfide bond formation is valuable because it increases cell viability in the infarct region of the heart where the bioscaffolding is formed. But, crosslinking the first hydrogel component and the second hydrogel component by disulfide bond formation through an oxidative process is a relatively slow process. Before the first and second hydrogel components have a chance to form disulfide bonds, the first and second thiolated components may diffuse away from one another such that the components are too far apart to crosslink through disulfide bond formation. The alginate gel is ionically cross-linked by a soluble divalent salt such as calcium chloride ($CaCl_2$) or another calcium (Ca), barium (Ba), or strontium (Sr) salt. Sodium alginate goes in one lumen with the first hydrogel component and the divalent salt goes in another lumen with the second hydrogel component. When the sodium alginate and the divalent salt come into contact with one another the sodium alginate is cross-linked by the divalent salt to form an alginate gel within seconds. Amidst the alginate gel, the first and second hydrogel components will be locked within place. The temporary scaffolding formed by the alginate gel in the infarct region of the heart keeps the thiolated hydrogel components within close proximity to one another for a time sufficient so that they may form disulfide bonds. The alginate gel eventually degrades to leave only the first hydrogel component and the second hydrogel component crosslinked to one another by disulfide bonds. In an alternate embodiment, the alginate gel may be injected as an alginate graft down one of the lumens with the first or second hydrogel component.

Figure 3B:
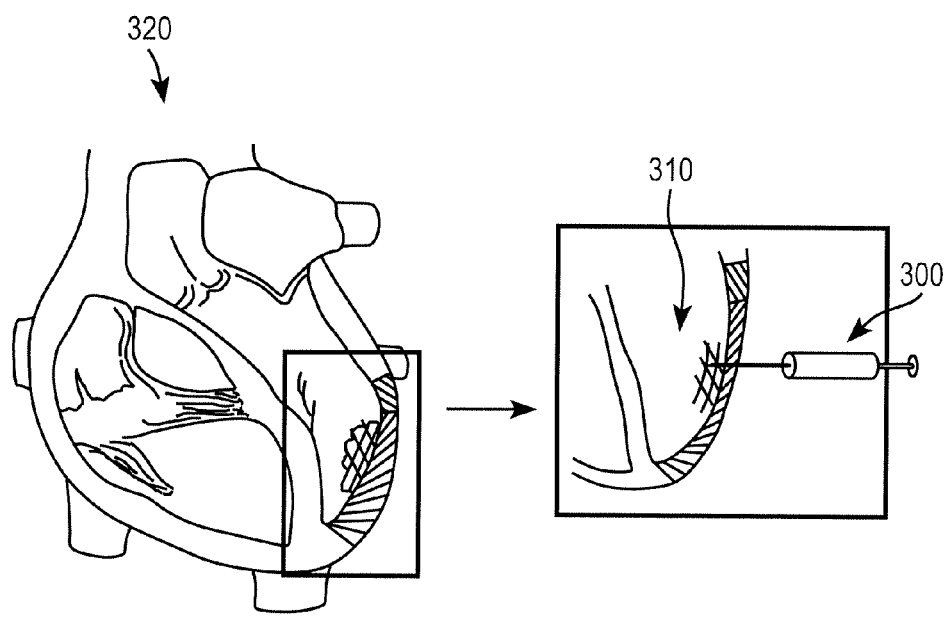
Figure 4A:
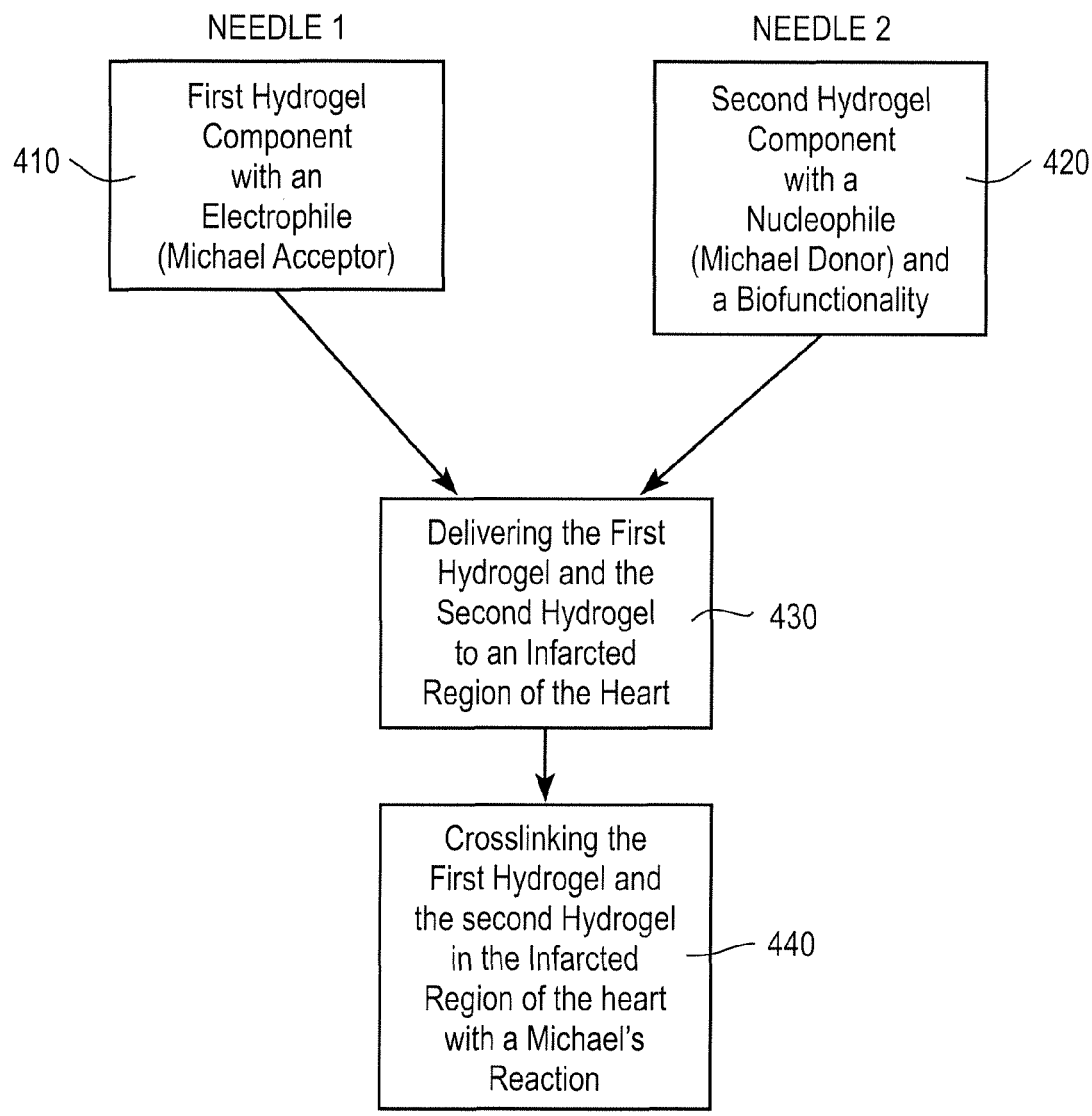
FIG. 4a is a flow chart illustrating a first embodiment of a method of forming a bioscaffolding by crosslinking a first hydrogel component and a second hydrogel component by a Michael's addition reaction.
Figure 4B:
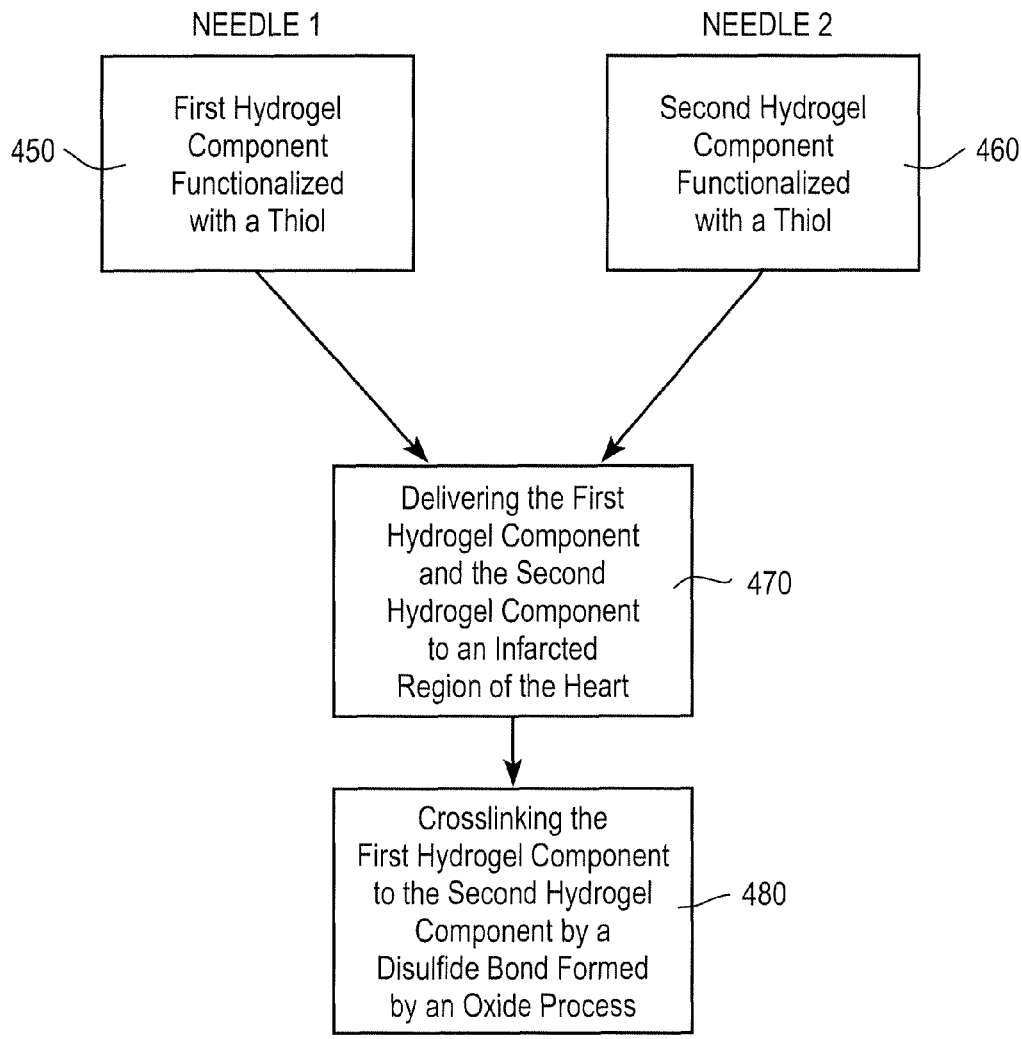
FIG. 4b is a flow chart illustrating a first embodiment of a method of forming a bioscaffolding by crosslinking a first hydrogel component and a second hydrogel component by a disulfide bond formed by and oxidative process.
Figure 5A:
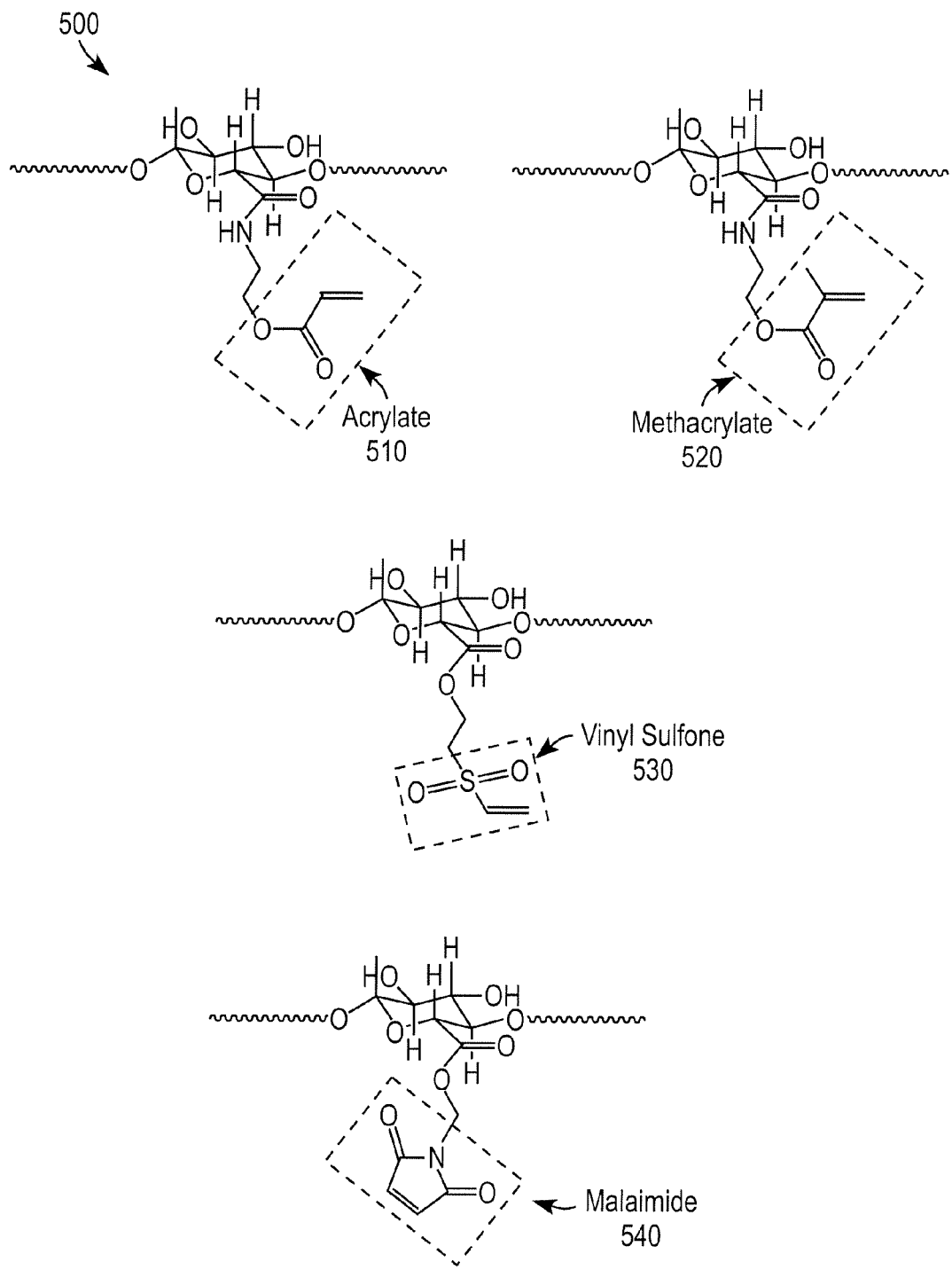
FIG. 5a is an illustration of hyaluronan functionalized with various electrophiles.
Figure 5B:
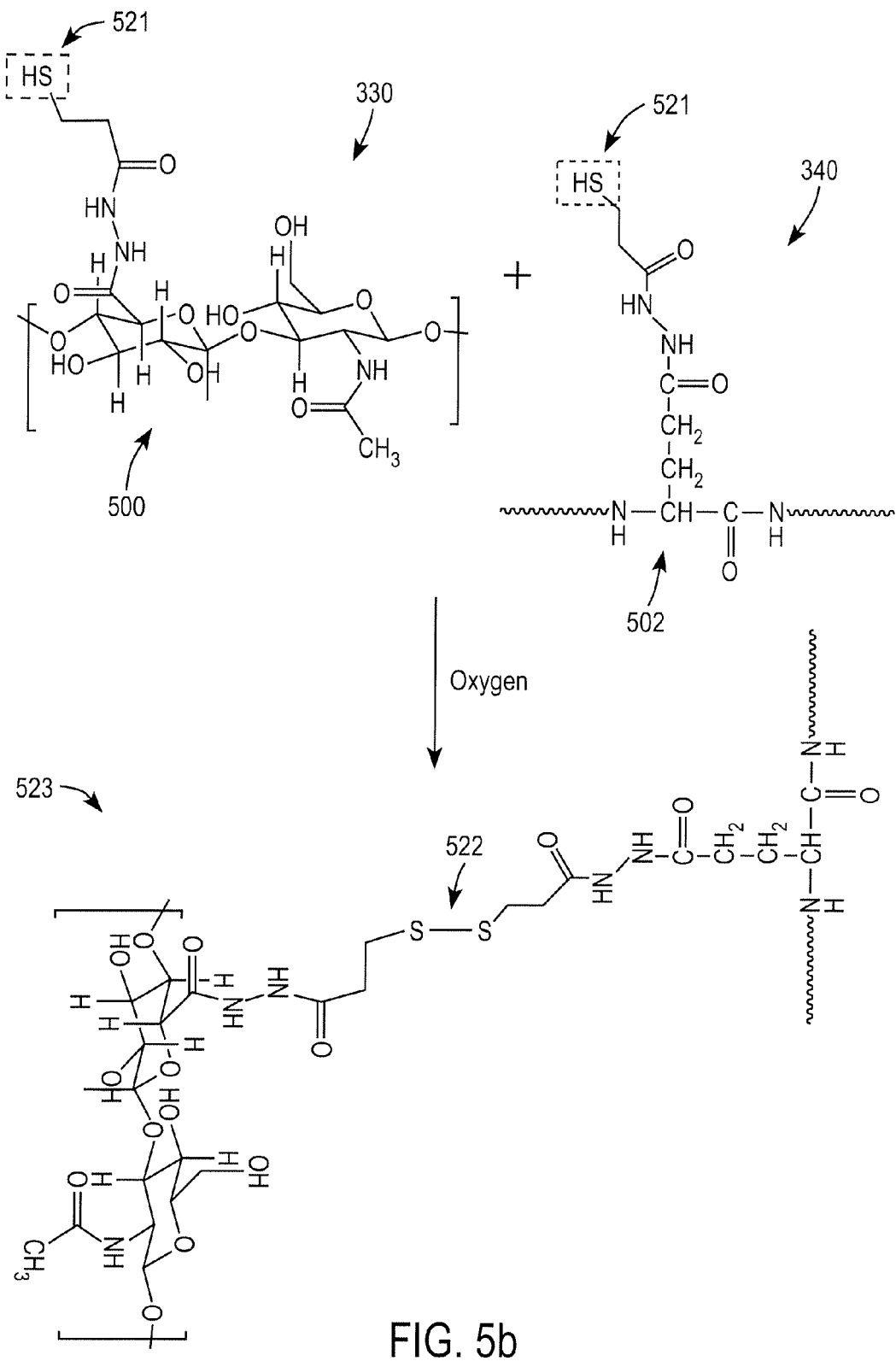
FIG. 5b is an illustration of a disulfide bond formation through an oxidative process.

As illustrated in FIG. 3b, the two-bored needle 300 is injected into the inside of the left ventricle 310 of the heart (myocardium) 320 to deliver the first hydrogel 330 and the second hydrogel component 340 to an infarcted region of the heart at block 430 of FIG. 4a. The infarcted region of the heart to which the first and second hydrogel components are delivered may be both the border zone and the remote zone to ensure full coverage of the bioscaffolding in the infarct region. In one embodiment, the first hydrogel component 330, hyaluronan functionalized with an electrophile (Michael acceptor) and the second hydrogel component 340, collagen, collagen-laminin, poly-1-lysine, or fibrinogen functionalized with a nucleophile (Michael donor), may be delivered to the infarcted region of the myocardium through the first and second needles, respectively. The first hydrogel component 330 functionalized with an electrophile (Michael acceptor) and the second hydrogel component 340 functionalized with a nucleophile (Michael donor) are then crosslinked in the infarcted region to form a bioscaffolding by a Michael's addition reaction between the electrophile on the first hydrogel component 330 hyaluronan and the nucleophile on the second hydrogel component 340, collagen, collagen-laminin, or poly-1-lysine at block 440 of FIG. 4a. Regardless of the mechanism by which the bioscaffolding is formed, the bioscaffolding may have pores with openings having a diameter in the approximate range of 1 micrometer to 60 micrometers. The pore size of the bioscaffolding will increase over time as cells begin to grow within the bioscaffolding due to the proteins secreted by the cells that decompose the bioscaffolding. The decomposition of the bioscaffolding over time allows for further in-growth of capillaries and cells.

In another embodiment, the first hydrogel component 330 and the second hydrogel component 340 may be crosslinked in situ by a disulfide bond formed through an oxidative process. Disulfide bond formation through an oxidative process is the formation of a sulfur-sulfur bond 522 between the thiols 521 on the first hydrogel component 330 and second hydrogel component 340 in the presence of oxygen or oxidative stress, as illustrated in FIG. 5b. In FIG. 5b, the first hydrogel component 330 is hyaluronan 500 and the second hydrogel component 340 is collagen 502. It is to be understood that the hyaluronan 500 and the collagen 502 illustrated in FIG. 5b may formed of many repeating units and not just one unit as illustrated. The second hydrogel component 340 may also be other hydrogels such as collagen-laminin, poly-1-lysine, or fibrinogen. A first hydrogel component 330 that is functionalized with a thiol 521 is placed within a first needle at block 450 of FIG. 4b and the second hydrogel component 340 functionalized with a thiol 521 is placed in a second needle at block 460 of FIG. 4b. The amount of hyaluronan 500 with respect to collagen 502 that is injected may be any ratio. To minimize the amount of cross-linking between the components that occurs within the needles before delivery, the needles are purged with nitrogen prior to being loaded with the hydrogel components. The nitrogen purge may remove enough oxygen from the interior of the needles to prevent crosslinking by disulfide bond formation by an oxidative process prior to injection. The first hydrogel component 330 and the second hydrogel component 340 are then delivered to an infracted region of the heart at block 470 of FIG. 4b. Once delivered to the infarct zone and/or the border zone the first hydrogel component 330 and the second hydrogel component 340 crosslink at block 480 of FIG. 4b by the formation of disulfide bonds 522 as illustrated in FIG. 5b due to the high levels of oxygen and oxidative stress within the infarct region. These disulfide bonds are formed relatively quickly. Oxidative stress is the presence of oxidative species such as superoxide radical anions and peroxides that are secreted by the macrophages that move into the infarct region due to the cell death. These oxidative species accelerate the formation of disulfide bonds between the hydrogel components.

A biofunctional group may be bound or complexed to the second hydrogel component. The biofunctional group is modified with a linkage that is hydrolytically or enzymatically cleavable to allow for the release of the biofunctional group. The biofunctional group may be bound to the second hydrogel component through a polyethylene glycol (PEG) polymer chain to keep the biofunctionality away from the backbone of the second hydrogel component. An embodiment of a synthesis to bind the biofunctional group to a hydrogel component is described below with relation to FIGS. 8*a* and 8*b*. The biofunctionality is kept away from the backbone to prevent the biofunctionality from becoming sterically engrafted into the crosslinked network. Also, once the hydrolytically unstable bond of the PEG chain is cleaved, the biofunctionality may easily diffuse from the matrix.

The biofunctional group 505 may be an angiogenic factor such as bFGF, PDGF, or VEGF. Angiogenesis is the growth of capillaries into the infarcted region and the regeneration of myocytes. VEGF recruits endothelial cells and induces the formation of microcapillaries. Functionalizing the bioscaffolding containing hyaluronan with VEGF may produce a synergistic interaction between hyaluronan and VEGF. A study has shown that VEGF within crosslinked hyaluronan generated a blood vessel density more than twice the effect of the sum of hyaluronan alone plus VEGF alone (*Stimulation of in vivo angiogenesis by cytokine-loaded hyaluronic acid hydrogel implants* by Peattie et al. Biomaterials Volume 25, Issue 14, June 2004, Pages 2789-2798.) PDGF is a compound produced naturally in the body during the formation of new capillaries. PDGF is formed to aid in the formation of mature capillaries from young microcapillaries and also increases the viability of the mature capillaries. For these reasons, it may be valuable to provide PDGF to an infarct region on a bioscaffolding to enhance the growth of viable capillaries during angiogenesis.

In an alternate embodiment, the biofunctionality bound to the second hydrogel component may be PR11, or PR39. PR39 has the structure of [SEQ ID NO: 1] Arg-Arg-Arg-Pro-Arg-Pro-Pro-Tyr-Leu-Pro-Arg-Pro-Arg-Pro-Pro-Pro-Phe-Phe-Pro-Pro-Arg-Leu-Pro-Pro-Arg-Ile-Pro-Pro-Gly-Phe-Pro-Pro-Arg-Phe-Pro-Pro-Arg-Phe-Pro. PR11 is a smaller protein sequence of PR39 having the structure of [SEQ ID NO: 2] $H_2N$-Arg-Arg-Arg-Pro-Arg-Pro-Pro-Tyr-Leu-Pro-Arg-OH. The terminal arginine acid functionality may be coupled to a HS-PEG-$NH_2$. PR39 is a smaller sequence of the protein that increases the expression of the hypoxia inducing factor 1-α (HIF 1-α) and inhibits the degradation of HIF 1-α. HIF1-α is a compound secreted by the body in areas of low oxygen perfusion, such as a myocardial infarct region of the heart. HIF1-α in turn controls the secretion of other angiogenic growth factors such as VEGF, PDGF and bFGF. Therefore, by binding PR11 or PR39 to the second hydrogel component, a cascade of compounds may be produced in the infarcted region by a single biofunctionality. In this cascade, PR11 or PR39 may control HIF1-α in the infarcted region and HIF1-α in turn may bring several growth factors needed for angiogenesis into the infarcted region, such as VEGF, PDGF, and bFGF. Angiogenesis is a complex process, and providing the combination of the growth factors controlled by HIF1-α to an infarcted region is valuable to promote the accelerated growth of capillaries into the bioscaffolding formed of the first and second hydrogel components. The compounds controlled by HIF1-α also prevent apoptosis (cell death) in the infarcted region and therefore improve myocyte viability in the infarcted region. PR11 is a small peptide having only 11 amino acids and it has no tertiary protein structure. PR11 is therefore more resilient than larger proteins and will not degrade very easily. The small and uncomplicated PR11 peptide structure may withstand high temperatures and changes in pH. PR11 may therefore survive the synthesis of a second hydrogel compound to which PR11 is bound as well as the conditions within the body. Similarly, PR39 does not have tertiary protein structure and may be used in place of PR11.

The biofunctional groups, such as those just described, may induce the growth of new capillaries in the region and the production and influx of stem cells. This may be in addition to the natural influx of cytokines that the body recruits in response to the placement of the bioscaffolding into the body. The surrounding cells secrete cytokines that encourages the growth of growth factors, and after around two weeks, capillary growth may begin. The angiogenic factors on the bioscaffolding will accelerate and prolong this capillary growth so that myocytes may regenerate in the infarct and border zone regions of the left ventricle. Once the capillary growth and the influx of stem cells is sufficient to support viable regeneration of myocytes in the infarct and border zone regions, the bioscaffolding may degrade at a faster rate to allow for the influx of more stem cells and the growth of the myocytes. The degradation of the bioscaffolding may be increased by the growth of capillaries because the increased blood flow into the region will also bring enzymes such as hyaluronidase and collagenase into the bioscaffolding to affect its degradation. The degradation time of the bioscaffolding may be regulated by the crosslinking density of the hydrogel components of the bioscaffolding. The bioscaffolding will degrade at a slower rate with an increasing amount of crosslinking. For example, the bioscaffolding may be crosslinked at every side group of the hydrogel components and may take up to two months to decompose. But, for example, if only one in ten of the sidegroups of the hydrogel components are crosslinked, then the scaffolding may take approximately 3 weeks to decompose.

Figure 5C:
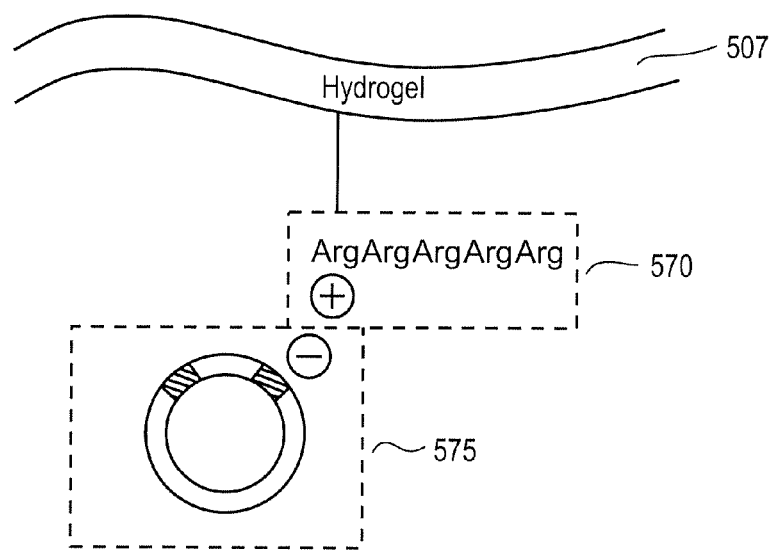
FIG. 5c is an illustration of a DNA plasmid linked to a hydrogel by an ionic bond with polyarginine.
Figure 5D:
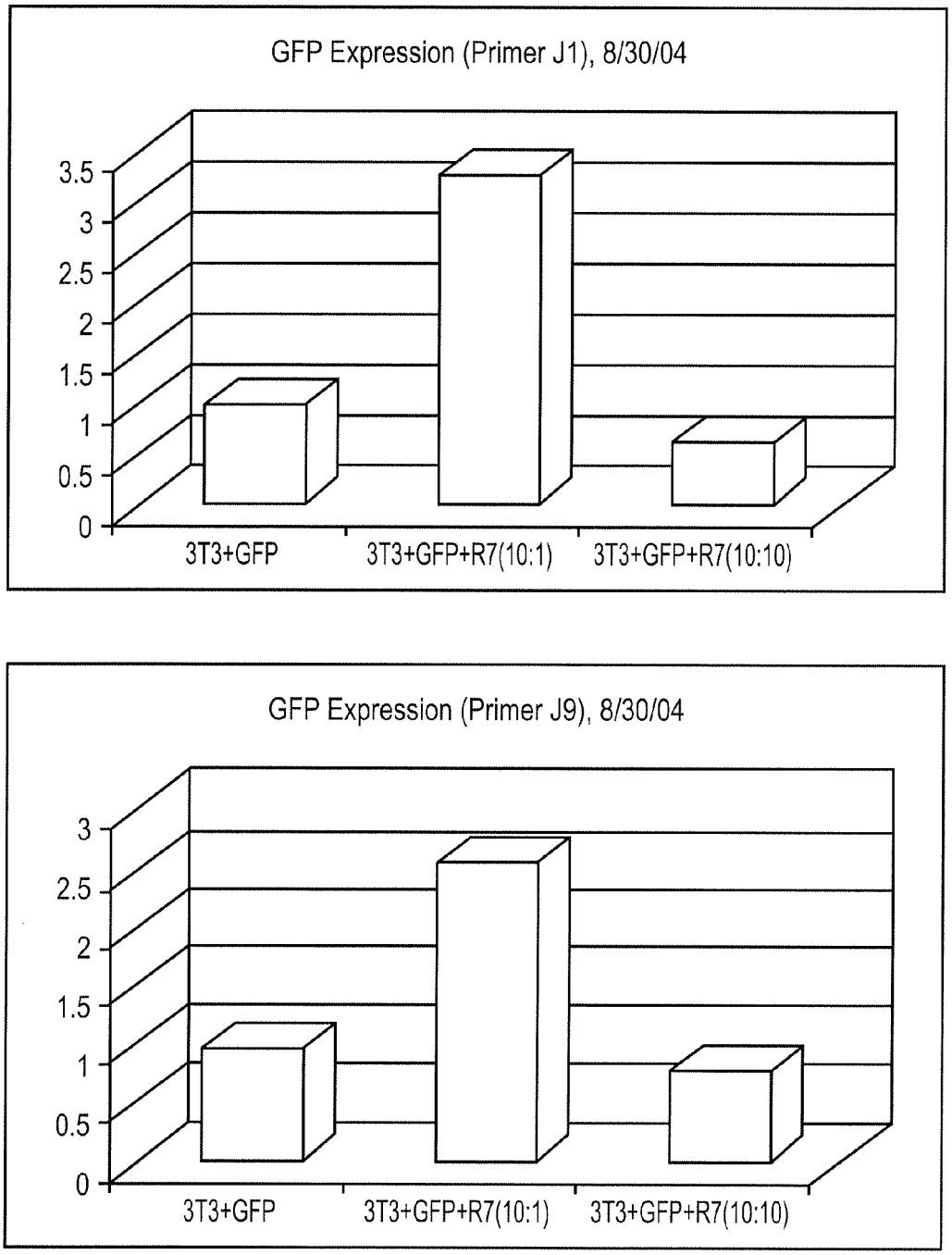
FIGS. 5d and 5e is an illustration of a pair of bar graphs illustrating the greater transfection rate of DNA plasmids complexed to polyarginine than DNA plasmids that are not complexed to polyarginine.
Figure 5E:
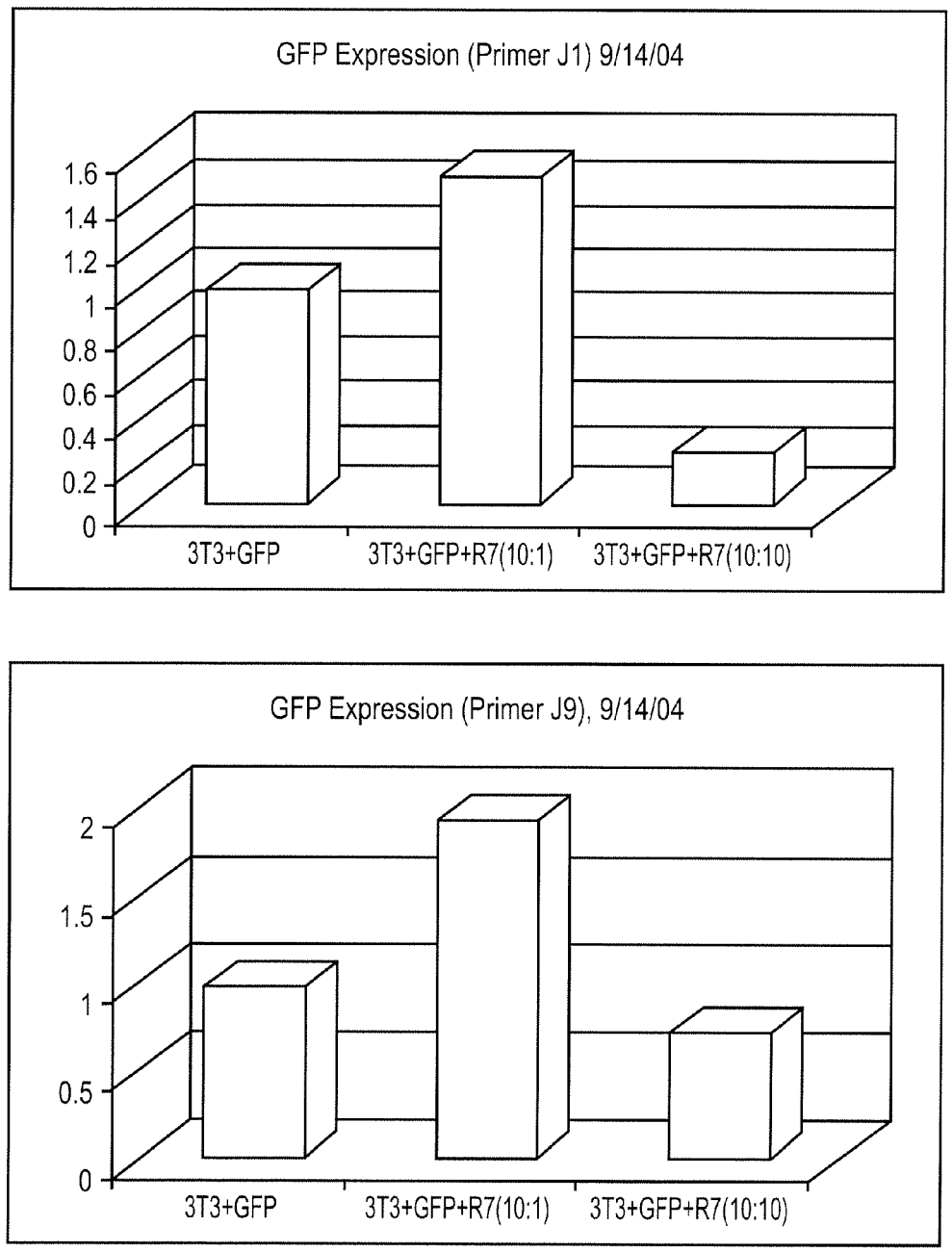

In another embodiment, the biofunctionality may be oligonucleotides that express angiogenic factors, anti-apoptotic factors, or proteins to inhibit or interfere with excessive smooth tissue cell proliferation. The oligonucleotides may be a DNA or an RNA sequence spliced into a plasmid complexed with a polyarginine peptide, a poly-1-lysine peptide, or a short DNA strand complexed with polyethylenimine (PEI). The angiogenic factors that may be expressed by the DNA sequence include a hypoxia inducing factor (HIF) isoform such as HIF1-a and HIF2-a. Other angiogenic factors that may be expressed include insulin drive growth factor (IGF) and nitric oxide synthase (eNOS). HIF-1-alpha binds to hypoxia inducible factor that in turn induces cells to release a variety of growth factors to signal the angiogenesis cascade. Growth factors are individual materials secreted at various points along the cascade. The DNA sequences may be transfected into the cells within the region where the bioscaffolding is formed and provide a permanent means of producing the angiogenic factors. The use of DNA sequences in a DNA plasmid/polyarginine complex or a DNA/PEI complex is valuable because the DNA is a small molecule that does not easily degrade under process conditions. DNA sequences are known to be able to survive polymerase chain reactions (PCR) conducted under 90° C. conditions, and may therefore be able to withstand high process temperatures used to synthesize the hydrogel components as well as temperature conditions within the body without degrading. DNA sequences also do not have the tertiary structure of more complex proteins and therefore are not so sensitive to denaturing. In one embodiment, a DNA plasmid has an overall negative charge and may be ionically complexed to a positively charged polyarginine peptide on a coating or scaffolding. The DNA plasmid may be released in situ by ion exchange by a hydrolytically or enzymatically cleavable linkage to a hydrogel. The bioscaffolding may possess a moiety that can ionically bind to the plasmid as well as allow for the efficient delivery and uptake of the genetic material. In one embodiment, the DNA plasmid 575 may be linked to one of the hydrogels 507 such as collagen, collagen-laminin, or poly-1-lysine by a polyarginine construct 570 as illustrated in FIG. 5c ([SEQ ID NO: 3] Arg-Arg-Arg-Arg-Arg). The polyarginine peptide 570 is polycationic, meaning that it has an overall positive charge, and may therefore ionically bind with the negatively charged plasmid 575. The polyarginine peptide 570 may be a sequence of between 5 and 19 arginines, and more particularly 7 arginine sequences. Polyarginine 570 also may improve the transfection efficiency of the plasmid 575 into a cell. FIGS. 5d and 5e are a series of bar graphs illustrating the greater transfection rate of DNA plasmids complexed to polyarginine than DNA plasmids alone. The y-axis in graphs indicates the changes of DNA plasmid transfection rate in the presence of R7. The transfection rate is set as 1 in the absence of R7 (the first bar). R7 is the polyarginine peptide. 3T3+MT1GFP stands for the condition in which embryonic mouse fibroblasts (3T3 cells) were transfected with the DNA plasmid MT1GFP alone. MT1GFP is a plamis that has a GFP sequence. 10:1 and 10:10 are the ratios of the plasmid to R7 in weight.

Figure 5F:
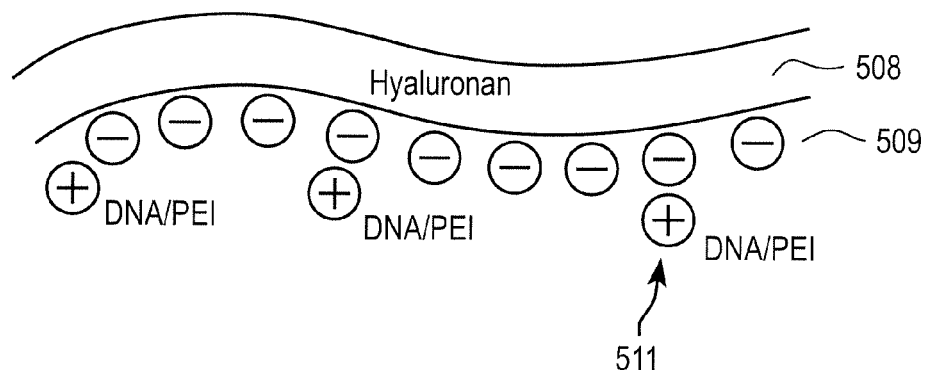
FIGS. 5f and 5g illustrate a DNA/PEI complex bound to hyaluronan through an ionic bond and through a covalent bond, respectively.
Figure 5G:
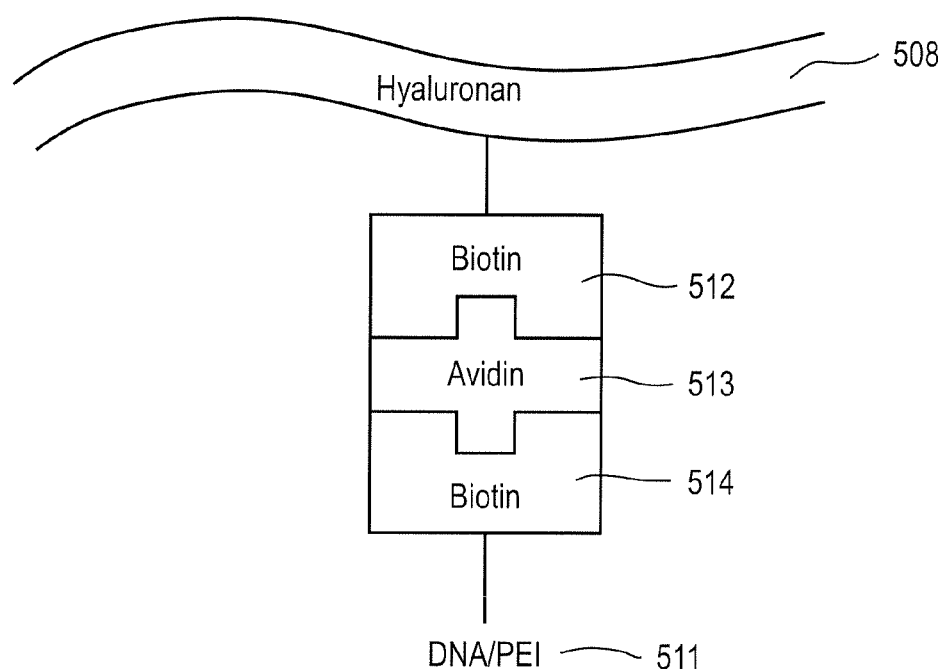

In another embodiment, genetic material encoded in an oligonucleotide may also be placed on a bioscaffolding by using a DNA/PEI complex. As illustrated in FIGS. 5f and 5g a DNA/PEI complex 511 may be bound to the hyaluronan 508 component of the bioscaffolding by an ionic bond or a covalent bond. The DNA/PEI complex 511 has an overall positive charge and may ionically bond to the negatively charged surface 509 of hyaluronan 508. A covalent bond between hyaluronan 508 and a DNA/PEI complex 511, as illustrated in FIG. 5g may be formed by binding a first biotin molecule 512 to hyaluronan 508 and binding an avidin molecule 513 to the first biotin molecule 512 bound to hyaluronan 508. A second biotin molecule 514 is bound to the DNA/PEI complex 511, and that second biotin molecule 514 is in turn bound to the avidin molecule 513 extending from the hyaluronan 508. Biotin and avidin have a very high affinity for one another and will form a very strong covalent bond linking the DNA/PEI complex 511 to the hyaluronan 508. The rate of transfection of the DNA from the DNA/PEI complex 511 that has been coupled with hyaluronan 508 has been shown by Segura T., et al. in "*DNA delivery from hyaluronic acid/collagen hydrogels*", ALCHE Annual Meeting, 2003, 216, to be higher than the rate of transfection of DNA into cells without the presence of hyaluronan. The proteins expressed by the DNA transfected from the DNA/PEI complex may be angiogenic factors such as HIF1-α, HIF2-x, IGF, and eNOS. In another embodiment the expressed proteins may also be proteins that inhibit or interfere with excessive smooth tissue cell proliferation such as protein kinase C δ (Protein Kinase C δ Inhibits the Proliferation of Vascular Smooth Muscle Cells by Suppressing $G_1$ Cyclin Expression, Shinya et. al., The Journal of Biological Chemistry Vol. 272, No. 21, Issue of May 23, pp. 13816-13822, 1997). In yet another embodiment, the expressed proteins may be anti apoptotic factors such as Bcl-2 (*Suppression of signaling through transcription factor NF-AT by interactions between calcineurin and Bcl-2*, Shibasaki et. al., Nature 386(6626):728-31, Apr. 17, 1997) and ILPIP (CT) peptide.

In another embodiment, microspheres containing a stem cell homing factor, either individually or in combination with a stem cell mobilization factor, may be co-injected into an infarcted region of the heart along with the first and second hydrogel components. The microspheres may be approximately 3 weight percent of the total injectate. The dose of the stem cell homing factor within the microspheres may be in an amount sufficient to draw stem cells into the region. The microspheres may be formed of poly(lactide-co-glycolide) and may have a diameter in the approximate range of 10 um and 50 um and more particularly in the range of 20 um and 30 um. The stem cell homing factor that may be encapsulated within the microspheres may be SDF-1. SDF-1 would be valuable to place in the infarcted region because the body's natural signaling to stem cells tapers off around 14 days after a myocardial infarction due to the inflammation in the infarcted area. As the inflammation decreases over around 14 days, the body will stop signaling to stem cells to come into the area. Therefore, by providing SDF-1 to the infarcted region within microspheres that may degrade over a predetermined time period beyond 14 days the signaling to stem cells to come into the region may be extended beyond the initial 14 days so that the regeneration of the myocytes in the infarcted region may occur. Additionally, hyaluronan fragments may play a role in the events underlying stem cell mobilization and trafficking of CD34+ hematopoietic progenitor cells (HPCs) induced by stromal cell-derived factor-1 (SDF-1) (a stem cell homing factor) as described in *Hyaluronan-Derived Oligosaccharides Enhance SDF-1 Dependent Chemotactic Effect on Peripheral Blood Hematopoietic CD34+ Cells* by Sbaa-Ketata et al. in Stem Cells 2002; 20:585-587 www.StemCells.com. The microspheres containing a stem cell homing factor may be injected in combination with allogenic or mesenchymal stem cells.

In one particular embodiment, microspheres containing SDF-1 may be co-injected into the myocardial infarct region with hydrogel components to which PR11 is bound. The combination of PR11 and SDF-1 in an infarcted region may provide for enhanced angiogenesis. This is because the PR11 produces more capillaries that may support the viability of stem cells coming into the infarcted region. PR11 may produce capillaries in the infarcted region and as the microspheres containing the SDF-1 decompose they may release SDF-1 that signals stem cells from the bone marrow to come into the area. In yet another embodiment, the stem cell release factor GCSF (granulocyte colony stimulating factor) may also be placed in microspheres or bound to the hydrogel components to work in conjunction with SDF-1. GCSF mobilizes stem cells from the bone marrow by placing more stem cells into the blood stream. The stem cells in the blood stream may then be drawn into the infarcted region of the heart by SDF-1 where the growth of new capillaries into the bioscaffolding and the infarct region due to PR11 may increase the viability of the stem cells within the bioscaffolding. The stem cells may be retained within the bioscaffolding due to the RGD sequences on collagen or due to the strong adhesion of cells to poly-1-lysine. The microspheres may decompose over approximately a two-month period. The migration of stem cells into the bioscaffolding in the infarcted region causes the bioscaffolding to decompose at an accelerated rate to create room for more stem cells and for the myocytes to regenerate. The accelerated rate of decomposition of the bioscaffolding may occur because the migration of stem cells into the bioscaffolding also brings enzymes into the regions that will degrade the bioscaffolding, such as hyaluronidase and collagenase.

Figure 5H:
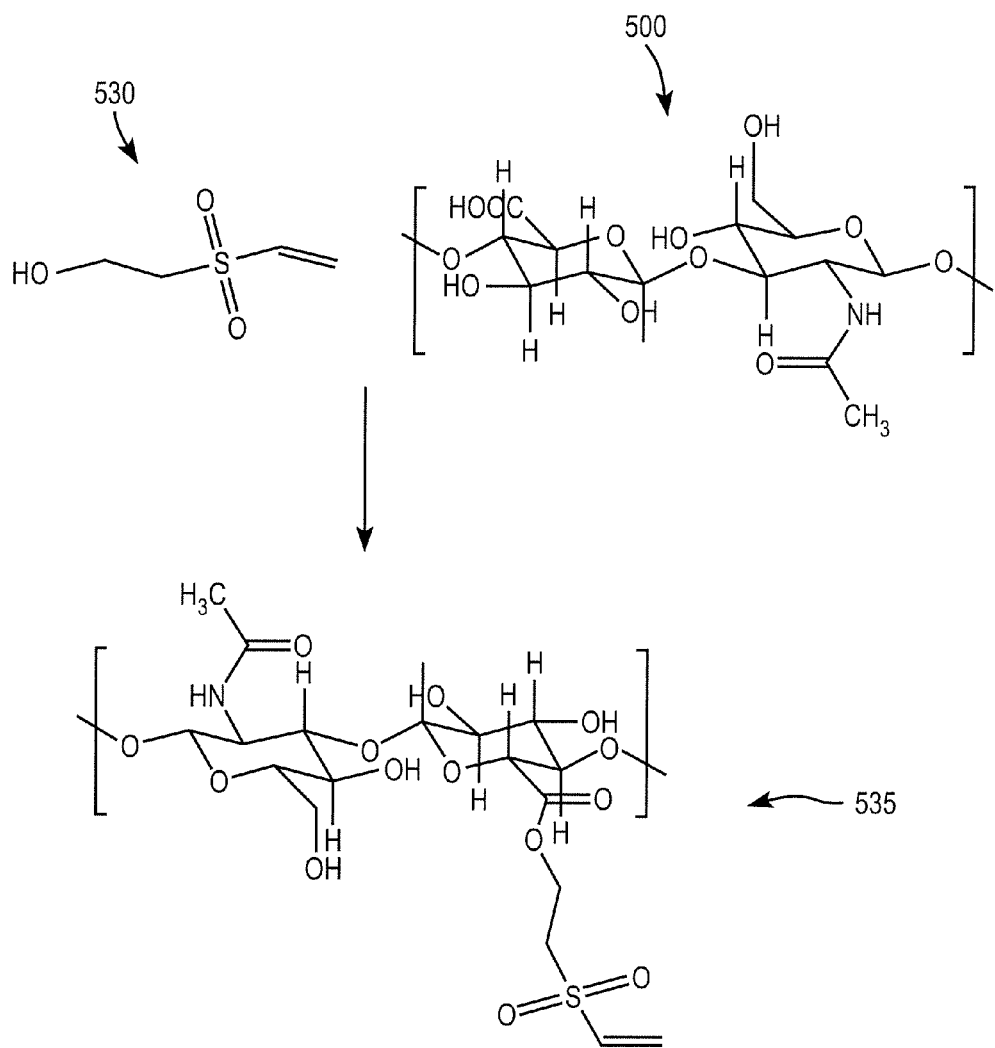
Figure 5I:
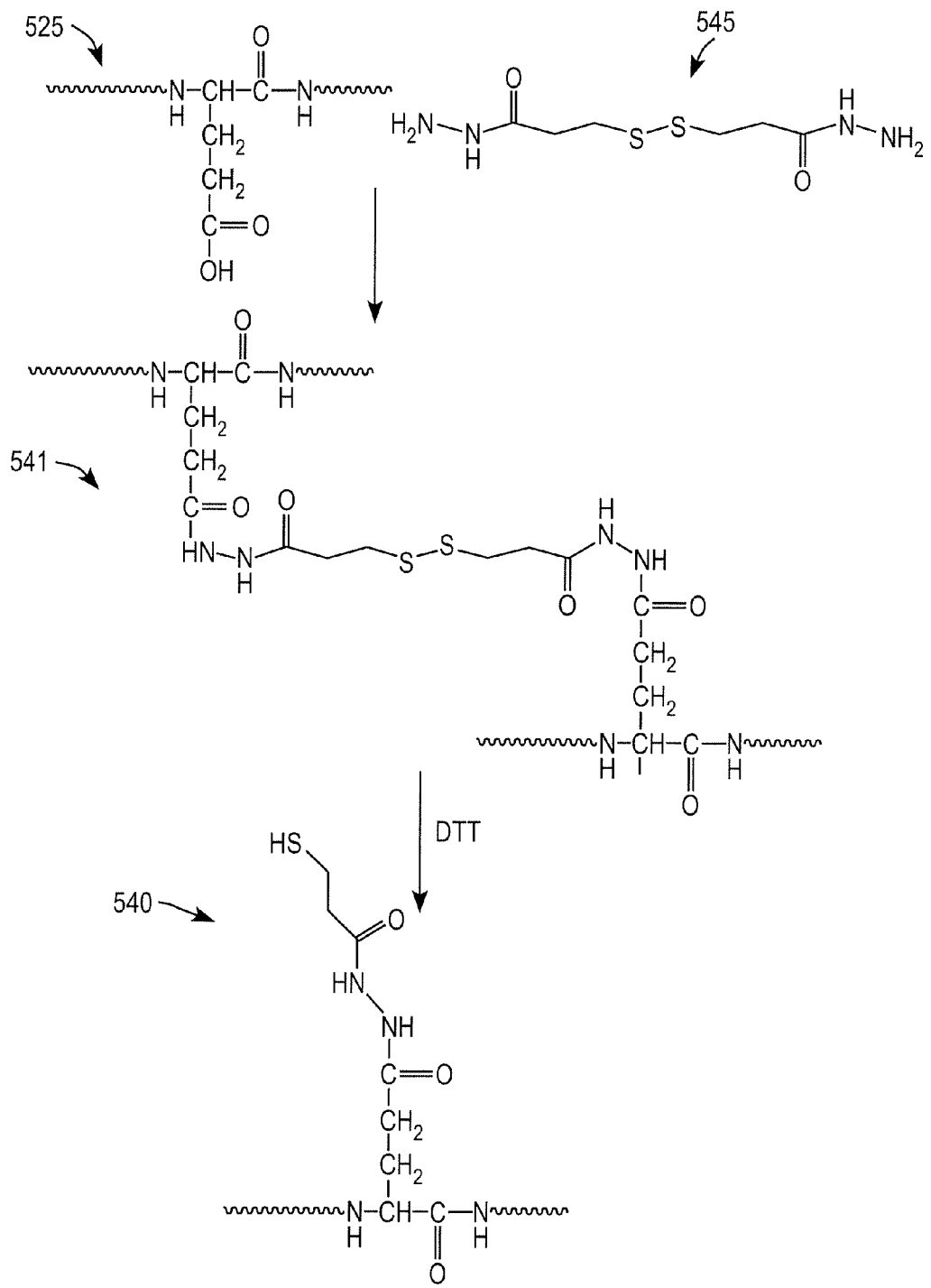

FIGS. 5h-5l illustrate an exemplary embodiment of the method illustrated in FIG. 3b, the two-bored needle 300 is injected into the inside of the left ventricle 310 of the heart (myocardium) 320. The first hydrogel component 330, hyaluronan functionalized with an electrophile (Michael acceptor) and the second hydrogel component 340, collagen, collagen-laminin, or poly-1-lysine functionalized with a nucleophile (Michael donor), may be delivered to the infarcted region of the myocardium through the first and second needles, respectively. In FIG. 5h a pegylated vinyl sulfone 530 is bound to hyaluronan 500 to form a pegylated vinyl sulfone functionalized hyaluronan 535. The molecular weight of the hyaluronan 500 has been reduced from that of the commercially available hyaluronan by acid digestion. The molecular weight of the commercial available hyaluronan may be approximately 2,500,000 g/mol. For proper solution properties, and viscosity for injection, it is desirable to reduce the molecular weight to within the approximate range of 20,000 g/mol and 60,000 g/mol. The pegylated vinyl sulfone 530 is bound to hyaluronan 500 by esterification. This pegylated vinyl sulfone 530 may be reacted with a thiolated collagen 540 such as the one illustrated in FIG. 5i. In FIG. 5i, a non-functionalized collagen molecule 525 is modified with 3,3'-dithiobis(propionoic dihydrazide) (DPT) 545 by a synthesis described by X. Z. Shu, Y. Liu, F. Palumbo, G. D. Prestwich, Biomaterials 24 3825-3834 (2003). In a roundbottom flask, 5 grams of collagen 525 is dissolved in 500 grams of water. The collagen 525 added to the flask has been made soluble in water by breaking the disulfide bonds which in turn breaks the collagen triple helix. To this collagen and water solution, 5.0 grams of 3,3'-dithiobis(propionic dihydrazide) is added. The pH of the entire solution is then adjusted with hydrochloric acid (HCl) to be approximately 4.75. N-(3-dimethylaminopropyl)-N'-ethylcarbodiimide hydrochloride is then added to enable amide bond formation between the 3,3'-dithiobis(propionoic dihydrazide) (DPT) 545 and the collagen 525. The compound 541 is then formed as a solid mass. The pH of this solid mass is adjusted with HCl to maintain the 4.75 pH. With the formation of the solid mass, the reaction is terminated by adjusting the pH to 7.0 with 1 molar (M) NaOH (sodium hydroxide). Dithiothreitol (DTT) (25.0 g) is added to the reaction media to cleave the disulfide bond to form the final product, the thiolated collagen 540. The pH of the solution is then adjusted to pH 8.5 with 1 M NaOH. The reaction media is stirred at room temperature for 24 hours and the pH is re-adjusted to pH 3.5 with 1 M HCl. The sample is then dialysized in a dialysis tube in a media of pH 3.5. The sample is then centrifuged and lypholyzed.

Figure 5J:
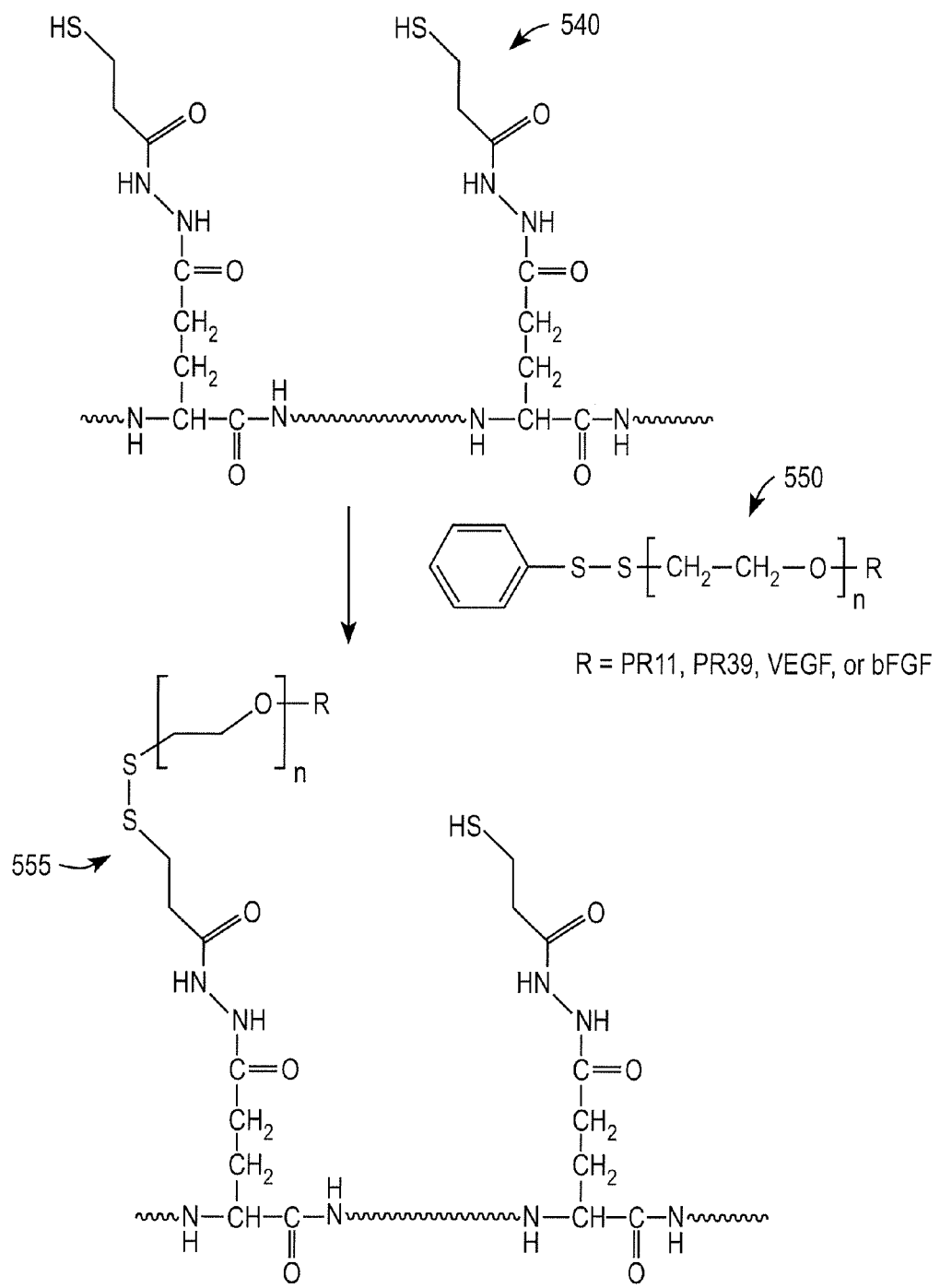
Figure 5K:
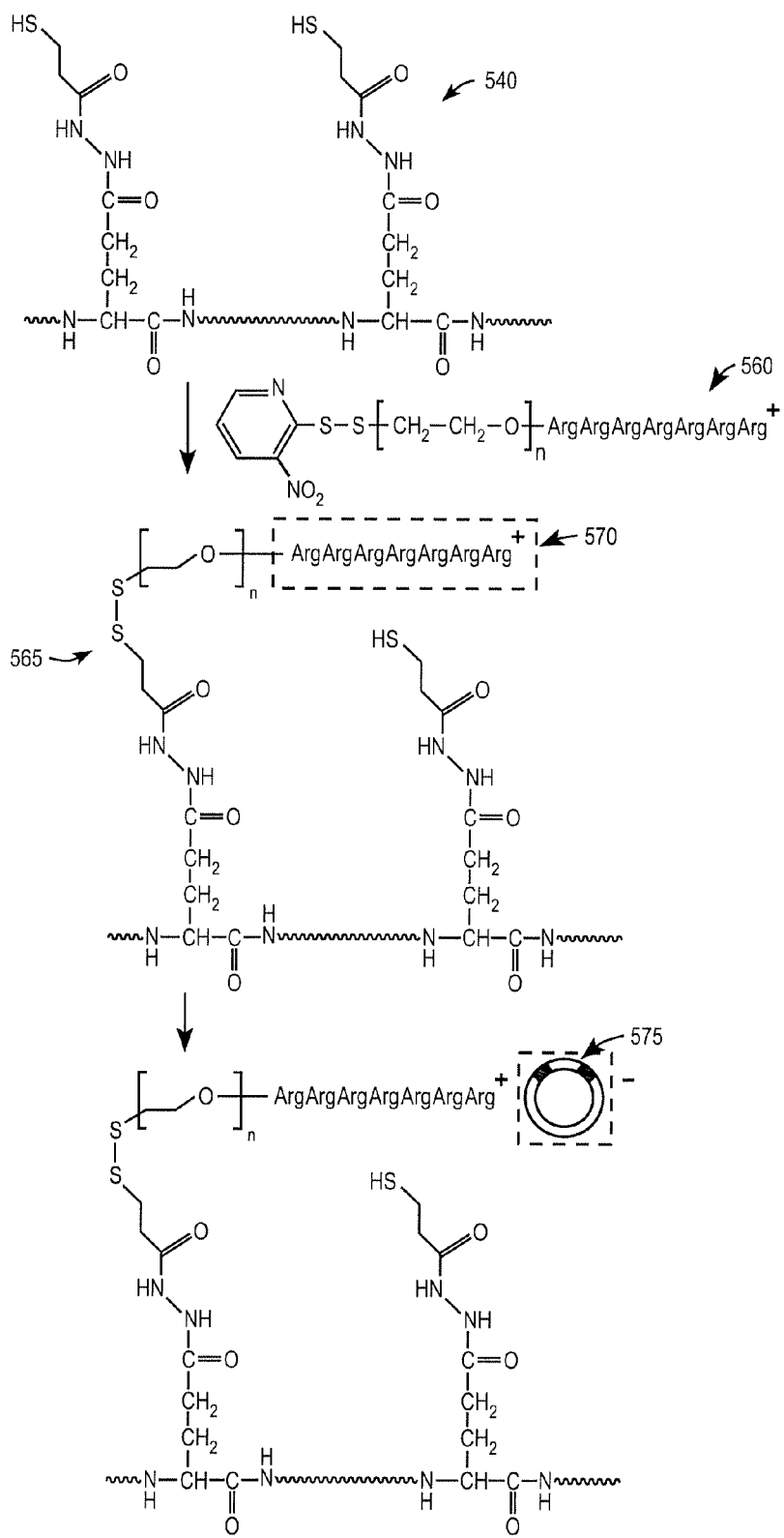
Figure 5I:
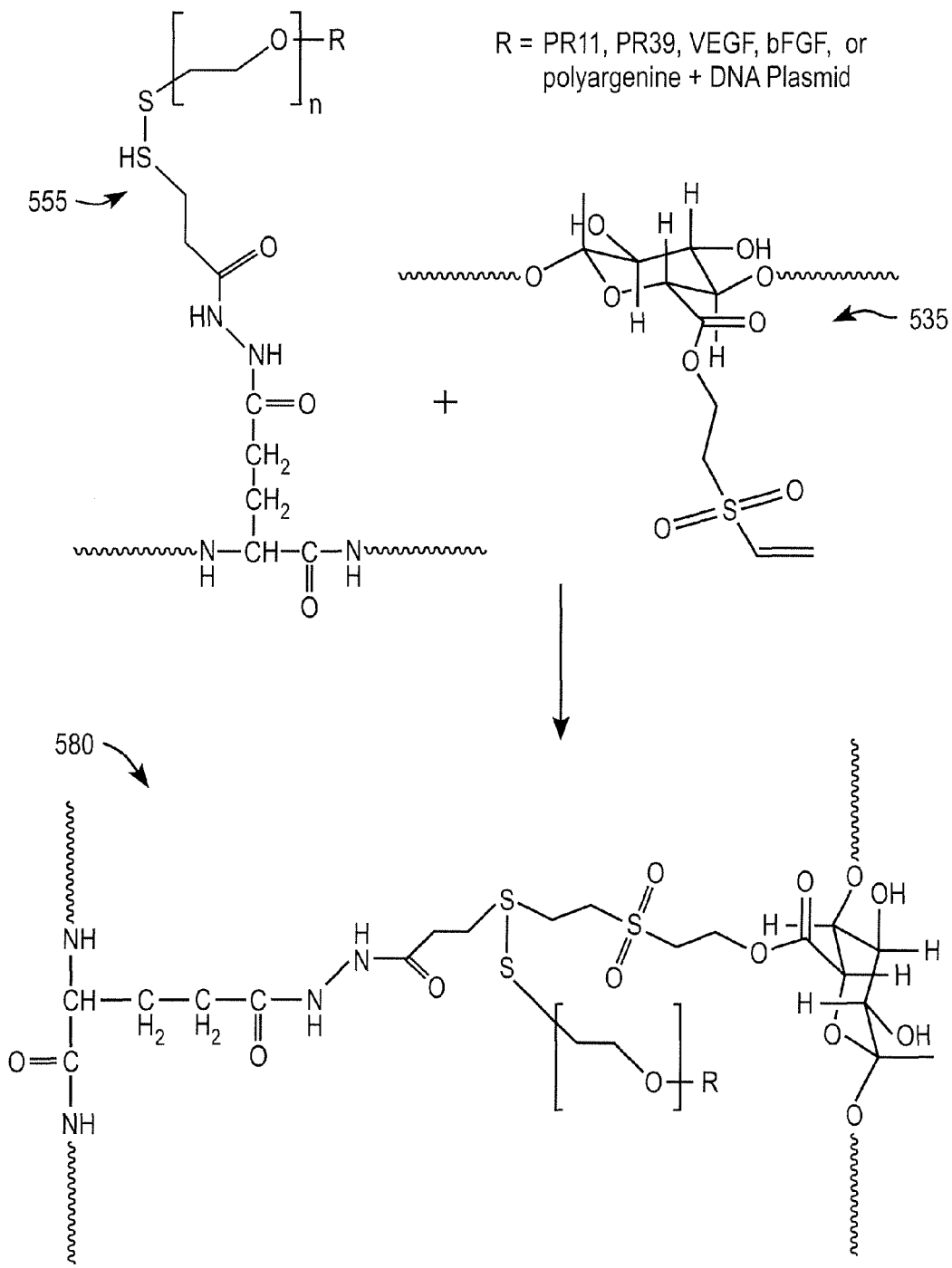

As illustrated in FIG. 5j, the thiolated collagen 540 is then conjugated to a biofunctionality such as PR11, PR39, VEGF, bFGF, or polyarginine complexed to a DNA plasmid. The biofunctionality is first modified with a linkage that is hydrolytically or enzymatically cleavable to form the release of the biofunctionality once the bioscaffolding has been formed in the infarcted region of the heart. The modification of PR11, PR39, VEGF, or bFGF to a pegylated biofunctionality 550, is illustrated in FIG. 5j. For PR11 (H$_2$N-Arg-Arg-Arg-Pro-Arg-Pro-Arg-Pro-Pro-Tyr-Leu-Pro-Arg-OH) [SEQ ID NO: 2], or PR39 that is a longer amino acid chain that contains PR11, this includes amine coupling of the terminal arginine acid functionality to an HS-PEG-NH$_2$ to form a pegylated form of the PR11 or PR39 550, as illustrated in FIG. 5j. The pegylated PR11, PR39, VEGF, or bFGF 550 could then be coupled by heterolytic disulfide coupling to the thiol on the thiolated collagen 540, using less than stoichiometric amounts of HS-PEG-R 550 relative to the thiolated collagen 540 to obtain the desired amounts of the biofunctionality bound to the thiols on the thiolated collagen 540 as illustrated as the biofunctionalized collagen 555. FIG. 5k illustrates binding a polyarginine/DNA-plasmid complex to the collagen backbone. A polyarginine group is bound to a pegylate to form the compound 560. Compound 560 is then reacted with the thiolated collagen 540 to form a polyarginine functionalized collagen 565. The polyarginine group 570 has a positive charge due to the polycationic property of the arginines in the polyarginine group 570. The DNA plasmid 575 has a negative charge due to the polyanionic property of the plasmid. Therefore, the DNA plasmid 575 having a negative charge will be attracted to the positive charge of the polyarginine group 570 and form a complex. Upon injection into the body, the polyarginine undergoes hydrolytic cleavage from the polyethylene glycol group allowing for the efficient delivery of plasmid constructs to cells.

FIG. 5l illustrates the formation of a collagen and hyaluronan bioscaffolding 580 formed of the thiolated biofunctionalized collagen 555 and the pegylated vinyl sulfone functionalized hyaluronan 535. The pegylated vinyl sulfone functionalized hyaluronan 535 is added to a PBS buffered saline with a pH of 7.4. This solution may serve as the first hydrogel component with an electrophile (Michael Acceptor) 410 in FIG. 4a and may be the first hydrogel component 330 in the two bore needle illustrated in FIG. 3a. The thiolated biofunctionalized collagen 555 is then added to a second PBS buffered saline solution with a pH of 7.4. This solution may serve as the second hydrogel component with a nucleophile (Michael Donor) 420 illustrated in FIG. 4 and may be the second hydrogel component 340 in the two bored needle 300 illustrated in FIG. 3a. The biofunctionalized collagen 555 is then coinjected intraventricularly into an infarcted region of the heart with the pegylated vinyl sulfone functionalized hyaluronan 535. The amount of the biofunctionalized collagen 555 relative to the amount of the pegylated vinyl sulfone functionalized hyaluronan 535 may be any ratio. The total amount of the hydrogel components that are injected may be an amount sufficient to form a bioscaffolding in both the border zone and remote zone of the infarcted region of the heart. In an embodiment, the total amount of the hydrogels delivered may be approximately 0.2 milliliters of which approximately 2 to 5 weight percent of the solution delivered are the hydrogel components. When the two hydrogel components mix, the thiolated biofunctionalized collagen 555 and the vinyl sulfone functionalized hyaluronan 535 undergo a Michaels Addition reaction between the electrophilic vinyl sulfone and the nucleophilic thiol resulting in a crosslinked hydrogel bioscaffolding 580. The RGD portions of the collagen 555 backbone may bind to the myocytes (heart muscle cells) within the infarcted region of the left ventricle to hold the crosslinked hydrogel bioscaffolding 580 in place within the heart. In one embodiment, the hydrogel components may be coinjected with stem cells. The RGD sequences on the collagen may also bind to the stem cells to keep them in the bioscaffolding 580 and aid in the acceleration of the regeneration of cells and the growth of capillaries into the infarct region (angiogenesis.)

Figure 7A:
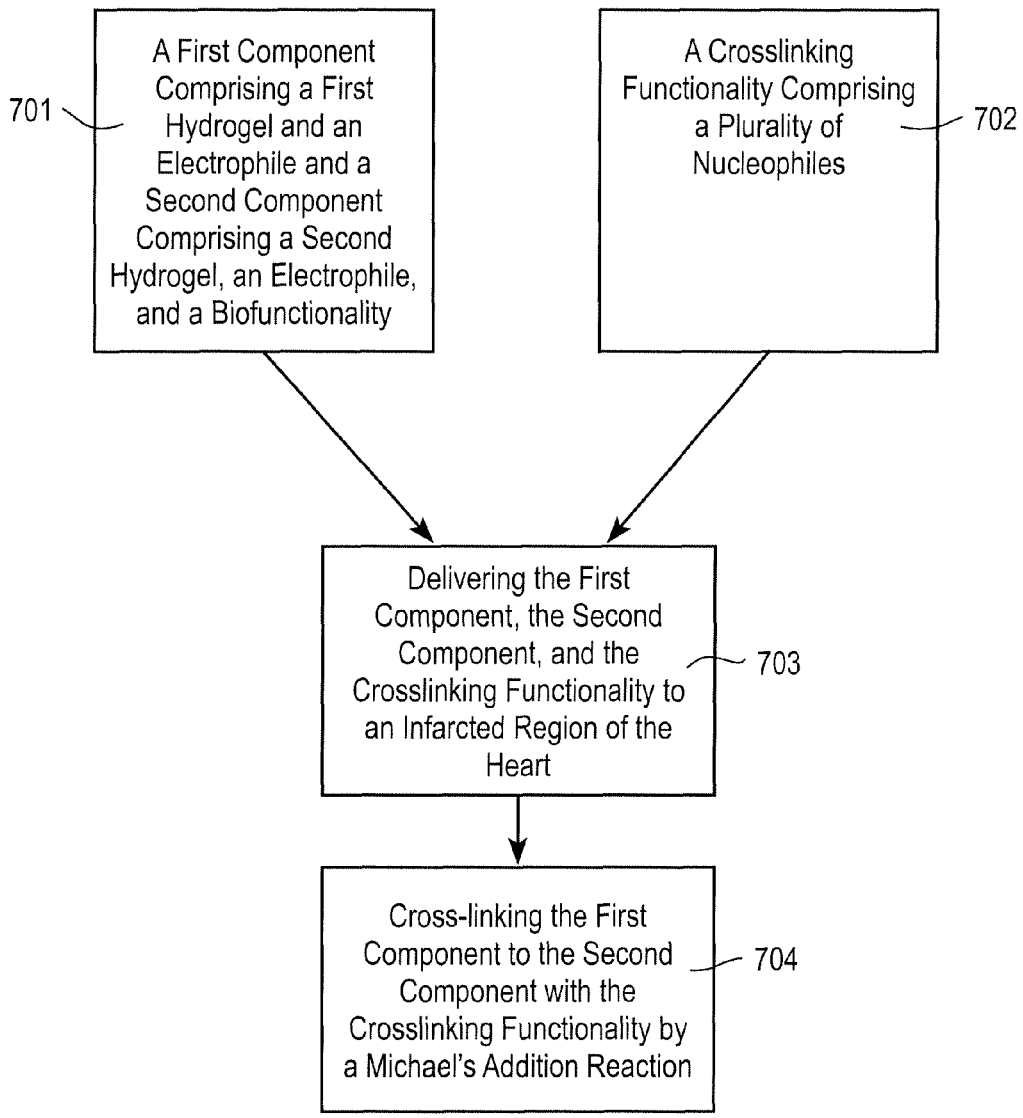
FIG. 7a is a flow chart illustrating a second embodiment of a method of forming a bio scaffolding by crosslinking a first hydrogel component to a second hydrogel component by a crosslinking functionality.

FIG. 7a is a flowchart of a second embodiment of forming a bioscaffolding in situ. In this embodiment, the hydrogel components may be crosslinked by a Michael's reaction where each of the hydrogel components is functionalized with nucleophiles. A third component is added to the two hydrogel components to crosslink the hydrogel components. This third component is a crosslinking functionality that is functionalized on both ends with electrophiles that react with the nucleophiles on the hydrogel components through Michael's reactions to crosslink the hydrogel components to one another in situ.

In an embodiment, a first hydrogel component functionalized with a nucleophile and a second hydrogel component functionalized with a nucleophile and with a biofunctionality at block 701 of FIG. 7a are placed within the first bore of a dual lumen delivery device, such as a two-bored needle or two-bored catheter. The first hydrogel component functionalized with a nucleophile may be thiolated collagen, collagen-laminin, or poly-1-lysine. The second hydrogel component functionalized with a nucleophile and a biofunctionality may be thiolated hyaluronan. A crosslinking functionality having several electrophiles X to react with the nucleophiles of the first and second hydrogels at block 702 of FIG. 7*a* is placed in the second bore of a dual lumen delivery device. Examples of crosslinking functionalities are illustrated in FIG. 7*b*. The crosslinking functionality may be difunctional PEG acrylates 700 or disulfides 710 where the R groups that functionalize the PEG acrylate 700 or the disulfide 710 may be any of the R groups 720 including acrylates 730, methacrylates 740, acrylamides 750, vinyl sulfones 760, and malamides 770. The contents of the first bore and the second bore are then delivered to an infarcted region of the heart at block 703 of FIG. 7*a*. When combined, the contents of the first bore are crosslinked to one another by the crosslinking functionality from the second bore 720 to form a bioscaffolding. The first hydrogel component and the second hydrogel component are crosslinked by a Michael's addition reaction by the electrophiles of the crosslinking functionality reacting with the nucleophiles of the first and second hydrogel components at block 704 of FIG. 7*a*.

Figure 7C:
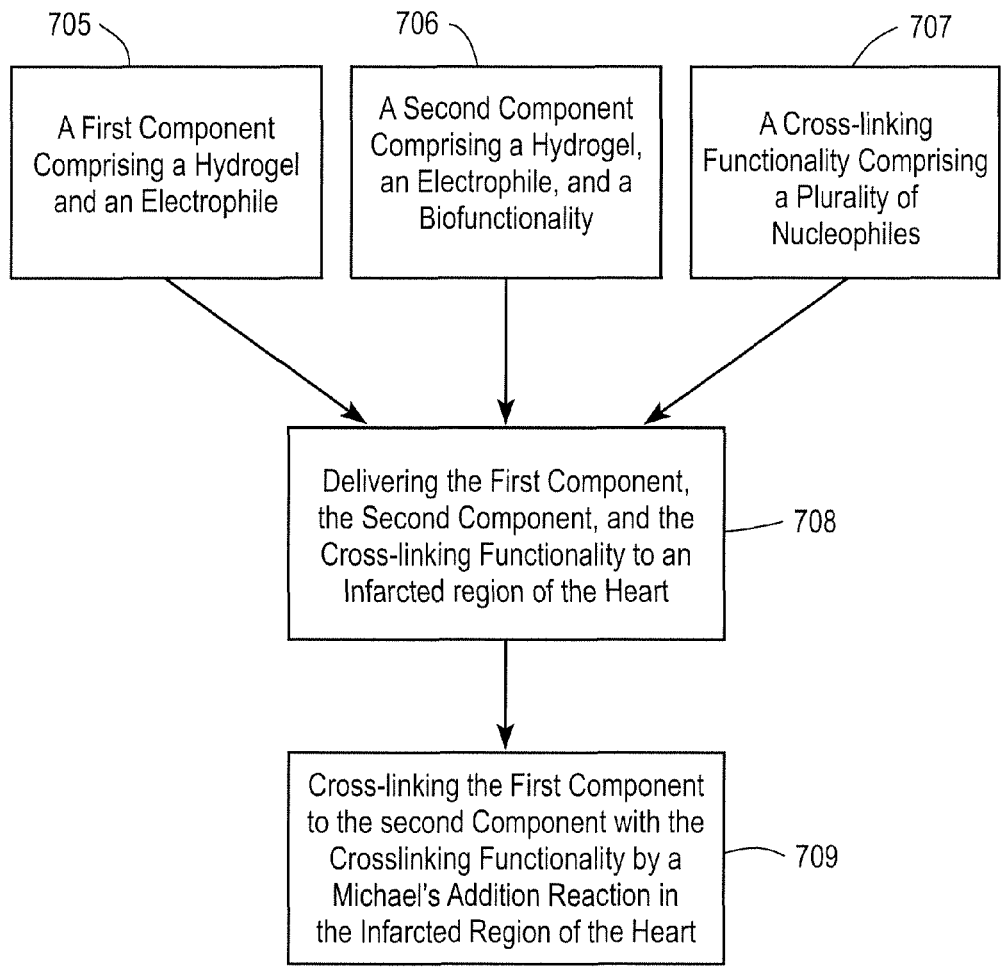
FIG. 7c is an alternate embodiment of the method of forming a bioscaffolding by crosslinking a first hydrogel component to a second hydrogel component by a crosslinking functionality.

In an alternate embodiment, illustrated in FIG. 7*c*, the first hydrogel component functionalized with a nucleophile at block 705 of FIG. 7*c* is placed in the first bore of a three-bored delivery device, a second hydrogel component functionalized with an nucleophile and with a biofunctionality at block 706 of FIG. 7*c* is placed in a second bore of the three-bored delivery device, and a crosslinking functionality having several electrophilic groups X at block 707 of FIG. 7*c* is placed in a third bore of the three-bore delivery device. The first hydrogel component, the second hydrogel component, and the cross-linking functionality are then delivered to an infarcted region of the heart at block 708 of FIG. 7*c*. The first hydrogel component and the third hydrogel component are then crosslinked by the crosslinking functionality by a Michael's addition reaction in the infarcted region of the heart at block 709 of FIG. 7*c*.

Figure 8A:
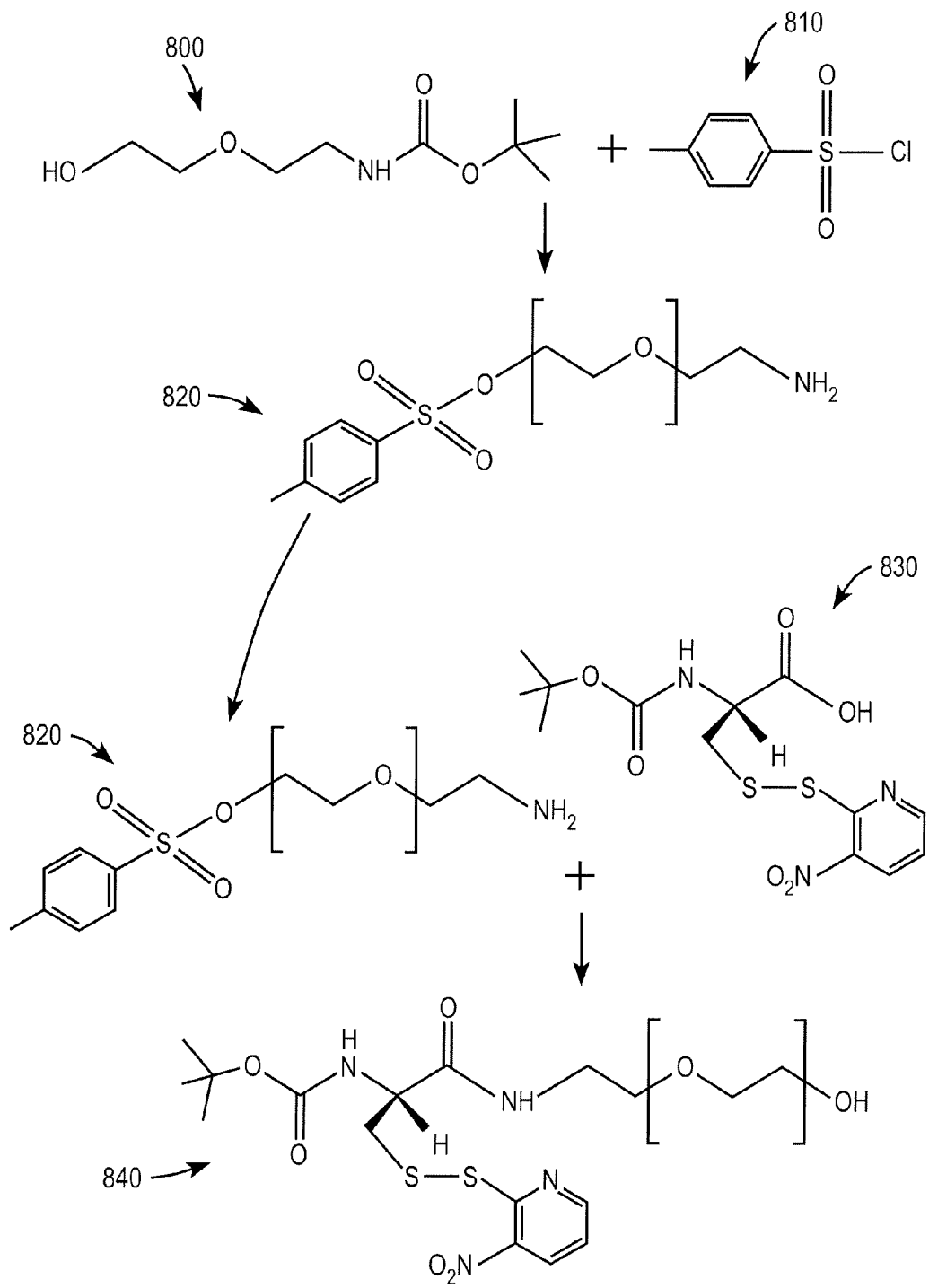
FIGS. 8a-8e illustrate an exemplary embodiment of the method of forming a bioscaffolding by crosslinking a first hydrogel component to a second hydrogel component by a crosslinking functionality.

FIGS. 8*a*-8*e* illustrate one particular method of the embodiment illustrated in FIG. 7*c*, where two hydrogel components functionalized with electrophiles are cross-linked into a bioscaffolding by a cross-linking agent. FIG. 8*a* illustrates the synthesis of a pegylated tBOC-Cysteine group 840 onto which a biofunctionality, such as PR11, may be bound and subsequently cleaved in situ. To synthesize the pegylated tBOC-Cysteine group 840, a 250 mL (milliliter) 3 necked round bottom flask under nitrogen with an addition funnel, nitrogen inlet/and outlet and condenser is provided for the reaction. To this flask, 20.0 grams of 6.25 millimolar polyethylene glycol amine 800 is dissolved in 100 mL of anhydrous toluene. To the dissolved polyethylene glycol amine, triethylamine (1.417 g/14.0 mmol) is added in the flask. Next, 4-tolsyl chloride (2.384 g/12.5 mmol) is added to the addition funnel. The solution in the flask is then diluted with 10 mL of anhydrous toluene. Tosyl chloride 810 is then added dropwise to the polyethylene glycol (PEG) solution and stirred at room temperature for an hour. The solution is then slowly heated to 60° C. and maintained at 60° C. for three hours. The toluene is then reduced on a rotary evaporator. Water is added to the solution and a pH of 3 is achieved and maintained. The solution is then stirred for four hours. The solution is then added to a dialysis tube (MWCO 3K) and dialysis is performed for 6 turnovers. The sample is then lypholyzed to form the tosylated polyethylene amine compound (tosyl-O-PEG-amine) 820. The tosyl-O-PEG-amine 820 is then placed in a 100 mL roundbottom flask with a nitrogen inlet/nitrogen outlet and condenser. To this flask, tBOC-cysteine(Npys) 830 is added (2.492 g/6.64 mmol) along with N,N-dicyclohexyl-carbodiimide (1.369 g/6.64 mmol) and tetrahydrofuran (50 mL). The solution is then stirred for 1 hour at room temperature under nitrogen. NHS (0.7639 g/6.64 mmol) is then added to the solution and the solution is then stirred for ½ hour at room temperature. The tosyl-O-PEG-amine 820 is dissolved THF and added with a syringe to the flask. The reaction is allowed to proceed overnight to form the pegylated tBOC-Cysteine group 840. After the reaction is completed, the sample is added to deionized water with the PH adjusted to pH 8.0. The pH is then adjusted to pH 12 with potassium hydroxide and stirred for 12 hours. The sample is subsequently dialysized with a 3K MWCO dialysis cartridge. The sample is then lypholyzed.

Figure 8B:
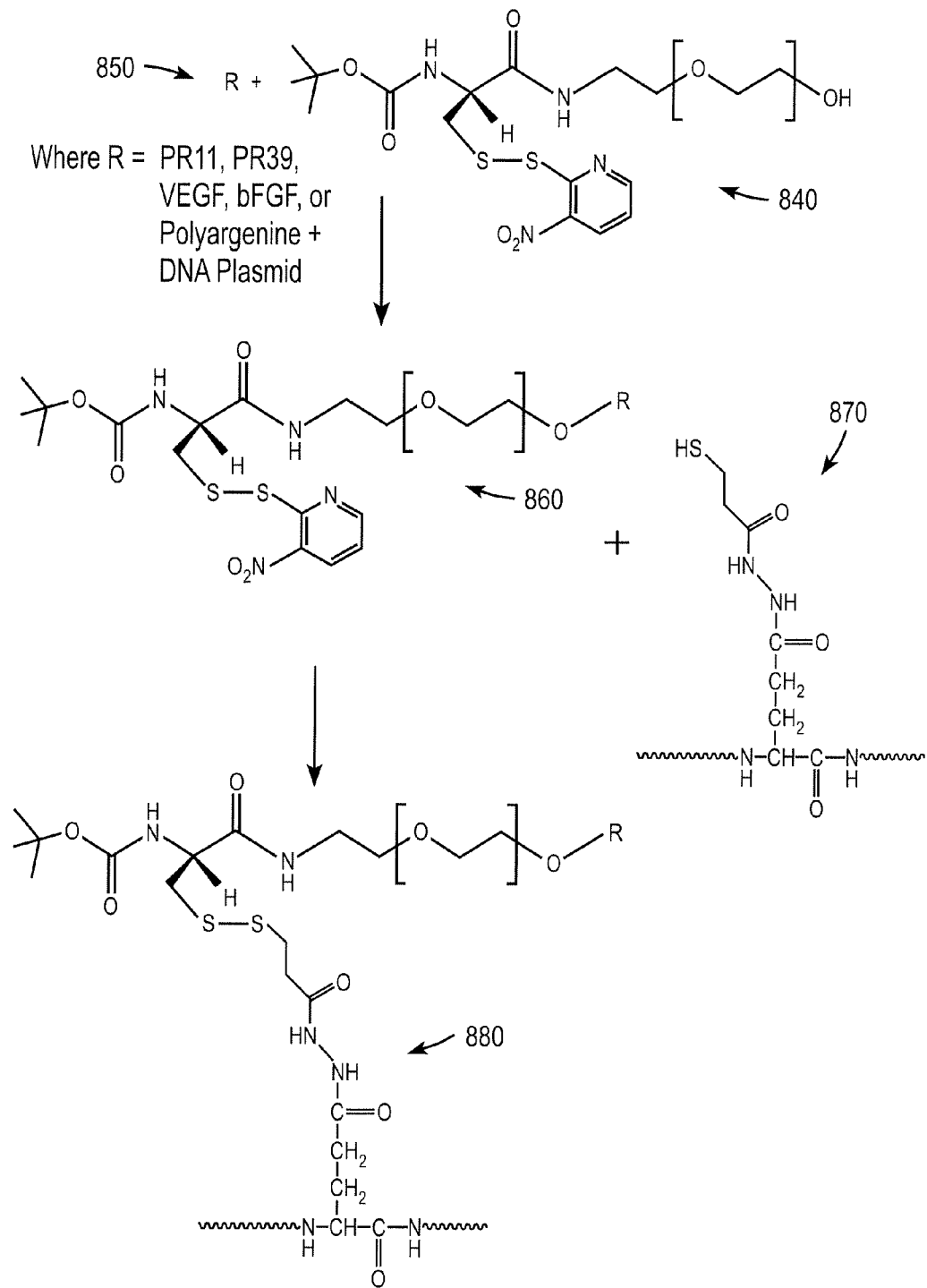
Figure 8C:
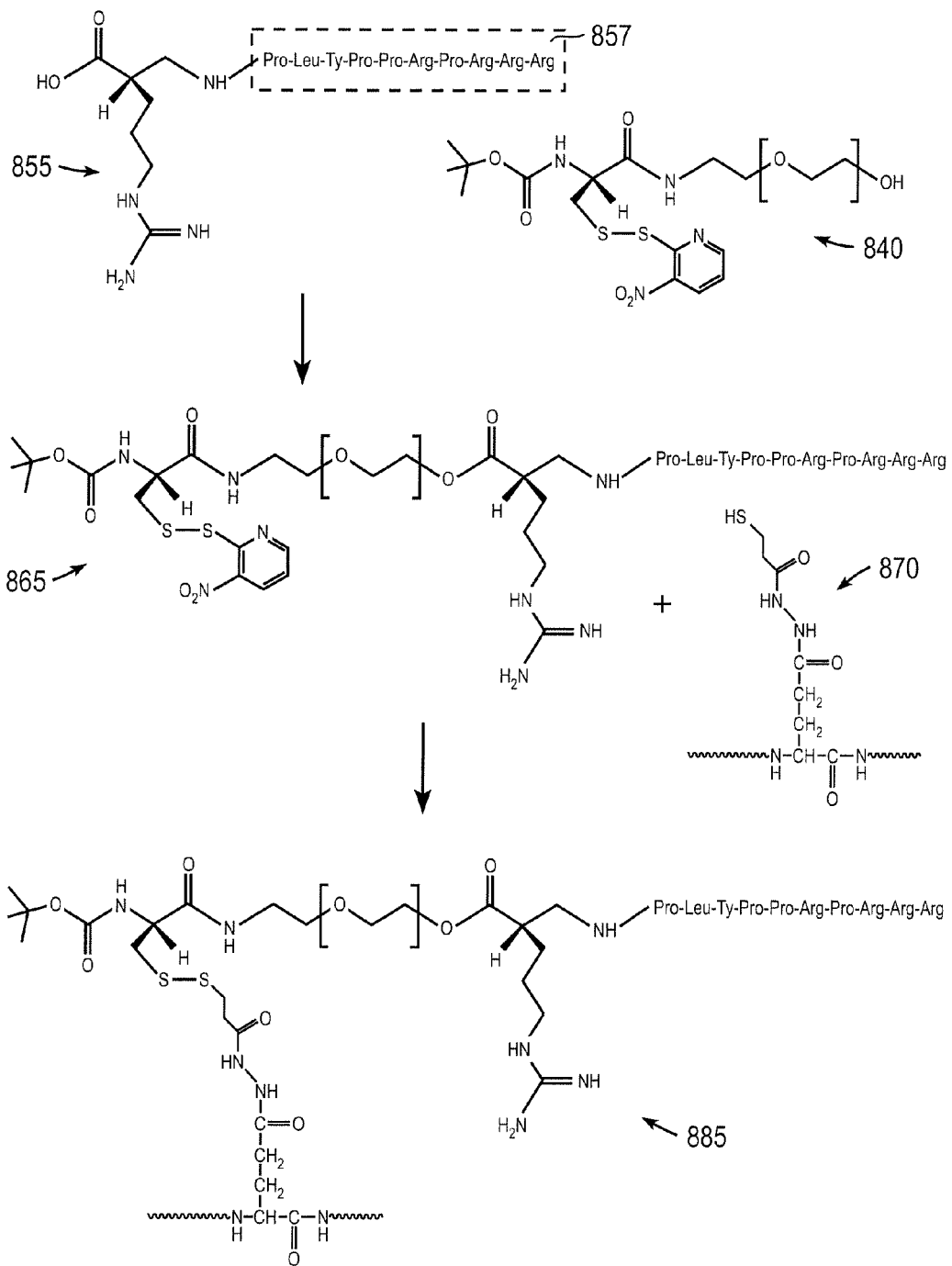
Figure 8D:
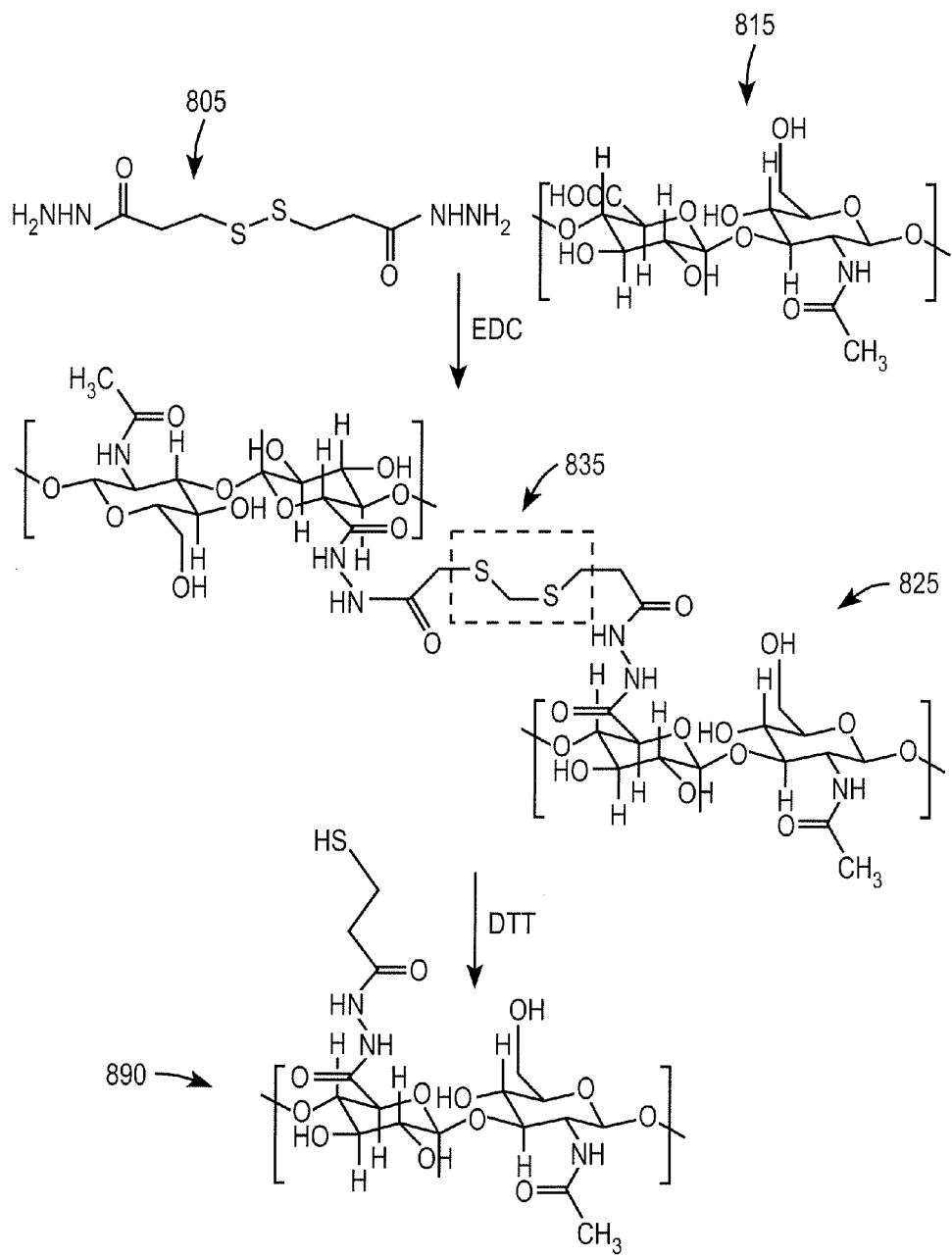
Figure 8E:
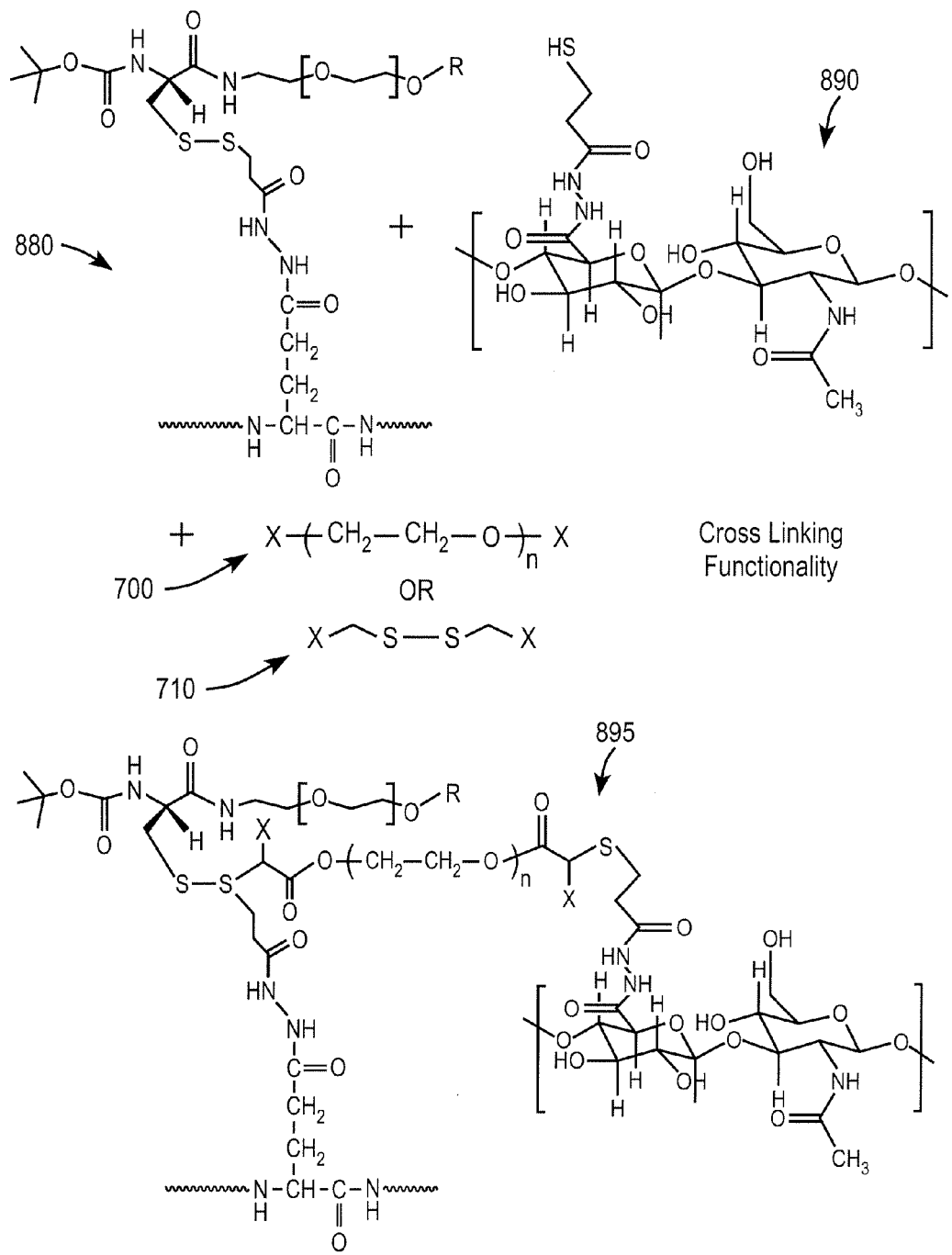

An R group 850 is then added to the pegylated tBOC-Cysteine group 840 to form compound 860, as illustrated in FIG. 8*b*. The R group 850 may be any one of the biofunctionalities such as PR11, PR39, VEGF, bFGF, or polyarginine complexed with a DNA plasmid. Compound 860 is then bound to thiolated collagen 870 to form compound 880. FIG. 8*c* illustrates the particular embodiment where the R group 850 is PR11 857 bound to pyridine 855. The PR11 857 bound to pyridine 855 is reacted with a pegylated tBOC-cysteine group 840 using standard carbodiimide coupling to form the ester linkage, compound 865. Compound 865 is then reacted with thiolated collagen to form the compound at 885.

The compound 860, bound to an R-group 850 as the biofunctionality, of FIG. 8*b* and the compound 865, bound to PR11 857 as the biofunctionality, of FIG. 8*c* may be the second hydrogel component having a nucleophile (the thiol group). This second hydrogel component having a nucleophile may be crosslinked to a first hydrogel component having a nucleophile, such as a thiolated hyaluronan hydrogel illustrated in FIG. 8*d*. The thiolated hyaluronan may be formed by adding 5 g of low molecular weight (molecular weight between 15 kiloDaltons (kD) and 100 kD) hyaluronan 815 dissolved in 500 g of water to a roundbottom flask. To the flask, 3,3'dithiobis(propionoic dihydrazide) 805 (2.975 g/12.4 mmol) is added to the hyaluronan 815 dissolved in water. The pH is then adjusted to 4.75 with hydrochloric acid. EDC (1.2 g) is then added to the flask and the pH is adjusted to maintain a pH of 4.75. With the formation of a solid mass in the flask, the reaction to form compound 825 is terminated by adjusting the pH to 7.0 with 1 molar NaOH. The disulfide bond 835 is cleaved by adding dithiothreitol DTT (25.0 g) to the flask. The pH is then adjusted to a pH of 8.5 with 1 molar NaOH. The solution within the flask is then stirred at room temperature for 24 hours to form the thiolated hyaluronan 890. The pH is then re-adjusted to a pH of 3.5 with 1 molar HCl. The sample is then dialysized in a dialysis tube in a media pH of 3.5, centrifuged, and lypholyzed.

The thiolated hyaluronan 890 is then crosslinked to thiolated collagen 880. The thiolated hyaluronan 890 is crosslinked to the collagen compound 880 through a crosslinking functionality 700 or 710 having electrophiles X, such as those illustrated in FIG. 7*b* by a Michael's addition reaction between the nucleophilic thiolate groups on the collagen 880 and the hyaluronan 890 hydrogels and the electrophiles X on the cross-linking functionalities 700 or 710. The crosslinked hyaluronan and collagen compound 895 results. In an alternate embodiment the thiolated hyaluronan 890 and the thiolated collagen 880 may be cross-linked to form disulfide bonds by an oxidative process as described above, in the absence of the cross-linking functionality 700 or 710.

Figure 9A:
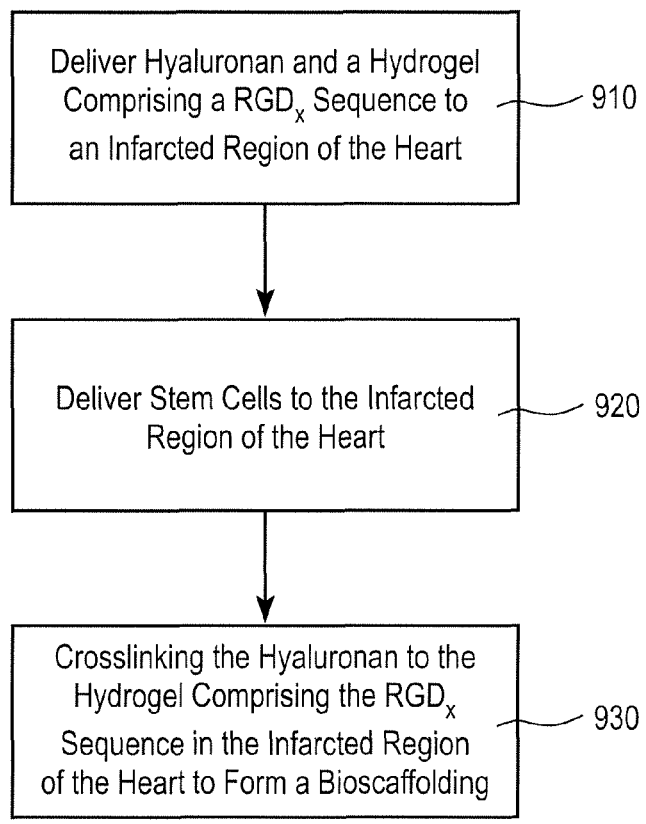
FIG. 9a is a flow chart illustrating a method of injecting bioscaffolding components into the infarct region of the heart along with stem cells.
Figure 9B:
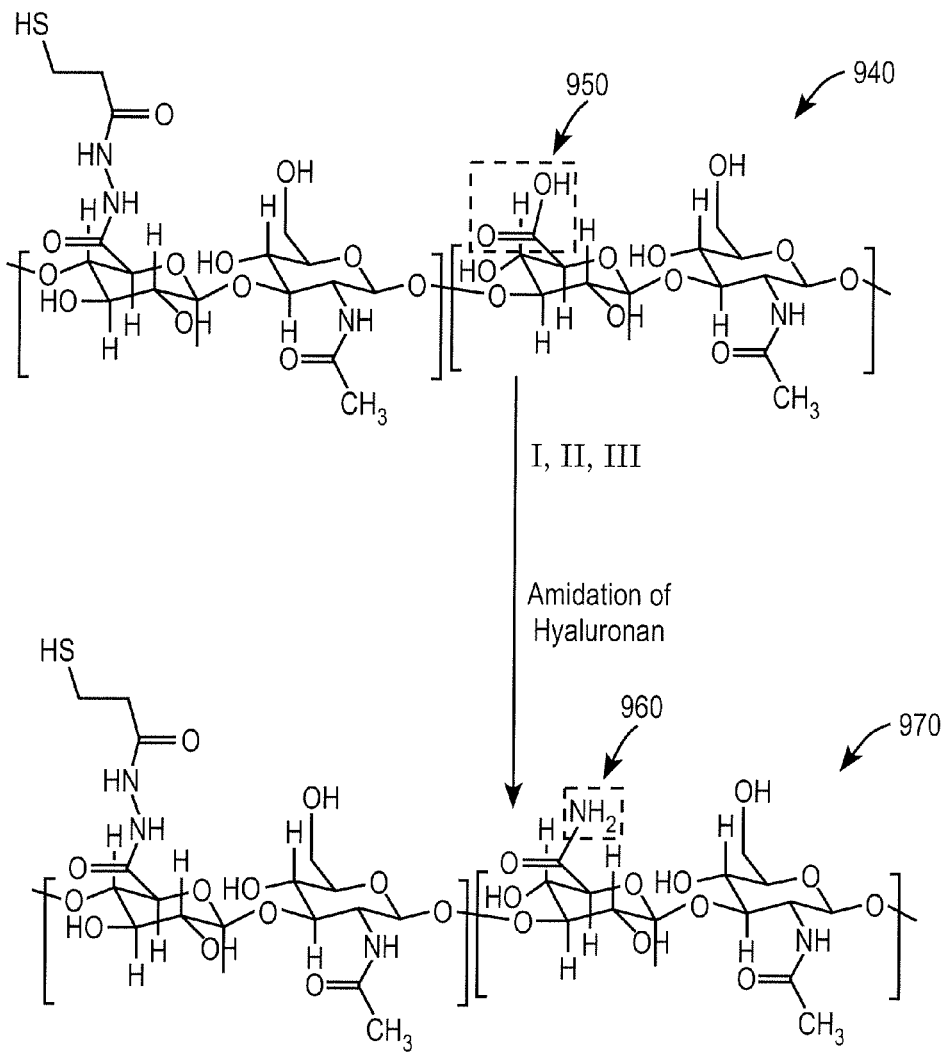
FIGS. 9b-9c illustrate forming a bioscaffolding with hyaluronan and fibrin.
Figure 9C:
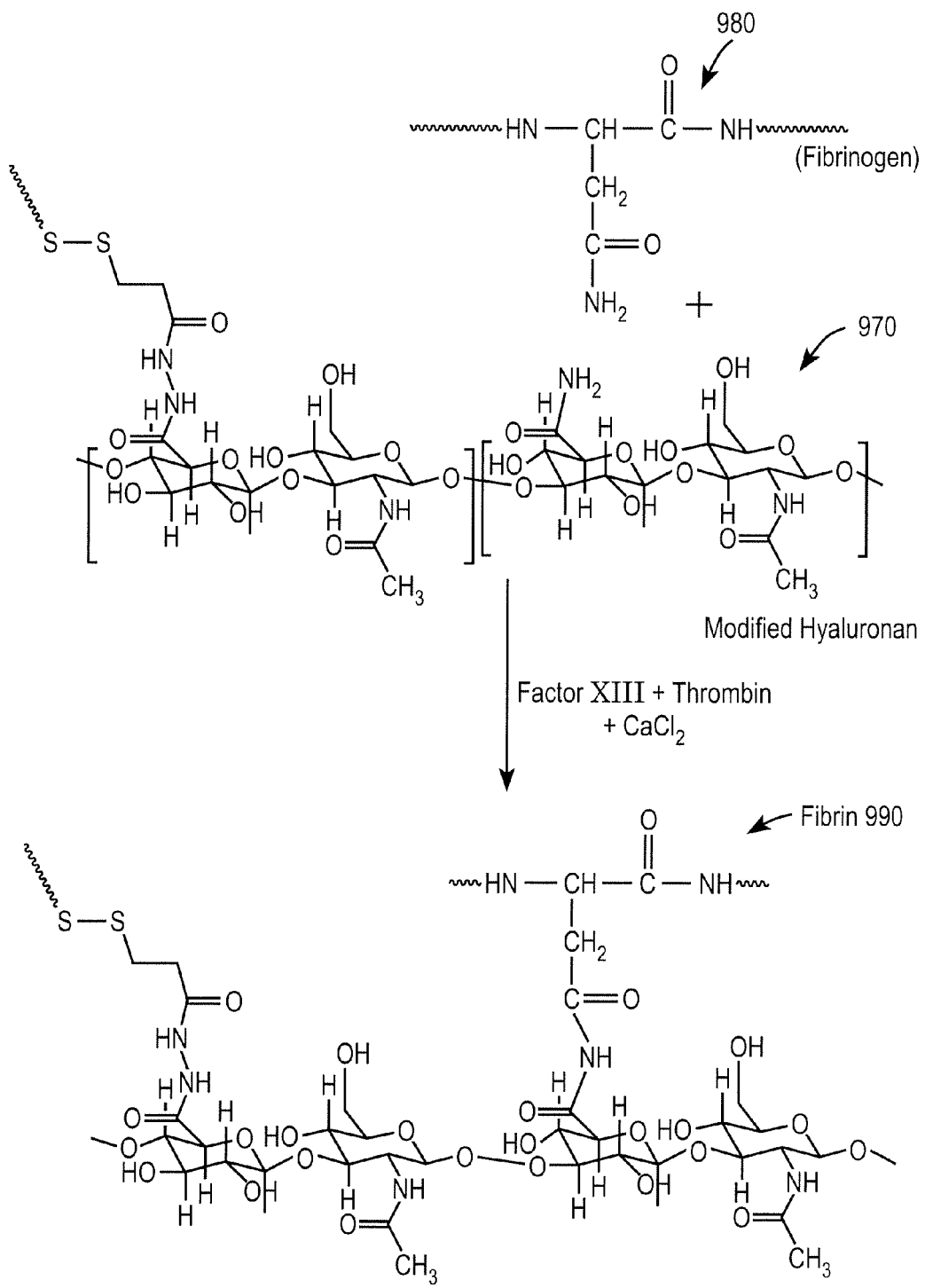

In yet another embodiment, the bioscaffolding components may be injected into the infarct region of the heart along with stem cells to promote the angiogenesis of the heart. In this embodiment, the bioscaffolding may be formed of hyaluronan and a hydrogel that has an RGDx sequence. As shown in FIG. 9a, the hyaluronan and the hydrogel comprising an RGDx sequence is delivered to an infracted region of the heart at block 910. Stem cells, such as mesenchymal stem cells, are also delivered to the infarcted region of the heart at block 920. The amount of stem cells delivered to the infarcted region may be in the approximate range of 5 million and 300 million delivered through multiple injections. The number of injections varies depending on the amount of stem cells delivered and may be in the approximate range of 10 to 30 injections. Once delivered to the infracted region of the heart the hyaluronan and the hydrogel comprising the RGDx sequence crosslink to form a bioscaffolding at block 930. In one particular embodiment, the bioscaffolding is formed of hyaluronan and the hydrogel collagen that has an RGDx sequence. The hyaluronan and the collagen may be crosslinked in situ in an infarct region of the heart by any of the methods described above. Those methods include crosslinking hyaluronan to collagen by a Michael's addition or by a disulfide bond formed by an oxidative process. Stem cells are co-injected along with the hyaluronan and the collagen into the infarct region of the heart. In another particular embodiment, the bioscaffolding may be formed of hyaluronan and fibrin. Fibrin is a hydrogel that has the RGDx sequence. The bioscaffolding is crosslinked in situ by a transamidation of hyaluronan with fibrinogen during the conversion of fibrinogen polymer to fibrin with Factor XIIIa as illustrated in FIGS. 9b and 9c. FIG. 9b illustrates the amidation of the non-reacted carboxylate functionalities 950 of hyaluronan 940 to the amides 960 of the amidated hyaluronan 970. FIG. 9c illustrates the crosslinking of the amidated hyaluronan 970 with fibrinogen 980. The amidated hyaluronan 970 and the fibrinogen 980 are crosslinked in situ in an infarcted region of the heart by injecting the amidated hyaluronan 970 and the fibrinogen 980 together from a single lumen or from two separate lumens while simultaneously injecting a calcium chloride enriched buffered solution of thrombin and mesenchymal cells down a lumen different from that delivering the hydrogels. In an embodiment, the hydrogels and the calcium chloride enriched buffered solution of thrombin and mesenchymal cells are injected into the border zone of the infarcted region of the heart. Within the infarct site the fibrinogen is converted to a fibrin monomer and polymer and the Factor XIIIa transamidate the hyaluronan 970 with the fibrin 990.

In another embodiment, the fibrin bioscaffolding may be formed by cross-linked fibrinogen hydrogel components that are co-injected with stem cells and a pore forming agent. Fibrin forms a solid gel structure with minimal porosity and the stem cells are initially locked within the bioscaffolding. The pore forming agent forms pores in the fibrin matrix to allow the stem cells to diffuse out of the fibrin bioscaffolding. The pore forming agent is water soluble and may be a sugar (e.g. D-mannitol), proteins (e.g. bovine serum albumin (BSA)), salts (e.g. NaCl), or high molecular weight polyethylene glycol (PEG) (e.g. PEG having a molecular weight of 3400 grams/mole.) Suitable molecular weights are 200 to 100,000, but preferably 300 to 20,000. Other hydrophilic materials useful as porogens are PVP (polyvinyl pyrrolidone), sodium carboxymethyl cellulose (CMC), dextran, sodium alginate, hyaluronic acid, chondroitan sulfate. Commercially available molecular weights may be higher than desired for some materials, but they can be reduced by acid digestion (e.g. HCl for hyaluronan and CMC), or enzymatically (e.g. alginate lyase for Na-Alginate.) The water soluble pore forming agents are biocompatible and dissolve away to form water channels within the first 24 hours after the formation of the fibrin bioscaffolding. During this period of time, cells can spread into these channels and assume their healthy, normal, cell shapes. It is valuable that the bioscaffolding has an interconnected porous structure to maintain a healthy cell environment. Increased gas, waste and nutrient diffusion in and out of the fibrin matrix also increased the viability of the stem cells within the bioscaffolding. The size and interconnectivity of the porous channels within the fibrin matrix may be engineered to prevent the brittleness of the fibrin matrix by parameters including the concentration, the type, and the molecular weight of the pore forming agent. Different agents will have different levels of incompatibility with the gel matrix, hence this will affect porogen domain size. A pore forming agent may also be included with any of the other hydrogel components described herein that are used to form bioscaffoldings to increase the porosity of the bioscaffolding. The increased porosity of any of the bioscaffoldings described herein may be valuable in increasing the out-diffusion of the angiogenic factors, microspheres, or oligomeric materials within the bioscaffolding.

The bioscaffolding may also be formed on a stent or a pacemaker lead. Bioscaffoldings that are formed on a stent or a cardiac medical device may have biofunctionalities, DNA plasmids, or DNA/PEI complexes that are suited to the particular use of the stent or the cardiac medical device. The cardiac medical device may be a lead for a pacing device, a defibrillator device, or a resynchronization therapy device. The bioscaffolding may be formed of a plurality of crosslinked hydrogel components. The plurality of crosslinked hydrogel components may be a combination of a first hydrogel component and a second hydrogel component, where both the first hydrogel component and the second hydrogel components are found in the extracellular matrix (ECM) of the body. In particular, the first hydrogel component may be hyaluronan and the second hydrogel component may be collagen, collagen-laminin, or poly-1-lysine. The use of a bioscaffolding formed of ECM components may be valuable in providing a stent having a coating that is compatible with the body and will not cause a great deal of inflammation and acid production in the area of the stent or the cardiac medical device that would damage the area as well as the stent or the cardiac medical device. Additionally, components of the ECM may be broken down by the body by enzymes found naturally within the body. As described above, the first and second hydrogel components may include functionalities that allow them to react with one another through a Michael's addition reaction to cross-link. The first hydrogel component of the bioscaffolding may be hyaluronan. The second hydrogel component of the bioscaffolding may be collagen, collagen-laminin, or poly-1-lysine. In one embodiment, the bioscaffolding may be formed on the stent or the cardiac medical device by spraying the first hydrogel component and the second hydrogel component onto the stent or the cardiac medical device from separate sources so that they react to form a cross-linked bioscaffolding after being sprayed onto the stent or the cardiac medical device. The first and second hydrogel components must come from separate sources so that they do not mix together and crosslink before being sprayed onto the cardiac medical device. In one embodiment, the first hydrogel component may be sprayed onto the cardiac medical device before the second hydrogel component is sprayed onto the cardiac medical device. In an alternate embodiment the second hydrogel may be sprayed onto the cardiac medical device before the first hydrogel component is sprayed onto the cardiac medical device. In yet another embodiment, the first and second hydrogel components may be sprayed simultaneously onto the cardiac medical device. Prior to spraying the hydrogel components onto metal cardiac medical devices, a polymeric primer coat may be applied to the surface of the metal cardiac medical device where the bioscaffolding is to be formed. The bioscaffolding is then aged in a high oxygen atmosphere overnight (in the approximate range of 6 hours and 12 hours.) The bioscaffolding is then dried in a convection oven and processed as described in literature known to one of skill in the art.

A stent or a cardiac medical device may also be coated with nucleic acid fragments of DNA or RNA to be transfected into the cells in the area where the stent or the cardiac medical device is placed in vivo. The transfected DNA or RNA may express proteins that are beneficial to the particular region of the body where the stent or cardiac medical device is placed. For example, proteins that are beneficial to be expressed in the region of a stent are proteins that inhibit or interfere with excessive smooth tissue cell proliferation (restenosis) or are anti-apoptotic factors. The nucleic acid fragments of DNA or RNA may be part of a plasmid complex. Alternatively, the nucleic acid fragments may be a DNA/PEI complex.

Figure 10:
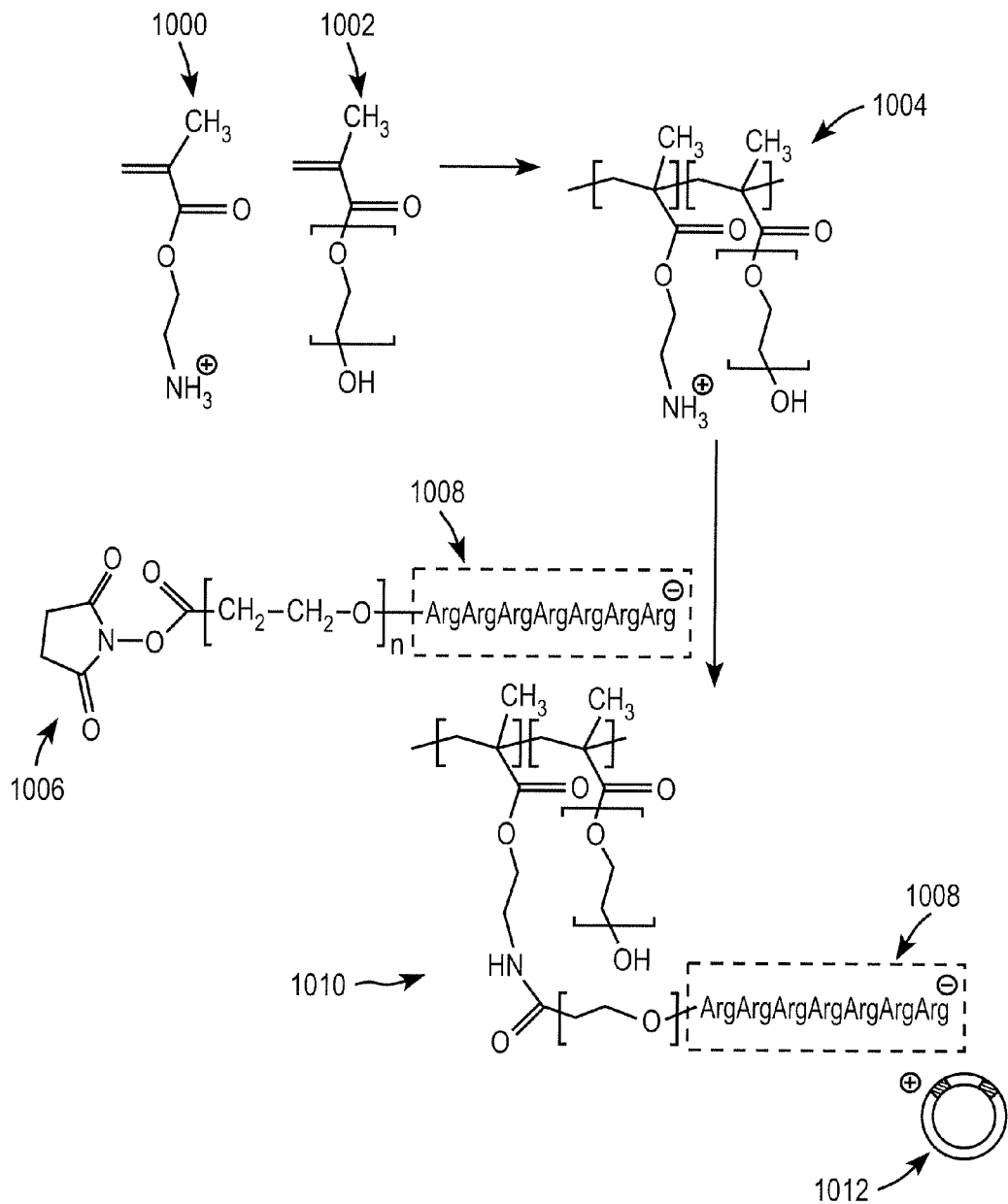
FIG. 10 illustrates an embodiment of forming a polymer bound to a plasmid through a polyarginine to serve as a coating for a medical device.

The nucleic acid fragments of DNA or RNA may be coupled to the stent or cardiac medical devices as part of a bioscaffolding, as described above. In another embodiment, the nucleic acid fragments of DNA or RNA may be coupled to the stent or to cardiac medical devices by ionically coupling a plasmid construct to polyarginine groups on a polymer coating. FIG. 10 illustrates forming the polymer 1004, binding polyarginine 1008 to the polymer 1004, and coupling a plasmid 1012 to the polyarginine 1008. A coating of the polymer 1004 is formed on the stent or cardiac medical device by reacting monomers of aminoethyl methacrylate or aminopropyl methacrylate 1000 with poly(ethylene glycol) methacrylate or poly(ethylene glycol) acrylate 1002. The polymer 1004 is then reacted with the compound 1006 that includes polyarginine 1008 to form the compound 1010. The polymer compound 1010 that has the negatively charged polyarginine groups 1008 is then coupled via ionic interactions to the positively charged plasmids 1012 containing the DNA or RNA nucleic acid fragments. Once placed in vivo, the plasmids 1012 dissociate from the polymer 1010 by ion exchange and may become transfected into the surrounding cells where the DNA or RNA within the plasmids 1008 may be expressed as proteins.

In another embodiment, nucleic acid fragments of DNA or RNA may be coupled to a jacket of a cardiac medical device. The jacket of the cardiac medical device may be a silicone jacket or a urethane lead jacket on a cardiac medical device such as a lead for a cardiac pacing device, a defibrillator device, or a resynchronization therapy device. The jacket is treated with an allyl amine plasma having a plasma field with a high energy in the approximate range of 90 W and 150 W, depending on the architecture of the plasma chamber. The allyl amine plasma will form primarily tertiary amines on the jacket. The teriary amines are then ionized to quaternary amines by a reaction with an acid or an alkyl halide such as hydrochloric acid. Similar methods are described in United States Published Patent Applications 20020146557 and 20050031874. Subsequent immersion of the jacket in a plasmid solution will cause ionic binding of the positively charged plasmids to the negatively charged quaternary amines. Once placed in vivo, the plasmids may dissociate from the jacket by ion exchange and may become transfected into the surrounding cells where the DNA or RNA within the plasmids may be expressed as proteins.

While the exemplary embodiment of the present invention has been described in some detail for clarity of understanding and by way of example, a variety of adaptations, changes and modifications will be obvious to those who are skilled in the art. Hence the scope of the present invention is limited solely by the following claims.

We claim:

1. A method of forming a bioscaffolding, comprising:
   delivering a first component comprising hyaluronan functionalized with an electrophile to an infarcted region of a heart; delivering a second component comprising a hydrogel component functionalized with a nucleophile and having a biofunctional group bound thereto to the infarcted region of the heart; and cross-linking the first component and the second component in the infarcted region of the heart by a Michael's addition reaction, wherein the hydrogel component is selected from the group consisting of collagen, collagen-laminin, poly-1-lysine, and fibrinogen.

2. The method of forming a bioscaffolding of claim 1, wherein delivering the first component and the second component comprises injecting the first component through a first bore of a two-bored delivery device into the infarcted region of the heart and injecting the second component through a second bore of the two-bored delivery device into the infarcted region of the heart.

3. The method of forming a bioscaffolding of claim 1, wherein the biofunctional group is selected from the group consisting of a PR11 peptide, a PR39 peptide, a vascular endothelial growth factor (VEGF), a basic fibroblast growth factor (bFGF), a polyarginine/DNA plasmid complex, and a DNA/polyethyleneimine (PEI) complex.

4. The method of forming a bioscaffolding of claim 1, further comprising delivering stem cells to the infarcted region of the heart.

5. The method of claim 1, wherein the electrophilic component is selected from one of pegylated acrylate, pegylated methacrylate, pegylated vinyl sulfone or pegylated maleimide.

6. The method of claim 5, wherein the nucleophilic component comprises poly-1-lysine.

\* \* \* \* \*

SEQUENCE LISTING

```
<160> NUMBER OF SEQ ID NOS: 2

<210> SEQ ID NO 1
<211> LENGTH: 11
<212> TYPE: PRT
<213> ORGANISM: Unknown
<220> FEATURE:
<223> OTHER INFORMATION: PR11

<400> SEQUENCE: 1

Arg Arg Arg Pro Arg Pro Pro Tyr Leu Pro Arg
1               5                   10

<210> SEQ ID NO 2
<211> LENGTH: 5
<212> TYPE: PRT
<213> ORGANISM: Unknown
<220> FEATURE:
<223> OTHER INFORMATION: Polyarginine

<400> SEQUENCE: 2

Arg Arg Arg Arg Arg
1               5
```